US011571482B2

(12) United States Patent
Coppi et al.

(10) Patent No.: US 11,571,482 B2
(45) Date of Patent: Feb. 7, 2023

(54) HUMAN ANTIBODIES TO S. AUREUS HEMOLYSIN A TOXIN

(71) Applicant: Regeneron Pharmaceuticals, Inc., Tarrytown, NY (US)

(72) Inventors: Alida Coppi, Flushing, NY (US); Peter Mason, Somerville, MA (US); William Olson, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 192 days.

(21) Appl. No.: 17/159,920

(22) Filed: Jan. 27, 2021

(65) Prior Publication Data

US 2021/0162059 A1 Jun. 3, 2021

Related U.S. Application Data

(60) Continuation of application No. 16/575,755, filed on Sep. 19, 2019, now Pat. No. 10,940,211, which is a division of application No. 15/860,174, filed on Jan. 2, 2018, now Pat. No. 10,463,748.

(60) Provisional application No. 62/441,786, filed on Jan. 3, 2017.

(51) Int. Cl.
| | |
|---|---|
| *C07K 16/12* | (2006.01) |
| *C07K 14/31* | (2006.01) |
| *A61K 47/68* | (2017.01) |
| *A61K 31/573* | (2006.01) |
| *A61K 39/00* | (2006.01) |

(52) U.S. Cl.
CPC ........ *A61K 47/6803* (2017.08); *A61K 31/573* (2013.01); *C07K 14/31* (2013.01); *C07K 16/1271* (2013.01); *A61K 2039/505* (2013.01); *C07K 2317/21* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,715,673 B2 | 5/2014 | Riggers | |
| 8,840,906 B2 | 9/2014 | Bubeck-Wardenburg | |
| 9,181,329 B2 | 11/2015 | Bubeck-Wardenburg | |
| 9,249,215 B2 | 2/2016 | Michael | |
| 9,527,905 B2 | 12/2016 | Sellman | |
| 9,845,348 B2 | 12/2017 | Sellman | |
| 10,463,748 B2 | 11/2019 | Coppi et al. | |
| 10,940,211 B2 | 3/2021 | Coppi et al. | |
| 2013/0164308 A1 | 6/2013 | Foletti et al. | |
| 2013/0189249 A1 | 7/2013 | Bubeck-Wardenburg | |
| 2015/0165015 A1 | 6/2015 | Taylor | |

FOREIGN PATENT DOCUMENTS

| | | |
|---|---|---|
| AU | 2007-259415 B2 | 9/2013 |
| AU | 2009-246510 B2 | 2/2014 |
| EP | 2284193 A1 | 2/2011 |
| EP | 2668208 B1 | 6/2015 |
| WO | 86/002358 A1 | 4/1986 |
| WO | 00/071585 A1 | 11/2000 |
| WO | 07/145689 A1 | 12/2007 |
| WO | 09/029831 A1 | 3/2009 |
| WO | 09/140236 A2 | 11/2009 |
| WO | 11/018208 A1 | 2/2011 |
| WO | 12/031260 A2 | 3/2012 |
| WO | 12/109285 A2 | 8/2012 |
| WO | 13/013323 A1 | 1/2013 |
| WO | 13/093693 A1 | 6/2013 |
| WO | 13/156534 A1 | 10/2013 |
| WO | 14/074470 A1 | 5/2014 |
| WO | 15/196011 A1 | 12/2015 |
| WO | 16/166223 A1 | 10/2016 |

OTHER PUBLICATIONS

Colman (Res Immunology 145:33-36, 1994).*
Bendig, "Humanization of Rodent Monoclonal Antibodies by CDR Grafting," Methods: A Companion to Methods in Enzymology, vol. 8:83-93, (1995).
Bhakdi S, et al. 1989. Human hyperimmune globulin protects against the cytotoxic action of staphylococcal alpha-toxin in vitro and in vivo. Infect Immun. 57:3214. PMID: 2777380.
Blomqvist L and Sjögren A. 1988. Production and characterization of monoclonal antibodies against *Staphylococcus aureus* alpha-toxin. Toxicon. 26:265. PMID: 3394159.
Chen et al., "Enhancement and destruction of antibody function by somatic mutation: unequal occurrence is controlled by V gene combinatorial associations," EMBO Journal, vol. 14 (No. 12):2784-2794, (1995).
Diep BA, et al. 2016. Improved Protection in a Rabbit Model of Community-Associated Methicillin-Resistant *Staphylococcus aureus* Necrotizing Pneumonia upon Neutralization of Leukocidins in Addition to Alpha-Hemolysin. Antimicrob Agents Chemother. 60:6333. PMID: 27527081.
Diep BA, et al. 2016. IVIG-mediated protection against necrotizing pneumonia caused by MRSA Sci Transl Med. 8:357ra124. PMID: 27655850.
Diep BA, et al. 2017. Targeting Alpha Toxin to Mitigate Its Lethal Toxicity in Ferret and Rabbit Models of *Staphylococcus aureus* Necrotizing Pneumonia. Antimicrob Agents Chemother. 61: e02456. PMID: 28115346.

(Continued)

*Primary Examiner* — Patricia Duffy
(74) *Attorney, Agent, or Firm* — Schwabe, Williamson & Wyatt PC; Gabe Amodeo

(57) ABSTRACT

The present invention provides antibodies that bind to *Staphylococcus aureus* Hemolysin A toxin, and methods of use. According to certain embodiments of the invention, the antibodies are fully human antibodies that bind to Hemolysin A. The antibodies of the invention are useful for inhibiting or neutralizing Hemolysin A activity, thus providing a means of preventing or treating a Hemolysin A-related disease or disorder such as *S. aureus* infection. In some embodiments, the antibodies of the present invention are used in treating at least one symptom or complication of a *S. aureus* infection.

16 Claims, 19 Drawing Sheets

Specification includes a Sequence Listing.

(56) References Cited

OTHER PUBLICATIONS

Edwards et al., "The Remarkable Flexibility of the Human Antibody Repertoire; Isolation of Over One Thousand Different Antibodies to a Single Protein, LByS," J. Mol. Biol., vol. 334:103-118, (2003).
Foletti D, et al. 2013. Mechanism of Action and In Vivo Efficacy of a Human-Derived Antibody against *Staphylococcus aureus* α-Hemolysin J Mol Biol. 425:1641-1654, PMID: 23416200.
Goni et al., "*E coli* α-hemolysin: a membrane-active protein toxin," Brazilian Journal of Medical and Biological Research, vol. 31(8):1019-1034, (1998).
Harshman S, et al. 1989. Reaction of staphylococcal alpha-toxin with peptide-induced antibodies. Infect Immun. 57:3856. PMID: 2509372.
Heveker N, et al. 1994. A human monoclonal antibody with the capacity to neutralize *Staphylococcus aureus* alpha-toxin. Hum Antibodies Hybridomas. 5:18. PMID: 7858179.
Heveker N, et al. 1994. Characterization of neutralizing monoclonal antibodies directed against *Staphylococcus aureus* alpha-toxin. Hybridoma. 13:263. PMID: 7528719.
Hilliard JJ, et al. 2015. Anti-alpha-toxin monoclonal antibody and antibiotic combination therapy improves disease outcome and accelerates healing in a *Staphylococcus aureus* dermonecrosis model. Antimicrob Agents Chemother. 59:299. PMID: 25348518.
Hua L, et al. 2014. Assessment of an anti-alpha-toxin monoclonal antibody for prevention and treatment of *Staphylococcus aureus*-induced pneumonia. Antimicrob Agents Chemother. 58:1108. PMID: 24295977.
Hua L, et al. 2015. MEDI4893* Promotes Survival and Extends the Antibiotic Treatment Window in a *Staphylococcus aureus* Immunocompromised Pneumonia Model. Antimicrob Agents Chemother. 59:4526. PMID: 25987629.
Kennedy AD, et al. 2010. Targeting of alpha-hemolysin by active or passive immunization decreases severity of USA300 skin infections in a mouse model. J Infect Dis. 202:1050. PMID: 20726702.
Kussie et al., "A Single Engineered Amino Acid Substitution Changes Antibody Fine Specificity," Journal of Immunology, vol. 152:146-152, (1994), Table 1.
Le VT, et al. 2016. Critical Role of Alpha-Toxin and Protective Effects of Its Neutralization by a Human Antibody in Acute Bacterial Skin and Skin Structure Infections. Antimicrob Agents Chemother. 60:5640. PMID: 27401576.
Lee et al., "Complete humanization of the mouse immunoglobulin loci enables efficient therapeutic antibody discovery," Nature Biotechnology, vol. 4(4):356-367, (Apr. 2014).
Menzies BE and Kernodle DS. 1996. Passive immunization with antiserum to a nontoxic alpha-toxin mutant from *Staphylococcus aureus* is protective in a murine model. Infect Immun. 64:1839. PMID: 8613399.
Mocca CP, Brady RA and Burns DL. 2014. Role of antibodies in protection elicited by active vaccination with genetically inactivated alpha hemolysin in a mouse model of *Staphylococcus aureus* skin and soft tissue infections. Clin Vaccine Immunol. 21:622. PMID: 24574539.
Oganesyan V, et al. 2013. Crystallization and preliminary X-ray diffraction analysis of the complex between a human anti-alpha toxin antibody fragment and alpha toxin. Acta Crystallogr Sect F Struct Biol Cryst Commun. 69:302. PMID: 23519809.
Oganesyan V, et al. 2014. Mechanisms of neutralization of a human anti-α-toxin antibody, J Biol Chem. 289:29874. PMID: 25210036.
Ortines RV, et al. 2018. Neutralizing α-toxin accelerates healing of *Staphylococcus aureus*-infected wounds in normal and diabetic mice. Antimicrob Agents Chemother. doi: 10.1128/AAC.02288-17. [Epub ahead of print] PMID: 29311091.
Oscherwitz J and Cease KB. 2015. Identification and validation of a linear protective neutralizing epitope in the β-pore domain of alpha toxin. PLoS One. 10: e0116882. PMID: 25635901.
Oscherwitz J, et al. 2014. In vivo mapping of a protective linear neutralizing epitope at the N-terminus of alpha hemolysin from *Staphylococcus aureus*. Mol Immunol. 60:62. PMID: 24769493.
Ragle BE and Bubeck Wardenburg J. 2009. Anti-alpha-hemolysin monoclonal antibodies mediate protection against *Staphylococcus aureus* pneumonia. Infect Immun. 77:2712. PMID: 19380475.
Rauch S, et al. 2012. Abscess formation and alpha-hemolysin induced toxicity in a mouse model of *Staphylococcus aureus* peritoneal infection. Infect Immun. 80:3721. PMID: 22802349.
Rouha H, et al. 2015. Five birds, one stone: Neutralization of α-hemolysin and 4 bi-component leukocidins of *Staphylococcus aureus* with a single human monoclonal antibody. Mabs. 7:243. PMID: 25523282.
Rouha H, et al. 2017. Disarming *Staphylococcus aureus* from destroying human cells by simultaneously neutralizing six cytotoxins with two human monoclonal antibodies. Virulence. 3:1. PMID: 29099326.
Tabor DE, et al. 2016. *Staphylococcus aureus* Alpha-Toxin Is Conserved among Diverse Hospital Respiratory Isolates Collected from a Global Surveillance Study and Is Neutralized by Monoclonal Antibody MEDI4893. Antimicrob Agents Chemother. 60:5312. PMID: 27324766.
Tkaczyk C, et al. 2012. Identification of Anti-Alpha Toxin Monoclonal Antibodies That Reduce the Severity of *Staphylococcus aureus* Dermonecrosis and Exhibit a Correlation between Affinity and Potency. Clin Vaccine Immunol. 19:377. PMID: 22237895.
Tkaczyk C, et al. 2013. *Staphylococcus aureus* alpha toxin suppresses effective innate and adaptive immune responses in a murine dermonecrosis model. PLoS One. 8: e75103. PMID: 24098366.
Tkaczyk C, et al. 2016. Targeting Alpha Toxin and ClfA with a Multi-mechanistic Monoclonal-Antibody-Based Approach for Prophylaxis of Serious *Staphylococcus aureus* Disease. MBio. 7: e00528. PMID: 27353753.
Tkaczyk C, et al. 2017. Multi-mechanistic Monoclonal Antibodies (MAbs) Targeting *Staphylococcus aureus* Alpha-Toxin and Clumping Factor A: Activity and Efficacy Comparisons of a MAb Combination and an Engineered Bispecific Antibody Approach. Antimicrob Agents Chemother. 61 e00629. PMID: 28584141.
U.S. Appl. No. 15/860,174, Requirement for Restriction/Election dated Aug. 15, 2018.
U.S. Appl. No. 15/860,174, Non-Final Office Action dated Jan. 25, 2019.
U.S. Appl. No. 15/860,174, Notice of Allowance dated Jun. 19, 2019.
U.S. Appl. No. 16/575,755, Requirement for Restriction/Election dated Nov. 12, 2019.
U.S. Appl. No. 16/575,755, Non-Final Office Action dated Apr. 3, 2020.
U.S. Appl. No. 16/575,755, Notice of Allowance dated Oct. 27, 2020.
WIPO Application No. PCT/US2018/012044, PCT Invitation to Pay Additional Fees and, Where Applicable, Protest Fee dated Apr. 30, 2018.
Yu X-Q, et al. 2016. Safety, Tolerability, and Pharmacokinetics of MEDI4893, an Investigational, Extended-Half-Life, Anti-*Staphylococcus aureus* Alpha-Toxin Human Monoclonal Antibody, in Healthy Adults. Antimicrob Agents Chemotherapy. 61:e01020. PMID: 27795368.
U.S. Appl. No. 62/441,786, filed Jan. 3, 2017, Expired.
PCT/US2018/012044, Jan. 2, 2018, WO2018/128973, Expired.
U.S. Appl. No. 15/860,174, filed Jan. 2, 2018, U.S. Pat. No. 10,463,748, Issued.
U.S. Appl. No. 16/575,755, filed Sep. 19, 2019, U.S. Pat. No. 10,940,211, Issued.

* cited by examiner

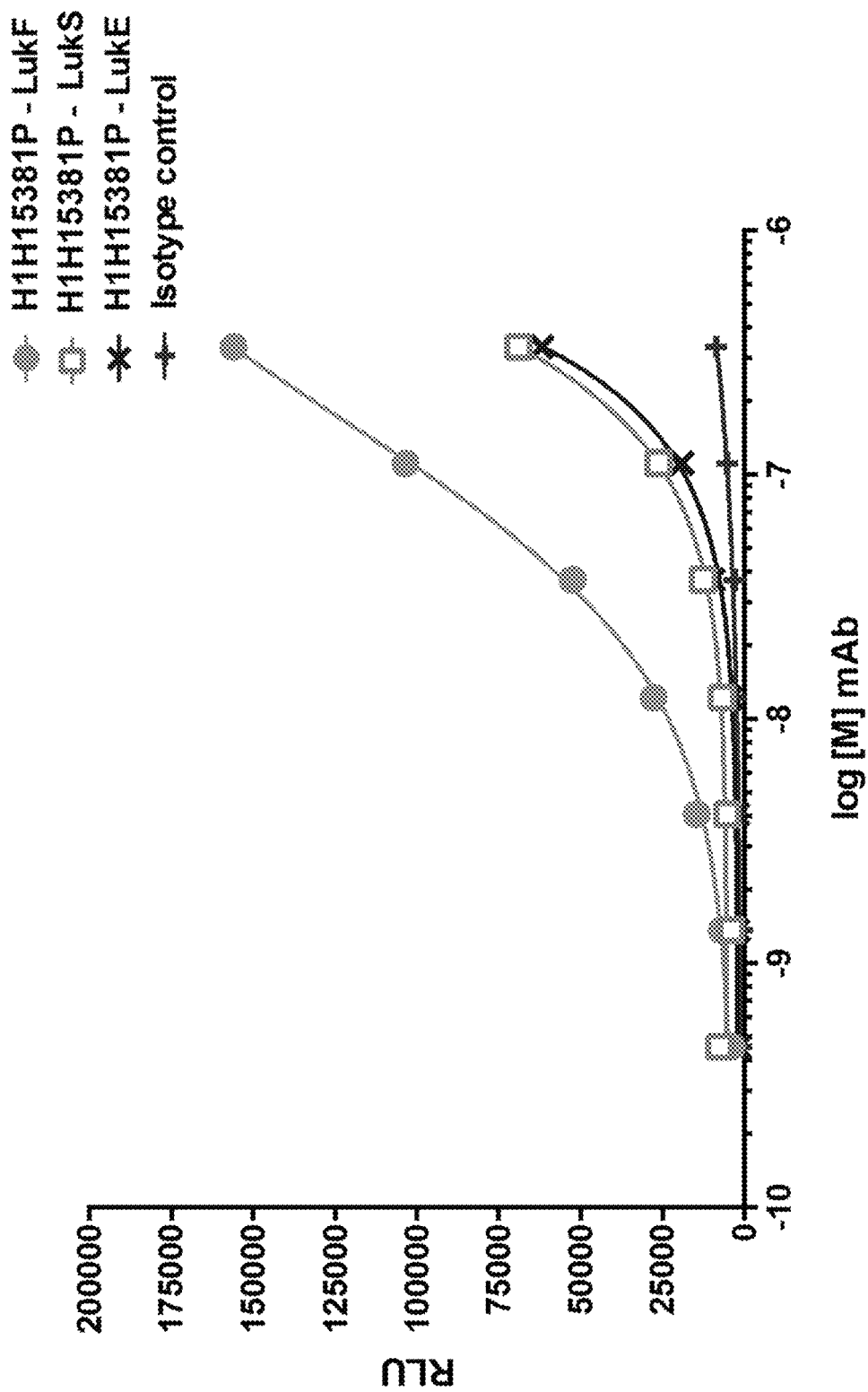

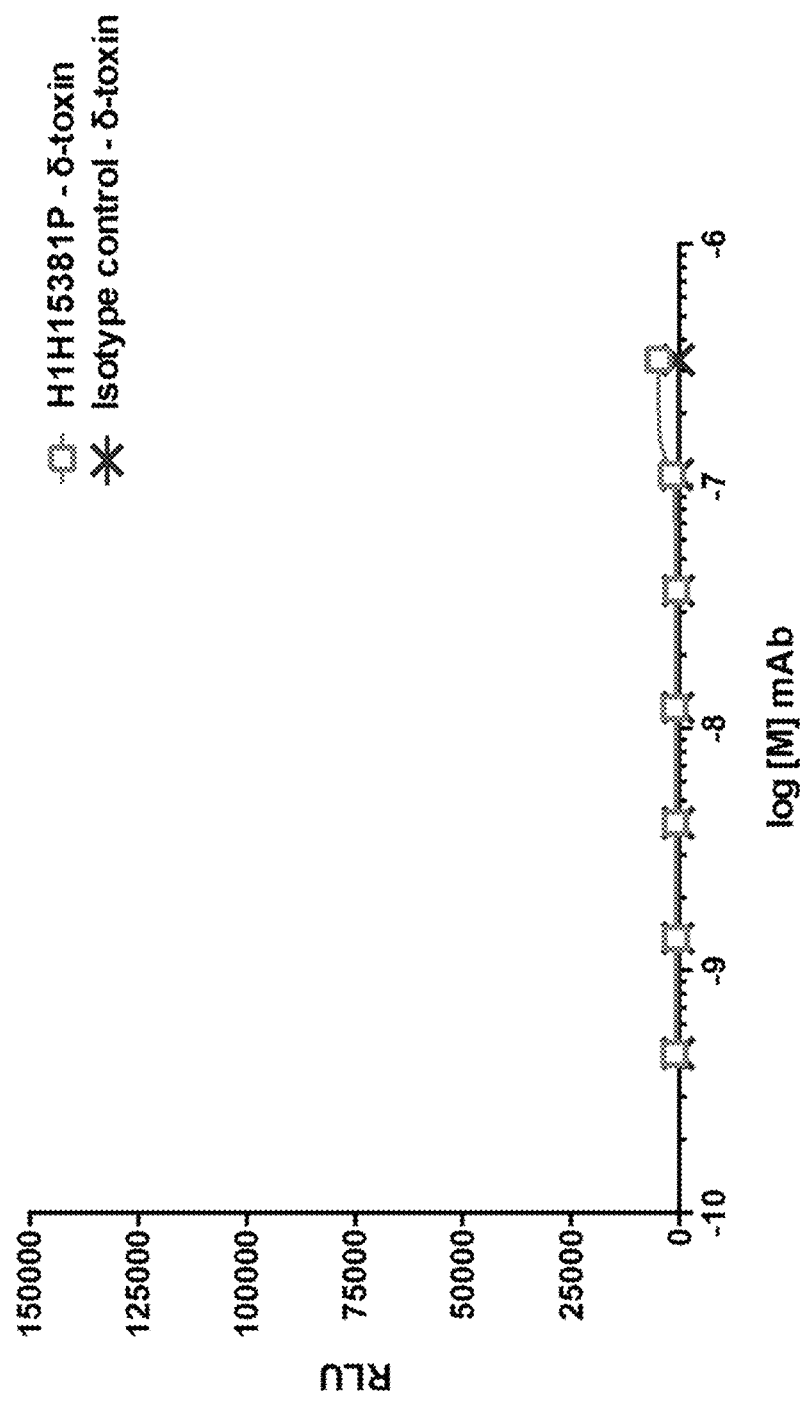

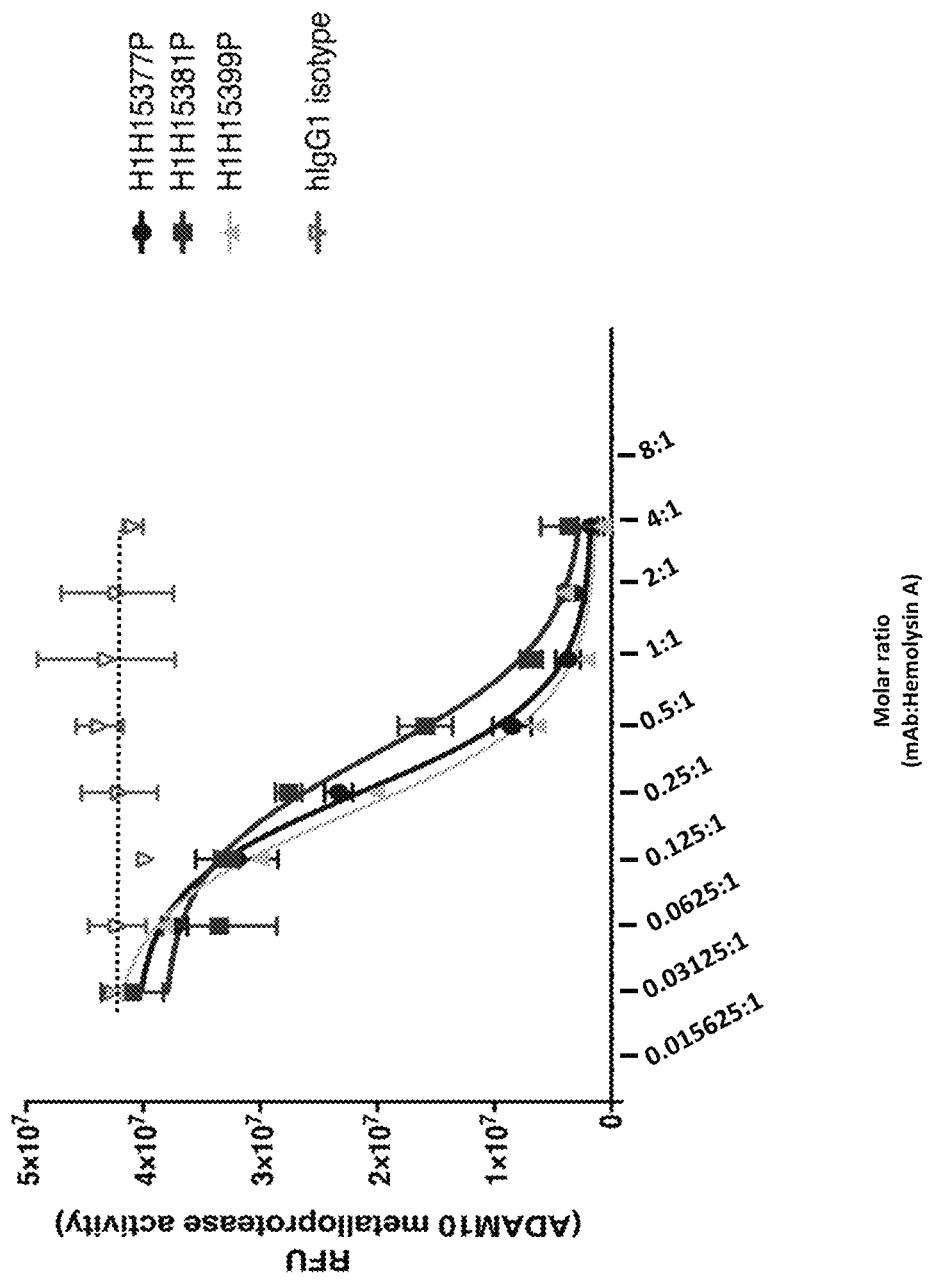

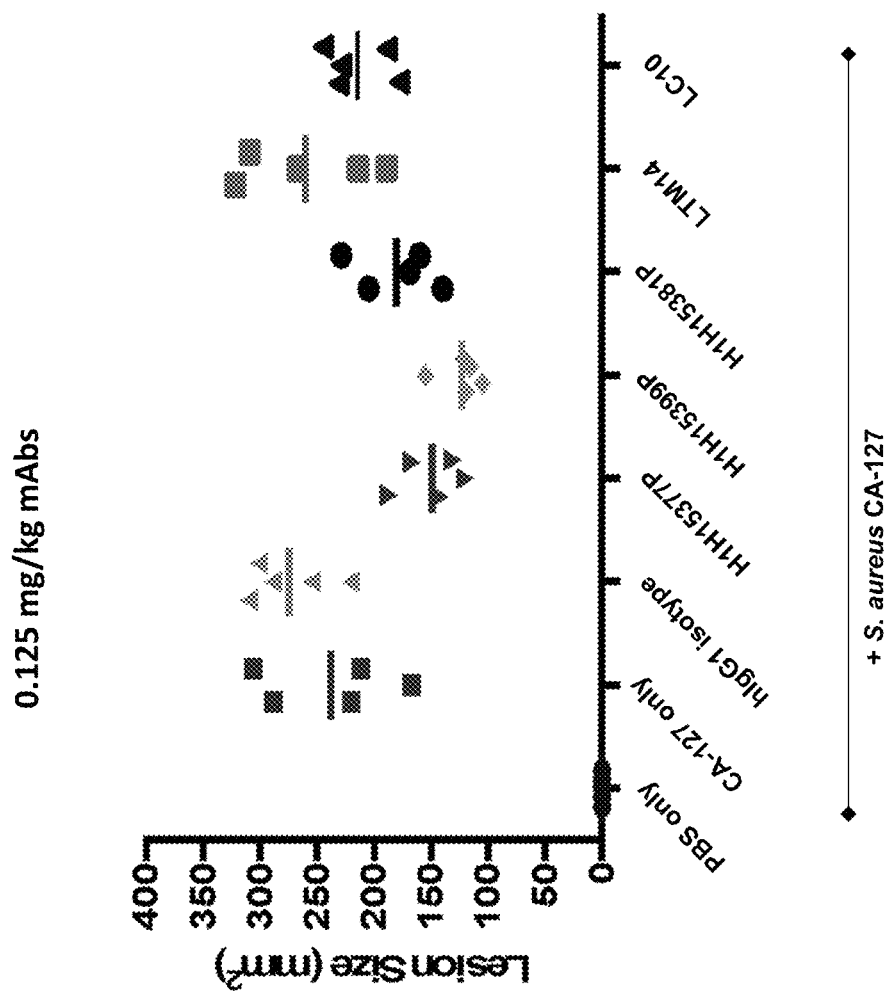

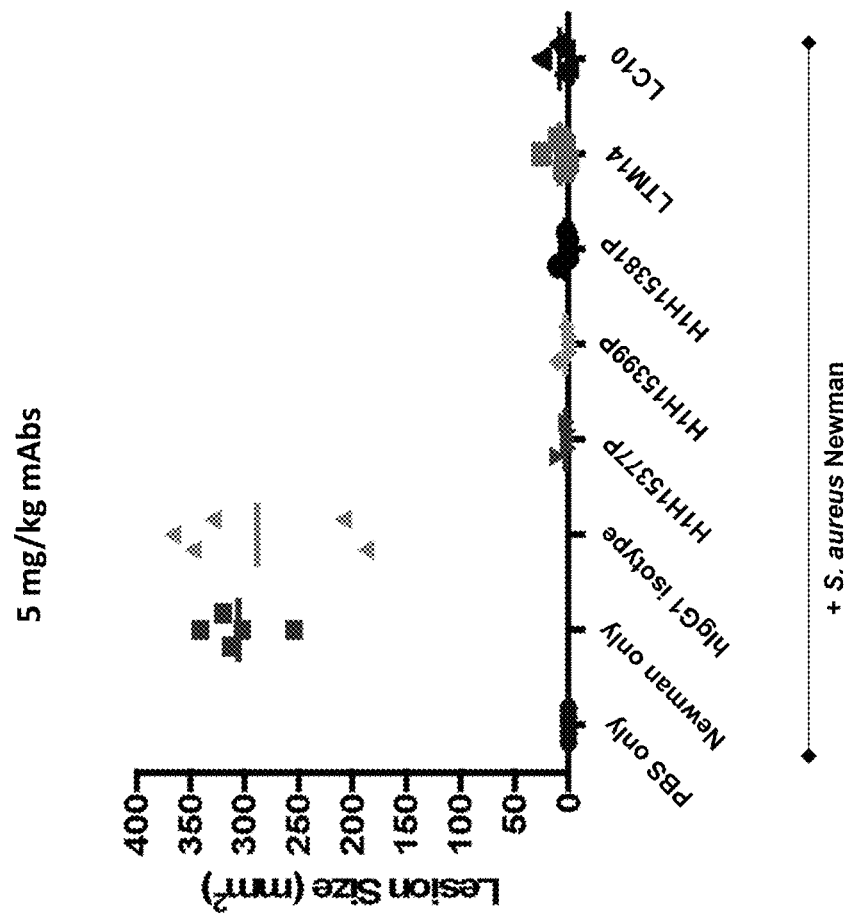

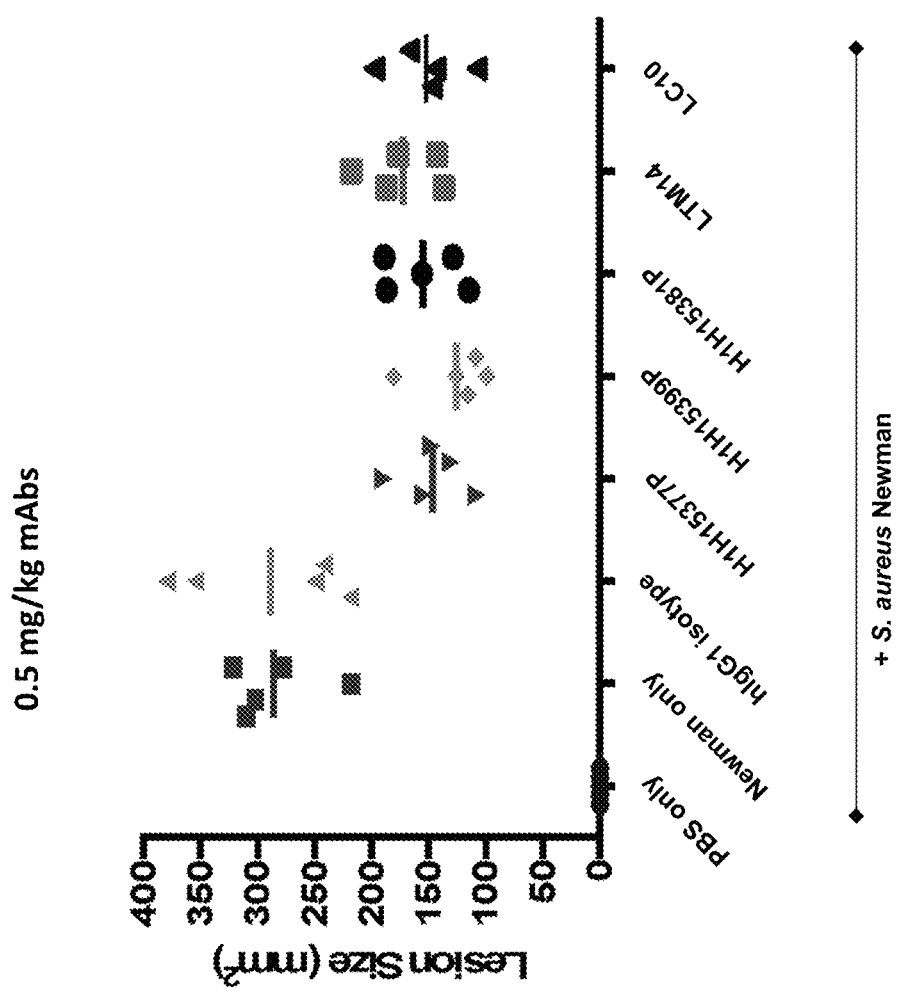

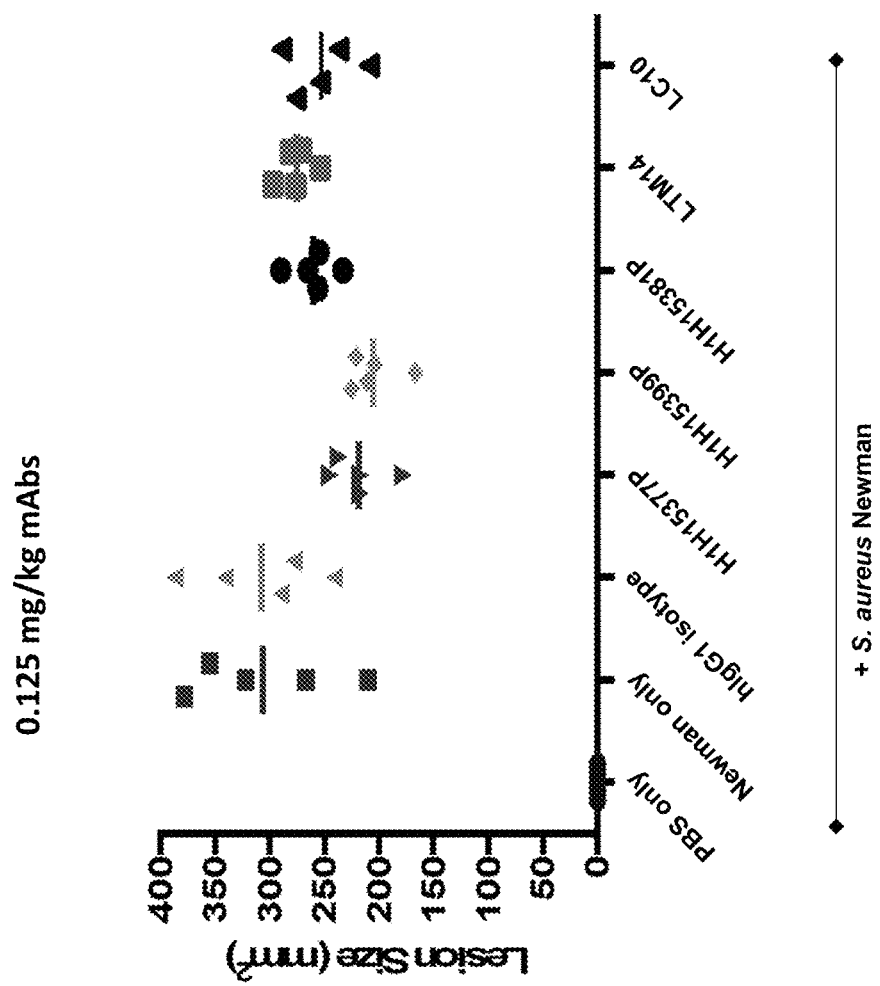

SEQUENCE LISTING

<160> NUMBER OF SEQ ID NOS: 290

<210> SEQ ID NO 1
<211> LENGTH: 375
<212> TYPE: DNA
<213> ORGANISM: Artificial Sequence
<220> FEATURE:
<223> OTHER INFORMATION: Synthetic

<400> SEQUENCE: 1

```
caggtgcagc tggtggagtc tgggggaggc ggggtccagc ctggagggtc cctgagactc      60
tcctgtgaag cgtctggatt cacctttcagt gactatgcca tgcagtgggt ccgccaggct     120
ccaggcaagg ggctggagtg ggtggcagtt atatgggatg atggaagaaa aaaatattat     180
gcagactccg tgaagggccg attcaccgtc tccagagaca actccaagaa cacgctatat     240
ctagaaatta acagcctaag ggtcgaggac acggctgtgt attactgtgc gagagaaggt     300
agtagttcgt ccggacgcta tttcttgtac ggaatggacg tctggggtca agggaccacg     360
gtcaccgtct cctca                                                       375
```

<210> SEQ ID NO 2
<211> LENGTH: 125
<212> TYPE: PRT
<213> ORGANISM: Artificial Sequence
<220> FEATURE:
<223> OTHER INFORMATION: Synthetic

<400> SEQUENCE: 2

```
Gln Val Gln Leu Val Glu Ser Gly Gly Gly Gly Val Gln Pro Gly Arg
1               5                   10                  15

Ser Leu Arg Leu Ser Cys Glu Ala Ser Gly Phe Thr Phe Ser Asp Tyr
```

```
                20                  25                  30
Gly Met Gln Trp Val Arg Gln Ala Pro Gly Lys Gly Leu Glu Trp Val
             35                  40                  45

Ala Val Ile Trp Asp Asp Gly Arg Lys Lys Tyr Tyr Ala Asp Ser Val
     50                  55                  60

Lys Gly Arg Phe Thr Val Ser Arg Asp Asn Ser Lys Asn Thr Leu Tyr
65                  70                  75                  80

Leu Glu Ile Asn Ser Leu Arg Val Glu Asp Thr Ala Val Tyr Tyr Cys
                 85                  90                  95

Ala Arg Glu Gly Ser Ser Ser Gly Arg Tyr Phe Leu Tyr Gly Met
             100                 105                 110

Asp Val Trp Gly Gln Gly Thr Thr Val Thr Val Ser Ser
         115                 120                 125
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcacct tcagtgacta tggc                                          24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser Asp Tyr Gly
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
atatgggatg atggaagaaa aaaa                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Trp Asp Asp Gly Arg Lys Lys
1               5

<210> SEQ ID NO 7
<211> LENGTH: 54
<212> TYPE: DNA
<213> ORGANISM: Artificial Sequence
<220> FEATURE:
<223> OTHER INFORMATION: Synthetic

<400> SEQUENCE: 7

```
gcgagagaag gtagtagttc gtccggacgc tatttcttgt acggaatgga cgtc          54
```

<210> SEQ ID NO 8
<211> LENGTH: 18
<212> TYPE: PRT
<213> ORGANISM: Artificial Sequence
<220> FEATURE:
<223> OTHER INFORMATION: Synthetic

<400> SEQUENCE: 8

Ala Arg Glu Gly Ser Ser Ser Gly Arg Tyr Phe Leu Tyr Gly Met
1               5                   10                  15

Asp Val

<210> SEQ ID NO 9
<211> LENGTH: 324
<212> TYPE: DNA
<213> ORGANISM: Artificial Sequence
<220> FEATURE:
<223> OTHER INFORMATION: Synthetic

<400> SEQUENCE: 9

```
gacatccaga tgacccagtc tccatcctcc ctgtctgcat ctgtaggaga cagagtcacc    60
atcacttgcc gggcaagtca gagaattagc agttatctaa attggtatca acagaaacta   120
gggaaagccc ccaagctcct gatctctgtg gcatccagtt tgcagagtgg ggtcccatca   180
aggttcagtg gcagtggatc tgggacagat ttcactctca ccatcagcag tctgcaacct   240
gaagattttg gaatttatta ctgtcaacag agttacaata cccctccgtg gacgttcggc   300
caagggacca aggtggaaat caaa                                          324
```

<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Ser Tyr
            20                  25                  30

Leu Asn Trp Tyr Gln Gln Lys Leu Gly Lys Ala Pro Lys Leu Leu Ile
        35                  40                  45

Ser Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Ile Tyr Tyr Cys Gln Gln Ser Tyr Asn Thr Pro Pro
                85                  90                  95

Trp Thr Phe Gly Gln Gly Thr Lys Val Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagagaatta gcagttat                                                    18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Arg Ile Ser Ser Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gtggcatcc                                                               9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Val Ala Ser
1

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
caacagagtt acaatacccc tccgtggacg                                        30

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Gln Gln Ser Tyr Asn Thr Pro Pro Trp Thr
1               5                   10

<210> SEQ ID NO 17
<211> LENGTH: 1368
<212> TYPE: DNA
<213> ORGANISM: Artificial Sequence
<220> FEATURE:
<223> OTHER INFORMATION: Synthetic

<400> SEQUENCE: 17
caggtgcagc tggtggagtc tggggggaggc ggggtccagc ctggggaggtc cctgagactc     60

```
tcctgtgaag cgtctggatt caccttcagt gactatggca tgcagtgggt ccgccaggct      120
ccaggcaagg gctggagtg gtggcagtt atatgggatg atggaagaaa aaatattat         180 gcagactccg tgaagggccg attcaccgtc tccagagaca actccaagaa cacgctatat      240
ctagaaatta acagcctaag gtcgaggac acggctgtgt attactgtgc gagagaaggt      300
agtagttcgt ccggacgcta tttcttgtac ggaatggacg tctggggtca agggaccacg      360
gtcaccgtct cctcagcctc caccaagggc ccatcggtct tccccctggc accctcctcc      420
aagagcacct ctgggggcac agcggccctg gctgcctgg tcaaggacta cttccccgaa       480
ccggtgacgg tgtcgtggaa ctcaggcgcc ctgaccagcg gcgtgcacac cttcccggct      540
gtcctacagt cctcaggact ctactccctc agcagcgtgg tgaccgtgcc ctccagcagc      600
ttgggcaccc agacctacat ctgcaacgtg aatcacaagc ccagcaacac caaggtggac     660
aagaaagttg agcccaaatc ttgtgacaaa actcacacat gcccaccgtg cccagcacct     720
gaactcctgg ggggaccgtc agtcttcctc ttccccccaa aacccaagga caccctcatg     780
atctcccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgtgtg gtcagcgtcc tcaccgtcct gcaccaggac     960
tggctgaatg gcaaggagta caagtgcaag gtctccaaca aagccctccc agcccccatc     1020
gagaaaacca tctccaaagc caaagggcag ccccgagaac cacaggtgta caccctgccc     1080
ccatcccggg atgagctgac caagaaccag gtcagcctga cctgcctggt caaaggcttc     1140
tatcccagcg acatcgccgt ggagtgggag agcaatgggc agccggagaa caactacaag     1200
accacgcctc ccgtgctgga ctccgacggc tccttcttcc tctacagcaa gctcaccgtg     1260
gacaagagca ggtggcagca ggggaacgtc ttctcatgct ccgtgatgca tgaggctctg     1320
cacaaccact acacgcagaa gtccctctcc ctgtctccgg gtaaatga                  1368
```

<210> SEQ ID NO 18
<211> LENGTH: 455
<212> TYPE: PRT
<213> ORGANISM: Artificial Sequence
<220> FEATURE:
<223> OTHER INFORMATION: Synthetic

<400> SEQUENCE: 18

```
Gln Val Gln Leu Val Glu Ser Gly Gly Gly Val Gln Pro Gly Arg
1               5                   10                  15

Ser Leu Arg Leu Ser Cys Glu Ala Ser Gly Phe Thr Phe Ser Asp Tyr
            20                  25                  30

Gly Met Gln Trp Val Arg Gln Ala Pro Gly Lys Gly Leu Glu Trp Val
        35                  40                  45

Ala Val Ile Trp Asp Asp Gly Arg Lys Lys Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Glu Ile Asn Ser Leu Arg Val Glu Asp Thr Ala Val Tyr Tyr Cys
                85                  90                  95

Ala Arg Glu Gly Ser Ser Ser Gly Arg Tyr Phe Leu Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
```

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
450                 455

<210> SEQ ID NO 19
<211> LENGTH: 648
<212> TYPE: DNA
<213> ORGANISM: Artificial Sequence
<220> FEATURE:
<223> OTHER INFORMATION: Synthetic

<400> SEQUENCE: 19
gacatccaga tgacccagtc tccatcctcc ctgtctgcat ctgtaggaga cagagtcacc    60
atcacttgcc gggcaagtca gagaattagc agttatctaa attggtatca acagaaacta   120
gggaaagccc ccaagctcct gatctctgtg catccagtt tgcagagtgg ggtcccatca   180
aggttcagtg gcagtggatc tgggacagat ttcactctca ccatcagcag tctgcaacct   240

```
gaagattttg gaatttatta ctgtcaacag agttacaata cccctccgtg gacgttcggc      300
caagggacca aggtggaaat caaacgaact gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacaggggag agtgttag                   648
```

<210> SEQ ID NO 20
<211> LENGTH: 215
<212> TYPE: PRT
<213> ORGANISM: Artificial Sequence
<220> FEATURE:
<223> OTHER INFORMATION: Synthetic

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Ser Tyr
            20                  25                  30

Leu Asn Trp Tyr Gln Gln Lys Leu Gly Lys Ala Pro Lys Leu Leu Ile
        35                  40                  45

Ser Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Ile Tyr Tyr Cys Gln Gln Ser Tyr Asn Thr Pro Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 21
<211> LENGTH: 399
<212> TYPE: DNA
<213> ORGANISM: Artificial Sequence
<220> FEATURE:
<223> OTHER INFORMATION: Synthetic

<400> SEQUENCE: 21

```
caggtacagc tgcagcagtc aggtccagga ctggtgaagc cctcgcagac cctctcactc       60
```

```
acctgtgcca tatccggtga cagtgtcgct agcaacaatg ctgcttggaa ctggatcagg    120
cagtccccat cgagaggcct tgagtggctg ggaaggacat actacaggtc caagtggttt    180
aatgattacg tagaatctgt gaaaagtcga ataagtttca acccagacac atccaagaac    240
cagttctccc tgcagctgaa ctctgtgact cccgaggaca cggctgtgta ttattgcgca    300
cgttcgtact atgattttg gagtggttat tctgagaata actactactt ctacggtatg    360
gacgtctggg gccaagggac cacggtcacc gtctcctca                          399
```

```
<210> SEQ ID NO 22
<211> LENGTH: 133
<212> TYPE: PRT
<213> ORGANISM: Artificial Sequence
<220> FEATURE:
<223> OTHER INFORMATION: Synthetic

<400> SEQUENCE: 22
```

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ala Ser Asn
            20                  25                  30

Asn Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Phe Asn Asp Tyr Val
    50                  55                  60

Glu Ser Val Lys Ser Arg Ile Ser Phe Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Tyr Tyr Asp Phe Trp Ser Gly Tyr Ser Glu
            100                 105                 110

Asn Asn Tyr Tyr Phe Tyr Gly Met Asp Val Trp Gly Gln Gly Thr Thr
        115                 120                 125

Val Thr Val Ser Ser
    130

```
<210> SEQ ID NO 23
<211> LENGTH: 30
<212> TYPE: DNA
<213> ORGANISM: Artificial Sequence
<220> FEATURE:
<223> OTHER INFORMATION: Synthetic

<400> SEQUENCE: 23
ggtgacagtg tcgctagcaa caatgctgct                                     30
```

```
<210> SEQ ID NO 24
<211> LENGTH: 10
<212> TYPE: PRT
<213> ORGANISM: Artificial Sequence
<220> FEATURE:
<223> OTHER INFORMATION: Synthetic

<400> SEQUENCE: 24
```

Gly Asp Ser Val Ala Ser Asn Asn Ala Ala
1               5                   10

```
<210> SEQ ID NO 25
<211> LENGTH: 27
<212> TYPE: DNA
<213> ORGANISM: Artificial Sequence
```

<220> FEATURE:
<223> OTHER INFORMATION: Synthetic

<400> SEQUENCE: 25
acatactaca ggtccaagtg gtttaat                                27

<210> SEQ ID NO 26
<211> LENGTH: 9
<212> TYPE: PRT
<213> ORGANISM: Artificial Sequence
<220> FEATURE:
<223> OTHER INFORMATION: Synthetic

<400> SEQUENCE: 26

Thr Tyr Tyr Arg Ser Lys Trp Phe Asn
1               5

<210> SEQ ID NO 27
<211> LENGTH: 69
<212> TYPE: DNA
<213> ORGANISM: Artificial Sequence
<220> FEATURE:
<223> OTHER INFORMATION: Synthetic

<400> SEQUENCE: 27
gcacgttcgt actatgattt ttggagtggt tattctgaga ataactacta cttctacggt    60
atggacgtc                                                           69

<210> SEQ ID NO 28
<211> LENGTH: 23
<212> TYPE: PRT
<213> ORGANISM: Artificial Sequence
<220> FEATURE:
<223> OTHER INFORMATION: Synthetic

<400> SEQUENCE: 28

Ala Arg Ser Tyr Tyr Asp Phe Trp Ser Gly Tyr Ser Glu Asn Asn Tyr
1               5                   10                  15

Tyr Phe Tyr Gly Met Asp Val
            20

<210> SEQ ID NO 29
<211> LENGTH: 321
<212> TYPE: DNA
<213> ORGANISM: Artificial Sequence
<220> FEATURE:
<223> OTHER INFORMATION: Synthetic

<400> SEQUENCE: 29
gacatccaga tgacccagtc tccatcctcc ctgtctgcat ctgtaggaga cagagtctcc    60
atcacttgcc ggacaagtca gggcattaga aatgatttag gctggtatca gcagaaacca   120
gggaaagccc ctaagcgcct gatctatgct gcatccagtt acaaagtggg gtcccatca    180 aggttcagcg gcagtggatc tgggacagaa ttcactctca caatcagcag cctgcagcct   240
gaagattttg caacttatta ctgtctacaa cataatattt accctccgac gttcggccaa   300
gggaccaagg tggaaatcaa a                                             321

<210> SEQ ID NO 30
<211> LENGTH: 107
<212> TYPE: PRT
<213> ORGANISM: Artificial Sequence
<220> FEATURE:
<223> OTHER INFORMATION: Synthetic

```
<400> SEQUENCE: 30

Asp Ile Gln Met Thr Gln Ser Pro Ser Ser Leu Ser Ala Ser Val Gly
1               5                   10                  15

Asp Arg Val Ser Ile Thr Cys Arg Thr Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ile Tyr Pro Pro
                85                  90                  95

Thr Phe Gly Gln Gly Thr Lys Val Glu Ile Lys
            100                 105

<210> SEQ ID NO 31
<211> LENGTH: 18
<212> TYPE: DNA
<213> ORGANISM: Artificial Sequence
<220> FEATURE:
<223> OTHER INFORMATION: Synthetic

<400> SEQUENCE: 31
cagggcatta gaaatgat                                              18

<210> SEQ ID NO 32
<211> LENGTH: 6
<212> TYPE: PRT
<213> ORGANISM: Artificial Sequence
<220> FEATURE:
<223> OTHER INFORMATION: Synthetic

<400> SEQUENCE: 32

Gln Gly Ile Arg Asn Asp
1               5

<210> SEQ ID NO 33
<211> LENGTH: 9
<212> TYPE: DNA
<213> ORGANISM: Artificial Sequence
<220> FEATURE:
<223> OTHER INFORMATION: Synthetic

<400> SEQUENCE: 33 gctgcatcc                                                         9

<210> SEQ ID NO 34
<211> LENGTH: 3
<212> TYPE: PRT
<213> ORGANISM: Artificial Sequence
<220> FEATURE:
<223> OTHER INFORMATION: Synthetic

<400> SEQUENCE: 34

Ala Ala Ser
1

<210> SEQ ID NO 35
<211> LENGTH: 27
<212> TYPE: DNA
<213> ORGANISM: Artificial Sequence
```

```
<220> FEATURE:
<223> OTHER INFORMATION: Synthetic

<400> SEQUENCE: 35
ctacaacata atatttaccc tccgacg                                             27

<210> SEQ ID NO 36
<211> LENGTH: 9
<212> TYPE: PRT
<213> ORGANISM: Artificial Sequence
<220> FEATURE:
<223> OTHER INFORMATION: Synthetic

<400> SEQUENCE: 36

Leu Gln His Asn Ile Tyr Pro Pro Thr
1               5

<210> SEQ ID NO 37
<211> LENGTH: 1392
<212> TYPE: DNA
<213> ORGANISM: Artificial Sequence
<220> FEATURE:
<223> OTHER INFORMATION: Synthetic

<400> SEQUENCE: 37
caggtacagc tgcagcagtc aggtccagga ctggtgaagc cctcgcagac cctctcactc           60
acctgtgcca tatccggtga cagtgtcgct agcaacaatg ctgcttggaa ctggatcagg          120
cagtccccat cgagaggcct gagtggctg ggaaggacat actacaggtc caagtggttt          180
aatgattacg tagaatctgt gaaaagtcga ataagtttca acccagacac atccaagaac          240
cagttctccc tgcagctgaa ctctgtgact cccgaggaca cggctgtgta ttattgcgca          300
cgttcgtact atgattttg gagtggttat tctgagaata actactactt ctacggtatg          360
gacgtctggg gccaagggac cacggtcacc gtctcctcag cctccaccaa gggcccatcg          420
gtcttccccc tggcaccctc ctccaagagc acctctgggg gcacagcggc cctgggctgc          480
ctggtcaagg actacttccc cgaaccggtg acggtgtcgt ggaactcagg cgccctgacc          540
agcggcgtgc acaccttccc ggctgtccta cagtcctcag gactctactc cctcagcagc          600
gtggtgaccg tgccctccag cagcttgggc acccagacct acatctgcaa cgtgaatcac          660
aagcccagca acaccaaggt ggacaagaaa gttgagccca aatcttgtga caaaactcac          720
acatgcccac cgtgcccagc acctgaactc ctggggggac cgtcagtctt cctcttcccc          780
ccaaaaccca aggacaccct catgatctcc cggacccctg aggtcacatg cgtggtggtg          840
gacgtgagcc acgaagaccc tgaggtcaag ttcaactggt acgtggacgg cgtggaggtg          900
cataatgcca agacaaagcc gcgggaggag cagtacaaca gcacgtaccg tgtggtcagc          960
gtcctcaccg tcctgcacca ggactggctg aatggcaagg agtacaagtg caaggtctcc         1020
aacaaagccc tcccagcccc catcgagaaa accatctcca agccaaaggg cagccccga         1080 gaaccacagg tgtacaccct gcccccatcc cgggatgagc tgaccaagaa ccaggtcagc         1140
ctgacctgcc tggtcaaagg cttctatccc agcgacatcg ccgtggagtg ggagagcaat         1200
gggcagccgg agaacaacta caagaccacg cctcccgtgc tggactccga cggctccttc         1260
ttcctctaca gcaagctcac cgtggacaag agcaggtggc agcaggggaa cgtcttctca         1320
tgctccgtga tgcatgaggc tctgcacaac cactacacgc agaagtccct ctccctgtct         1380
ccgggtaaat ga                                                             1392
```

<210> SEQ ID NO 38
<211> LENGTH: 463
<212> TYPE: PRT
<213> ORGANISM: Artificial Sequence
<220> FEATURE:
<223> OTHER INFORMATION: Synthetic

<400> SEQUENCE: 38

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ala Ser Asn
            20                  25                  30

Asn Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Phe Asn Asp Tyr Val
    50                  55                  60

Glu Ser Val Lys Ser Arg Ile Ser Phe Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Tyr Tyr Asp Phe Trp Ser Gly Tyr Ser Glu
            100                 105                 110

Asn Asn Tyr Tyr Phe Tyr Gly Met Asp Val Trp Gly Gln Gly Thr Thr
        115                 120                 125

Val Thr Val Ser Ser Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Asp Glu Leu Thr Lys Asn Gln Val Ser Leu Thr Cys Leu
```

```
                370               375               380
Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
                435                 440                 445

His Asn His Tyr Thr Gln Lys Ser Leu Ser Leu Ser Pro Gly Lys
    450                 455                 460
```

<210> SEQ ID NO 39
<211> LENGTH: 645
<212> TYPE: DNA
<213> ORGANISM: Artificial Sequence
<220> FEATURE:
<223> OTHER INFORMATION: Synthetic

<400> SEQUENCE: 39

```
gacatccaga tgacccagtc tccatcctcc ctgtctgcat ctgtaggaga cagagtctcc    60
atcacttgcc ggacaagtca gggcattaga aatgatttag gctggtatca gcagaaacca   120
gggaaagccc ctaagcgcct gatctatgct gcatccagtt tacaaagtgg ggtcccatca   180
aggttcagcg gcagtggatc tgggacagaa ttcactctca caatcagcag cctgcagcct   240
gaagattttg caacttatta ctgtctacaa cataatattt accctccgac gttcggccaa   300
gggaccaagg tggaaatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                   645
```

<210> SEQ ID NO 40
<211> LENGTH: 214
<212> TYPE: PRT
<213> ORGANISM: Artificial Sequence
<220> FEATURE:
<223> OTHER INFORMATION: Synthetic

<400> SEQUENCE: 40

```
Asp Ile Gln Met Thr Gln Ser Pro Ser Ser Leu Ser Ala Ser Val Gly
1               5                   10                  15

Asp Arg Val Ser Ile Thr Cys Arg Thr Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ile Tyr Pro Pro
                85                  90                  95

Thr Phe Gly Gln Gly Thr Lys Val Glu Ile Lys Arg Thr Val Ala Ala
                100                 105                 110
```

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 41
<211> LENGTH: 354
<212> TYPE: DNA
<213> ORGANISM: Artificial Sequence
<220> FEATURE:
<223> OTHER INFORMATION: Synthetic

<400> SEQUENCE: 41
gaggtgcagc tggtggagtc tgggggaggc ttggtacagc ctggagggtc cctgagactc    60
tcctgtgcag cctctggatt caccttract agttatgaaa tgaattgggt ccgccaggct   120
ccagggaagg gcctggagtg gattcatac attagtagtg gtggtgatac caaatactac   180
gcagactctg tgaggggccg attcaccatc tccagagaca acgccaagaa ctcactatat   240
ctgcaaatga acagcctgag agccgaggac acggctcttt attactgtgc gagagatgtc   300
ctcaattggg tctttgatta ttggggccgg ggaaccctgg tcaccgtctc ctca         354

<210> SEQ ID NO 42
<211> LENGTH: 118
<212> TYPE: PRT
<213> ORGANISM: Artificial Sequence
<220> FEATURE:
<223> OTHER INFORMATION: Synthetic

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Glu Met Asn Trp Val Arg Gln Ala Pro Gly Lys Gly Leu Glu Trp Ile
        35                  40                  45

Ser Tyr Ile Ser Ser Gly Gly Asp Thr Lys Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Val Leu Asn Trp Val Phe Asp Tyr Trp Gly Arg Gly Thr
            100                 105                 110

Leu Val Thr Val Ser Ser
        115

<210> SEQ ID NO 43
<211> LENGTH: 24
<212> TYPE: DNA
<213> ORGANISM: Artificial Sequence
<220> FEATURE:
<223> OTHER INFORMATION: Synthetic

<400> SEQUENCE: 43
ggattcacct ttactagtta tgaa 24

<210> SEQ ID NO 44
<211> LENGTH: 8
<212> TYPE: PRT
<213> ORGANISM: Artificial Sequence
<220> FEATURE:
<223> OTHER INFORMATION: Synthetic

<400> SEQUENCE: 44

Gly Phe Thr Phe Thr Ser Tyr Glu
1               5

<210> SEQ ID NO 45
<211> LENGTH: 24
<212> TYPE: DNA
<213> ORGANISM: Artificial Sequence
<220> FEATURE:
<223> OTHER INFORMATION: Synthetic

<400> SEQUENCE: 45
attagtagtg gtggtgatac caaa 24

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

Ile Ser Ser Gly Gly Asp Thr Lys
1               5

<210> SEQ ID NO 47
<211> LENGTH: 33
<212> TYPE: DNA
<213> ORGANISM: Artificial Sequence
<220> FEATURE:
<223> OTHER INFORMATION: Synthetic

<400> SEQUENCE: 47
gcgagagatg tcctcaattg ggtctttgat tat 33

<210> SEQ ID NO 48
<211> LENGTH: 11
<212> TYPE: PRT
<213> ORGANISM: Artificial Sequence
<220> FEATURE:
<223> OTHER INFORMATION: Synthetic

<400> SEQUENCE: 48

Ala Arg Asp Val Leu Asn Trp Val Phe Asp Tyr
1               5                   10

<210> SEQ ID NO 49
<211> LENGTH: 321
<212> TYPE: DNA
<213> ORGANISM: Artificial Sequence
<220> FEATURE:
<223> OTHER INFORMATION: Synthetic

<400> SEQUENCE: 49

```
gacatccaga tgacccagtc tccatcctcc ctgtctgcat ctgttggaga cagagtcacc    60
atcacttgcc gggcaagtca gagcattgga aaatatttaa attggtatcg cagagtcca   120
gggaaagccc ctaaactcct aatctatgca acatccagtt tgcaaagtgg ggtcccatca   180
agtttcagtg gcagtggatc tgggacagat ttcactctca ccatcagcag tctgcaacct   240
gaagattttg caacttacta ctgtcaacag ggtttcagaa ccccattcac tttcggccct   300
gggaccaaag tggatatcaa a                                             321
```

<210> SEQ ID NO 50
<211> LENGTH: 107
<212> TYPE: PRT
<213> ORGANISM: Artificial Sequence
<220> FEATURE:
<223> OTHER INFORMATION: Synthetic

<400> SEQUENCE: 50

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Gly Lys Tyr
            20                  25                  30
Leu Asn Trp Tyr Arg Gln Ser Pro Gly Lys Ala Pro Lys Leu Leu Ile
        35                  40                  45
Tyr Ala Thr Ser Ser Leu Gln Ser Gly Val Pro Ser Ser Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Phe Arg Thr Pro Phe
                85                  90                  95
Thr Phe Gly Pro Gly Thr Lys Val Asp Ile Lys
            100                 105
```

<210> SEQ ID NO 51
<211> LENGTH: 18
<212> TYPE: DNA
<213> ORGANISM: Artificial Sequence
<220> FEATURE:
<223> OTHER INFORMATION: Synthetic

<400> SEQUENCE: 51

```
cagagcattg gaaaatat                                                  18
```

<210> SEQ ID NO 52
<211> LENGTH: 6
<212> TYPE: PRT
<213> ORGANISM: Artificial Sequence
<220> FEATURE:
<223> OTHER INFORMATION: Synthetic

<400> SEQUENCE: 52

```
Gln Ser Ile Gly Lys Tyr
1               5
```

<210> SEQ ID NO 53
<211> LENGTH: 9
<212> TYPE: DNA
<213> ORGANISM: Artificial Sequence
<220> FEATURE:

<210> SEQ ID NO 54
<211> LENGTH: 3
<212> TYPE: PRT
<213> ORGANISM: Artificial Sequence
<220> FEATURE:
<223> OTHER INFORMATION: Synthetic

<400> SEQUENCE: 53 gcaacatcc                                                                 9

<210> SEQ ID NO 54
<211> LENGTH: 3
<212> TYPE: PRT
<213> ORGANISM: Artificial Sequence
<220> FEATURE:
<223> OTHER INFORMATION: Synthetic

<400> SEQUENCE: 54

Ala Thr Ser
1

<210> SEQ ID NO 55
<211> LENGTH: 27
<212> TYPE: DNA
<213> ORGANISM: Artificial Sequence
<220> FEATURE:
<223> OTHER INFORMATION: Synthetic

<400> SEQUENCE: 55
caacagggtt tcagaacccc attcact                                            27

<210> SEQ ID NO 56
<211> LENGTH: 9
<212> TYPE: PRT
<213> ORGANISM: Artificial Sequence
<220> FEATURE:
<223> OTHER INFORMATION: Synthetic

<400> SEQUENCE: 56

Gln Gln Gly Phe Arg Thr Pro Phe Thr
1               5

<210> SEQ ID NO 57
<211> LENGTH: 1347
<212> TYPE: DNA
<213> ORGANISM: Artificial Sequence
<220> FEATURE:
<223> OTHER INFORMATION: Synthetic

<400> SEQUENCE: 57
gaggtgcagc tggtggagtc tgggggaggc ttggtacagc ctggagggtc cctgagactc        60
tcctgtgcag cctctggatt cacctttact agttatgaaa tgaattgggt ccgccaggct       120
ccagggaagg gcctggagtg gatttcatac attagtagtg gtggtgatac caaatactac       180
gcagactctg tgaggggccg attcaccatc tccagagaca cgccaagaa ctcactatat       240 ctgcaaatga acagcctgag agccgaggac acggctcttt attactgtgc gagagatgtc       300
ctcaattggg tctttgatta ttggggccgg ggaaccctgg tcaccgtctc ctcagcctcc       360
accaagggcc catcggtctt ccccctggca ccctcctcca gagcacctc tgggggcaca       420 gcggccctgg gctgcctggt caaggactac ttccccgaac cggtgacggt gtcgtggaac       480
tcaggcgccc tgaccagcgg cgtgcacacc ttccgcctg tcctacagtc ctcaggactc       540
tactccctca gcagcgtggt gaccgtgccc tccagcagct gggcaccca gacctacatc       600 tgcaacgtga atcacaagcc cagcaacacc aaggtggaca agaaagttga gcccaaatct       660
tgtgacaaaa ctcacacatg cccaccgtgc ccagcacctg aactcctggg gggaccgtca       720
gtcttcctct tccccccaaa acccaaggac accctcatga tctcccggac ccctgaggtc       780

```
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga tgagctgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
tccctctccc tgtctccggg taaatga                                      1347
```

<210> SEQ ID NO 58
<211> LENGTH: 448
<212> TYPE: PRT
<213> ORGANISM: Artificial Sequence
<220> FEATURE:
<223> OTHER INFORMATION: Synthetic

<400> SEQUENCE: 58

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Glu Met Asn Trp Val Arg Gln Ala Pro Gly Lys Gly Leu Glu Trp Ile
        35                  40                  45

Ser Tyr Ile Ser Ser Gly Gly Asp Thr Lys Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Val Leu Asn Trp Val Phe Asp Tyr Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 59
<211> LENGTH: 645
<212> TYPE: DNA
<213> ORGANISM: Artificial Sequence
<220> FEATURE:
<223> OTHER INFORMATION: Synthetic

<400> SEQUENCE: 59
gacatccaga tgacccagtc tccatcctcc ctgtctgcat ctgttggaga cagagtcacc      60
atcacttgcc gggcaagtca gagcattgga aaatatttaa attggtatcg cagagtcca     120
gggaaagccc ctaaactcct aatctatgca acatccagtt tgcaaagtgg ggtcccatca    180
agtttcagtg gcagtggatc tgggacagat ttcactctca ccatcagcag tctgcaacct    240
gaagattttg caacttacta ctgtcaacag ggtttcagaa ccccattcac tttcggccct    300
gggaccaaag tggatatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                     645

<210> SEQ ID NO 60
<211> LENGTH: 214
<212> TYPE: PRT
<213> ORGANISM: Artificial Sequence
<220> FEATURE:
<223> OTHER INFORMATION: Synthetic

<400> SEQUENCE: 60

Asp Ile Gln Met Thr Gln Ser Pro Ser Ser Leu Ser Ala Ser Val Gly

```
            1               5                  10                 15
Asp Arg Val Thr Ile Thr Cys Arg Ala Ser Gln Ser Ile Gly Lys Tyr
                20                 25                 30

Leu Asn Trp Tyr Arg Gln Ser Pro Gly Lys Ala Pro Lys Leu Leu Ile
                35                 40                 45

Tyr Ala Thr Ser Ser Leu Gln Ser Gly Val Pro Ser Phe Ser Gly
            50                 55                 60

Ser Gly Ser Gly Thr Asp Phe Thr Leu Thr Ile Ser Ser Leu Gln Pro
65                  70                 75                 80

Glu Asp Phe Ala Thr Tyr Tyr Cys Gln Gln Gly Phe Arg Thr Pro Phe
                85                 90                 95

Thr Phe Gly Pro Gly Thr Lys Val Asp Ile Lys Arg Thr Val Ala Ala
                100                105                110

Pro Ser Val Phe Ile Phe Pro Pro Ser Asp Glu Gln Leu Lys Ser Gly
                115                120                125

Thr Ala Ser Val Val Cys Leu Leu Asn Asn Phe Tyr Pro Arg Glu Ala
            130                135                140

Lys Val Gln Trp Lys Val Asp Asn Ala Leu Gln Ser Gly Asn Ser Gln
145                 150                155                160

Glu Ser Val Thr Glu Gln Asp Ser Lys Asp Ser Thr Tyr Ser Leu Ser
                165                170                175

Ser Thr Leu Thr Leu Ser Lys Ala Asp Tyr Glu Lys His Lys Val Tyr
            180                185                190

Ala Cys Glu Val Thr His Gln Gly Leu Ser Ser Pro Val Thr Lys Ser
            195                200                205

Phe Asn Arg Gly Glu Cys
    210
```

<210> SEQ ID NO 61
<211> LENGTH: 363
<212> TYPE: DNA
<213> ORGANISM: Artificial Sequence
<220> FEATURE:
<223> OTHER INFORMATION: Synthetic

<400> SEQUENCE: 61

```
gaggtgcagc tggtggagtc tgggggaggc ttggtacagc ctggagggtc cctgagactc      60
tcctgtgcag cctctggatt caccttcaat aattatgaaa tgaactgggt ccgccaggct     120
ccagggaagg ggctggagtg gtatcattc attagtagta gtggtagtac catagactac     180
gcagtctctg tgaagggccg attcaccatc tccagagaca cgccaagaa ctcactgtat     240 ctgcaaatga acagcctgag acccggggac acggctgttt attactgtgc gagagcccgg     300
ctagacttct attattacgg tatggacgtc tggggccaag ggaccacggt caccgtctcc     360
tca                                                                   363
```

<210> SEQ ID NO 62
<211> LENGTH: 121
<212> TYPE: PRT
<213> ORGANISM: Artificial Sequence
<220> FEATURE:
<223> OTHER INFORMATION: Synthetic

<400> SEQUENCE: 62

```
Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Thr Phe Asn Asn Tyr
```

```
            20                  25                  30
Glu Met Asn Trp Val Arg Gln Ala Pro Gly Lys Gly Leu Glu Trp Val
            35                  40                  45

Ser Phe Ile Ser Ser Ser Gly Ser Thr Ile Asp Tyr Ala Val Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Pro Gly Asp Thr Ala Val Tyr Tyr Cys
                85                  90                  95

Ala Arg Ala Arg Leu Asp Phe Tyr Tyr Tyr Gly Met Asp Val Trp Gly
            100                 105                 110

Gln Gly Thr Thr Val Thr Val Ser Ser
            115                 120
```

<210> SEQ ID NO 63
<211> LENGTH: 24
<212> TYPE: DNA
<213> ORGANISM: Artificial Sequence
<220> FEATURE:
<223> OTHER INFORMATION: Synthetic

<400> SEQUENCE: 63
ggattcacct tcaataatta tgaa                                    24

<210> SEQ ID NO 64
<211> LENGTH: 8
<212> TYPE: PRT
<213> ORGANISM: Artificial Sequence
<220> FEATURE:
<223> OTHER INFORMATION: Synthetic

<400> SEQUENCE: 64

```
Gly Phe Thr Phe Asn Asn Tyr Glu
 1               5
```

<210> SEQ ID NO 65
<211> LENGTH: 24
<212> TYPE: DNA
<213> ORGANISM: Artificial Sequence
<220> FEATURE:
<223> OTHER INFORMATION: Synthetic

<400> SEQUENCE: 65
attagtagta gtggtagtac cata                                    24

<210> SEQ ID NO 66
<211> LENGTH: 8
<212> TYPE: PRT
<213> ORGANISM: Artificial Sequence
<220> FEATURE:
<223> OTHER INFORMATION: Synthetic

<400> SEQUENCE: 66

```
Ile Ser Ser Ser Gly Ser Thr Ile
 1               5
```

<210> SEQ ID NO 67
<211> LENGTH: 42
<212> TYPE: DNA
<213> ORGANISM: Artificial Sequence
<220> FEATURE:
<223> OTHER INFORMATION: Synthetic

<400> SEQUENCE: 67
gcgagagccc ggctagactt ctattattac ggtatggacg tc        42

<210> SEQ ID NO 68
<211> LENGTH: 14
<212> TYPE: PRT
<213> ORGANISM: Artificial Sequence
<220> FEATURE:
<223> OTHER INFORMATION: Synthetic

<400> SEQUENCE: 68

Ala Arg Ala Arg Leu Asp Phe Tyr Tyr Tyr Gly Met Asp Val
1               5                   10

<210> SEQ ID NO 69
<211> LENGTH: 321
<212> TYPE: DNA
<213> ORGANISM: Artificial Sequence
<220> FEATURE:
<223> OTHER INFORMATION: Synthetic

<400> SEQUENCE: 69
gacatccaga tgacccagtc tccatcctca ctgtctgcat ctgttggaga cagagtcacc     60
atcacttgtc gggcgagtca gggcattagc aattatttag cctggtttca gcagaagcca    120
gggaaagccc ctaagtccct gatctatgct acatccactt tgcaaagtgg ggtcccatca    180
aagttcagcg gcagtggatc tgggacagat ttcactctca ccatcagcag cctgcagcct    240
gaagattttg caacgtatta ctgccaacag tataatagtt cccgctcac tttcggcgga    300 gggaccaagg tggagatcaa a                                              321

<210> SEQ ID NO 70
<211> LENGTH: 107
<212> TYPE: PRT
<213> ORGANISM: Artificial Sequence
<220> FEATURE:
<223> OTHER INFORMATION: Synthetic

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Thr Ser Thr Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Leu
                85                  90                  95

Thr Phe Gly Gly Gly Thr Lys Val Glu Ile Lys
            100                 105

<210> SEQ ID NO 71
<211> LENGTH: 18
<212> TYPE: DNA
<213> ORGANISM: Artificial Sequence
<220> FEATURE:
<223> OTHER INFORMATION: Synthetic

<400> SEQUENCE: 71
cagggcatta gcaattat                                                   18

<210> SEQ ID NO 72
<211> LENGTH: 6
<212> TYPE: PRT
<213> ORGANISM: Artificial Sequence
<220> FEATURE:
<223> OTHER INFORMATION: Synthetic

<400> SEQUENCE: 72

Gln Gly Ile Ser Asn Tyr
1               5

<210> SEQ ID NO 73
<211> LENGTH: 9
<212> TYPE: DNA
<213> ORGANISM: Artificial Sequence
<220> FEATURE:
<223> OTHER INFORMATION: Synthetic

<400> SEQUENCE: 73 gctacatcc                                                              9

<210> SEQ ID NO 74
<211> LENGTH: 3
<212> TYPE: PRT
<213> ORGANISM: Artificial Sequence
<220> FEATURE:
<223> OTHER INFORMATION: Synthetic

<400> SEQUENCE: 74

Ala Thr Ser
1

<210> SEQ ID NO 75
<211> LENGTH: 27
<212> TYPE: DNA
<213> ORGANISM: Artificial Sequence
<220> FEATURE:
<223> OTHER INFORMATION: Synthetic

<400> SEQUENCE: 75
caacagtata atagtttccc gctcact                                         27

<210> SEQ ID NO 76
<211> LENGTH: 9
<212> TYPE: PRT
<213> ORGANISM: Artificial Sequence
<220> FEATURE:
<223> OTHER INFORMATION: Synthetic

<400> SEQUENCE: 76

Gln Gln Tyr Asn Ser Phe Pro Leu Thr
1               5

<210> SEQ ID NO 77
<211> LENGTH: 1356
<212> TYPE: DNA
<213> ORGANISM: Artificial Sequence
<220> FEATURE:
<223> OTHER INFORMATION: Synthetic

<400> SEQUENCE: 77
gaggtgcagc tggtggagtc tgggggaggc ttggtacagc ctggagggtc cctgagactc      60
tcctgtgcag cctctggatt caccttcaat aattatgaaa tgaactgggt ccgccaggct     120

```
ccagggaagg ggctggagtg ggtatcattc attagtagta gtggtagtac catagactac    180
gcagtctctg tgaagggccg attcaccatc tccagagaca acgccaagaa ctcactgtat    240
ctgcaaatga acagcctgag acccggggac acggctgttt attactgtgc gagagcccgg    300
ctagacttct attattacgg tatggacgtc tggggccaag gaccacggt caccgtctcc      360 tcagcctcca ccaagggccc atcggtcttc cccctggcac cctcctccaa gagcacctct    420 ggggggcacag cggccctggg ctgcctggtc aaggactact tccccgaacc ggtgacggtg   480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg   720
ggaccgtcag tcttcctctt ccccccaaaa cccaaggaca cctcatgat ctcccggacc     780 cctgaggtca catgcgtggt ggtggacgtg agccacgaag accctgaggt caagttcaac   840
tggtacgtgg acggcgtgga ggtgcataat gccaagacaa agccgcggga ggagcagtac   900
aacagcacgt accgtgtggt cagcgtcctc accgtcctgc accaggactg gctgaatggc   960
aaggagtaca agtgcaaggt ctccaacaaa gccctcccag cccccatcga gaaaaccatc    1020
tccaaagcca agggcagcc cgagaaccacaggtgtaca ccctgccccc atcccgggat      1080
gagctgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaagt ccctctccct gtctccgggt aaatga                             1356

<210> SEQ ID NO 78
<211> LENGTH: 451
<212> TYPE: PRT
<213> ORGANISM: Artificial Sequence
<220> FEATURE:
<223> OTHER INFORMATION: Synthetic

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Glu Met Asn Trp Val Arg Gln Ala Pro Gly Lys Gly Leu Glu Trp Val
        35                  40                  45

Ser Phe Ile Ser Ser Ser Gly Ser Thr Ile Asp Tyr Ala Val Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Gly Asp Thr Ala Val Tyr Tyr Cys
                85                  90                  95

Ala Arg Ala Arg Leu Asp Phe Tyr Tyr Tyr Gly Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 79
<211> LENGTH: 645
<212> TYPE: DNA
<213> ORGANISM: Artificial Sequence
<220> FEATURE:
<223> OTHER INFORMATION: Synthetic

<400> SEQUENCE: 79
gacatccaga tgacccagtc tccatcctca ctgtctgcat ctgttggaga cagagtcacc     60
atcacttgtc gggcgagtca gggcattagc aattatttag cctggtttca gcagaagcca    120
gggaaagccc ctaagtccct gatctatgct acatccactt tgcaaagtgg ggtcccatca    180 agttcagcg gcagtggatc tgggacagat tcactctca ccatcagcag cctgcagcct    240 gaagatttg caacgtatta ctgccaacag tataatagtt tcccgctcac tttcggcgga    300

```
gggaccaagg tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg ataacgccc tccaatcggg taactcccag     480
gagagtgtca cagagcagga cagcaaggac agcacctaca gcctcagcag cacctgacg     540 ctgagcaaag cagactacga gaaacacaaa gtctacgcct gcgaagtcac ccatcagggc    600
ctgagctcgc ccgtcacaaa gagcttcaac aggggagagt gttag                   645
```

<210> SEQ ID NO 80
<211> LENGTH: 214
<212> TYPE: PRT
<213> ORGANISM: Artificial Sequence
<220> FEATURE:
<223> OTHER INFORMATION: Synthetic

<400> SEQUENCE: 80

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Thr Ser Thr Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 81
<211> LENGTH: 366
<212> TYPE: DNA
<213> ORGANISM: Artificial Sequence
<220> FEATURE:
<223> OTHER INFORMATION: Synthetic

<400> SEQUENCE: 81

```
gaagtgcagc tggtggagtc tgggggaggc ttggttcagc ctggctggtc cctgagactc    60
tcctgtgcag cctctggatt cacctttgat gattatgcca tgcactgggt ccggcaagct   120
```

```
ccagggaagg gcctggaatg ggtctcaggt attagttgga atagtgatga catagactat    180
acggactctg tgaagggccg cttcaccgtc tccagagaca acgccaagaa ctccctgtat    240
ctgcaaatga acagtctgag agctgacgac acggccttct attattgtgt aagacaacgc    300
gtccgaggct attactattt cggtatggac gtctggggcc aagggaccac ggtcaccgtc    360
tcctca                                                                366
```

```
<210> SEQ ID NO 82
<211> LENGTH: 122
<212> TYPE: PRT
<213> ORGANISM: Artificial Sequence
<220> FEATURE:
<223> OTHER INFORMATION: Synthetic

<400> SEQUENCE: 82
```

Glu Val Gln Leu Val Glu Ser Gly Gly Gly Leu Val Gln Pro Gly Trp
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Asp Asp Ile Asp Tyr Thr Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Asp Asp Thr Ala Phe Tyr Tyr Cys
                85                  90                  95

Val Arg Gln Arg Val Arg Gly Tyr Tyr Tyr Phe Gly Met Asp Val Trp
            100                 105                 110

Gly Gln Gly Thr Thr Val Thr Val Ser Ser
        115                 120

```
<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggattcacct ttgatgatta tgcc                                            24
```

```
<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84
```

Gly Phe Thr Phe Asp Asp Tyr Ala
1               5

```
<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
```
attagttgga atagtgatga cata                                                24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ile Ser Trp Asn Ser Asp Asp Ile
1               5

<210> SEQ ID NO 87
<211> LENGTH: 45
<212> TYPE: DNA
<213> ORGANISM: Artificial Sequence
<220> FEATURE:
<223> OTHER INFORMATION: Synthetic

<400> SEQUENCE: 87
gtaagacaac gcgtccgagg ctattactat ttcggtatgg acgtc            45

<210> SEQ ID NO 88
<211> LENGTH: 15
<212> TYPE: PRT
<213> ORGANISM: Artificial Sequence
<220> FEATURE:
<223> OTHER INFORMATION: Synthetic

<400> SEQUENCE: 88

Val Arg Gln Arg Val Arg Gly Tyr Tyr Tyr Phe Gly Met Asp Val
1               5                   10                  15

<210> SEQ ID NO 89
<211> LENGTH: 321
<212> TYPE: DNA
<213> ORGANISM: Artificial Sequence
<220> FEATURE:
<223> OTHER INFORMATION: Synthetic

<400> SEQUENCE: 89
gacatccaga tgacccagtc tccatcctca ctgtctgcat ctgtgggaga cagagtcacc     60
atcacttgtc gggcgagtca gggcatcagc aattatttag cctggtttca gcagaaacca    120
gggaaagccc ctatgtccct gatctatgct gcatccagtt tgcaaagtgg ggtcccatca    180
aagttcagcg gcagtggatc tgggacagat tcactctca ccatcagcag cctgcagcct     240
gaggattttg caacttatta ctgccaacaa tataatagtt acccattcac tttcggccct    300
gggaccaaag tggatatcaa a                                              321

<210> SEQ ID NO 90
<211> LENGTH: 107
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Phe Gln Gln Lys Pro Gly Lys Ala Pro Met Ser Leu Ile 35                  40                  45
Tyr Ala Ala Ser Ser Leu Gln Ser Gly Val Pro Ser Lys Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ser Tyr Pro Phe
                85                  90                  95
Thr Phe Gly Pro Gly Thr Lys Val Asp Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
cagggcatca gcaattat                                                   18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Gly Ile Ser Asn Tyr
1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gctgcatcc                                                              9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Ala Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
caacaatata atagttaccc attcact                                         27

<210> SEQ ID NO 96
<211> LENGTH: 9

```
<212> TYPE: PRT
<213> ORGANISM: Artificial Sequence
<220> FEATURE:
<223> OTHER INFORMATION: Synthetic

<400> SEQUENCE: 96

Gln Gln Tyr Asn Ser Tyr Pro Phe Thr
1               5

<210> SEQ ID NO 97
<211> LENGTH: 1359
<212> TYPE: DNA
<213> ORGANISM: Artificial Sequence
<220> FEATURE:
<223> OTHER INFORMATION: Synthetic

<400> SEQUENCE: 97
```

| | | | | | |
|---|---|---|---|---|---|
| gaagtgcagc | tggtggagtc | tgggggaggc | ttggttcagc | ctggctggtc | cctgagactc | 60 |
| tcctgtgcag | cctctggatt | cacctttgat | gattatgcca | tgcactgggt | ccggcaagct | 120 |
| ccagggaagg | gcctggaatg | ggtctcaggt | attagttgga | atagtgatga | catagactat | 180 |
| acggactctg | tgaagggccg | cttcaccgtc | tccagagaca | acgccaagaa | ctccctgtat | 240 |
| ctgcaaatga | acagtctgag | agctgacgac | acggccttct | attattgtgt | aagacaacgc | 300 |
| gtccgaggct | attactattt | cggtatggac | gtctggggcc | aagggaccac | ggtcaccgtc | 360 |
| tcctcagcct | ccaccaaggg | cccatcggtc | ttccccctgg | cacccctc | caagagcacc | 420 |
| tctgggggca | cagcggccct | gggctgcctg | gtcaaggact | acttccccga | accggtgacg | 480 |
| gtgtcgtgga | actcaggcgc | cctgaccagc | ggcgtgcaca | ccttcccggc | tgtcctacag | 540 |
| tcctcaggac | tctactccct | cagcagcgtg | gtgaccgtgc | cctccagcag | cttgggcacc | 600 |
| cagacctaca | tctgcaacgt | gaatcacaag | cccagcaaca | ccaaggtgga | caagaaagtt | 660 |
| gagcccaaat | cttgtgacaa | aactcacaca | tgcccaccgt | gcccagcacc | tgaactcctg | 720 |
| gggggaccgt | cagtcttcct | cttccccca | aacccaagg | acaccctcat | gatctcccgg | 780 |
| acccctgagg | tcacatgcgt | ggtggtggac | gtgagccacg | aagaccctga | ggtcaagttc | 840 |
| aactggtacg | tggacggcgt | ggaggtgcat | aatgccaaga | caaagccgcg | ggaggagcag | 900 |
| tacaacagca | cgtaccgtgt | ggtcagcgtc | ctcaccgtcc | tgcaccagga | ctggctgaat | 960 |
| ggcaaggagt | acaagtgcaa | ggtctccaac | aaagccctcc | cagcccccat | cgagaaaacc | 1020 |
| atctccaaag | ccaaagggca | gccccgagaa | ccacaggtgt | acaccctgcc | cccatcccgg | 1080 |
| gatgagctga | ccaagaacca | ggtcagcctg | acctgcctgg | tcaaaggctt | ctatcccagc | 1140 |
| gacatcgccg | tggagtggga | gagcaatggg | cagccggaga | caactacaa | gaccacgcct | 1200 |
| cccgtgctgg | actccgacgg | ctccttcttc | ctctacagca | agctcaccgt | ggacaagagc | 1260 |
| aggtggcagc | aggggaacgt | cttctcatgc | tccgtgatgc | atgaggctct | gcacaaccac | 1320 |
| tacacgcaga | agtccctctc | cctgtctccg | ggtaaatga | | | 1359 |

```
<210> SEQ ID NO 98
<211> LENGTH: 452
<212> TYPE: PRT
<213> ORGANISM: Artificial Sequence
<220> FEATURE:
<223> OTHER INFORMATION: Synthetic

<400> SEQUENCE: 98

Glu Val Gln Leu Val Glu Ser Gly Gly Gly Leu Val Gln Pro Gly Trp
1               5                   10                  15
```

```
Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Asp Asp Ile Asp Tyr Thr Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Asp Asp Thr Ala Phe Tyr Tyr Cys
                85                  90                  95

Val Arg Gln Arg Val Arg Gly Tyr Tyr Tyr Phe Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
```

<210> SEQ ID NO 99
<211> LENGTH: 645
<212> TYPE: DNA
<213> ORGANISM: Artificial Sequence
<220> FEATURE:
<223> OTHER INFORMATION: Synthetic

<400> SEQUENCE: 99

```
gacatccaga tgacccagtc tccatcctca ctgtctgcat ctgtgggaga cagagtcacc    60
atcacttgtc gggcgagtca gggcatcagc aattatttag cctggtttca gcagaaacca   120
gggaaagccc ctatgtccct gatctatgct gcatccagtt tgcaaagtgg ggtcccatca   180
aagttcagcg gcagtggatc tgggacagat ttcactctca ccatcagcag cctgcagcct   240
gaggattttg caacttatta ctgccaacaa tataatagtt acccattcac tttcggccct   300
gggaccaaag tggatatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag              645
```

<210> SEQ ID NO 100
<211> LENGTH: 214
<212> TYPE: PRT
<213> ORGANISM: Artificial Sequence
<220> FEATURE:
<223> OTHER INFORMATION: Synthetic

<400> SEQUENCE: 100

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Met Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 101
<211> LENGTH: 366
<212> TYPE: DNA
<213> ORGANISM: Artificial Sequence
<220> FEATURE:
<223> OTHER INFORMATION: Synthetic

<400> SEQUENCE: 101
caggtgcagc tgcaggagtc gggtccagga ctggtgaagc cttcggagac cctgtccctc      60
atgtgcactg tctccggagg ctccatcaat aattactact ggagctggat ccggcagccc     120
ccagggaagg gactggaatg gattggatat atttataacg gtgggatcac caagtacaac     180
ccctccctca gagtcgagt caccatatca gtggacacgt ccaagagcca gatctccctg      240
aagttgaact ctgtgaccgc tgcggacacg gccttttatt actgtactaa ggaacaactg     300
gaacgacgag aggggcacat ctggttcgac ccctggggcc agggaaccct ggtcaccgtc     360
tcctca                                                                366

<210> SEQ ID NO 102
<211> LENGTH: 122
<212> TYPE: PRT
<213> ORGANISM: Artificial Sequence
<220> FEATURE:
<223> OTHER INFORMATION: Synthetic

<400> SEQUENCE: 102

Gln Val Gln Leu Gln Glu Ser Gly Pro Gly Leu Val Lys Pro Ser Glu
1               5                   10                  15

Thr Leu Ser Leu Met Cys Thr Val Ser Gly Gly Ser Ile Asn Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Asn Gly Gly Ile Thr Lys Tyr Asn Pro Ser Leu Lys
    50                  55                  60

Ser Arg Val Thr Ile Ser Val Asp Thr Ser Lys Ser Gln Ile Ser Leu
65                  70                  75                  80

Lys Leu Asn Ser Val Thr Ala Ala Asp Thr Ala Phe Tyr Tyr Cys Thr
                85                  90                  95

Lys Glu Gln Leu Glu Arg Arg Glu Gly His Ile Trp Phe Asp Pro Trp
            100                 105                 110

Gly Gln Gly Thr Leu Val Thr Val Ser Ser
        115                 120

<210> SEQ ID NO 103
<211> LENGTH: 24
<212> TYPE: DNA
<213> ORGANISM: Artificial Sequence
<220> FEATURE:
<223> OTHER INFORMATION: Synthetic

<400> SEQUENCE: 103
ggaggctcca tcaataatta ctac                                             24

<210> SEQ ID NO 104
<211> LENGTH: 8
<212> TYPE: PRT
<213> ORGANISM: Artificial Sequence
<220> FEATURE:
<223> OTHER INFORMATION: Synthetic

<400> SEQUENCE: 104

Gly Gly Ser Ile Asn Asn Tyr Tyr
1               5

<210> SEQ ID NO 105
<211> LENGTH: 21
<212> TYPE: DNA
<213> ORGANISM: Artificial Sequence
<220> FEATURE:
<223> OTHER INFORMATION: Synthetic

<400> SEQUENCE: 105
atttataacg gtgggatcac c                                             21

<210> SEQ ID NO 106
<211> LENGTH: 7
<212> TYPE: PRT
<213> ORGANISM: Artificial Sequence
<220> FEATURE:
<223> OTHER INFORMATION: Synthetic

<400> SEQUENCE: 106

Ile Tyr Asn Gly Gly Ile Thr
1               5

<210> SEQ ID NO 107
<211> LENGTH: 48
<212> TYPE: DNA
<213> ORGANISM: Artificial Sequence
<220> FEATURE:
<223> OTHER INFORMATION: Synthetic

<400> SEQUENCE: 107
actaaggaac aactggaacg acgagagggg cacatctggt tcgacccc                48

<210> SEQ ID NO 108
<211> LENGTH: 16
<212> TYPE: PRT
<213> ORGANISM: Artificial Sequence
<220> FEATURE:
<223> OTHER INFORMATION: Synthetic

<400> SEQUENCE: 108

Thr Lys Glu Gln Leu Glu Arg Arg Glu Gly His Ile Trp Phe Asp Pro
1               5                   10                  15

<210> SEQ ID NO 109
<211> LENGTH: 321
<212> TYPE: DNA
<213> ORGANISM: Artificial Sequence
<220> FEATURE:
<223> OTHER INFORMATION: Synthetic

<400> SEQUENCE: 109
gacatccaga tgacccagtc tccttcctcc ctgtctgcgt ctgtaggaga cagagtcacc    60
atcacttgcc gggcaagtca gaccattaac aactatttaa attggtatca ccagaaacca   120
gggaaagccc ctaaactcct gatctatggt acatccagtt tgcaaagtgg ggtcccatca   180
aggttcagtg gcagtggatc tgggacagaa ttcgctctca ccatcagcag tctgcaacct    240
gaagattttg caacctacta ctgtcaacag agttccagta ccccgtacac ttttggccag    300
gggaccaagc tggagatcaa a                                              321

<210> SEQ ID NO 110
<211> LENGTH: 107
<212> TYPE: PRT
<213> ORGANISM: Artificial Sequence
<220> FEATURE:
<223> OTHER INFORMATION: Synthetic

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asn Asn Tyr
            20                  25                  30

Leu Asn Trp Tyr His Gln Lys Pro Gly Lys Ala Pro Lys Leu Leu Ile
        35                  40                  45

Tyr Gly Thr Ser Ser Leu Gln Ser Gly Val Pro Ser Arg Phe Ser Gly
    50                  55                  60

Ser Gly Ser Gly Thr Glu Phe Ala Leu Thr Ile Ser Ser Leu Gln Pro
65                  70                  75                  80

Glu Asp Phe Ala Thr Tyr Tyr Cys Gln Gln Ser Ser Ser Thr Pro Tyr
                85                  90                  95

Thr Phe Gly Gln Gly Thr Lys Leu Glu Ile Lys
            100                 105

<210> SEQ ID NO 111
<211> LENGTH: 18
<212> TYPE: DNA
<213> ORGANISM: Artificial Sequence
<220> FEATURE:
<223> OTHER INFORMATION: Synthetic

<400> SEQUENCE: 111
cagaccatta acaactat                                                  18

<210> SEQ ID NO 112
<211> LENGTH: 6
<212> TYPE: PRT
<213> ORGANISM: Artificial Sequence
<220> FEATURE:
<223> OTHER INFORMATION: Synthetic

<400> SEQUENCE: 112

Gln Thr Ile Asn Asn Tyr
1               5

<210> SEQ ID NO 113
<211> LENGTH: 9
<212> TYPE: DNA
<213> ORGANISM: Artificial Sequence
<220> FEATURE:
<223> OTHER INFORMATION: Synthetic

<400> SEQUENCE: 113 ggtacatcc                                                            9

<210> SEQ ID NO 114
<211> LENGTH: 3
<212> TYPE: PRT

```
<213> ORGANISM: Artificial Sequence
<220> FEATURE:
<223> OTHER INFORMATION: Synthetic

<400> SEQUENCE: 114

Gly Thr Ser
1

<210> SEQ ID NO 115
<211> LENGTH: 27
<212> TYPE: DNA
<213> ORGANISM: Artificial Sequence
<220> FEATURE:
<223> OTHER INFORMATION: Synthetic

<400> SEQUENCE: 115
caacagagtt ccagtacccc gtacact                                         27

<210> SEQ ID NO 116
<211> LENGTH: 9
<212> TYPE: PRT
<213> ORGANISM: Artificial Sequence
<220> FEATURE:
<223> OTHER INFORMATION: Synthetic

<400> SEQUENCE: 116

Gln Gln Ser Ser Ser Thr Pro Tyr Thr
1               5

<210> SEQ ID NO 117
<211> LENGTH: 1359
<212> TYPE: DNA
<213> ORGANISM: Artificial Sequence
<220> FEATURE:
<223> OTHER INFORMATION: Synthetic

<400> SEQUENCE: 117
caggtgcagc tgcaggagtc gggtccagga ctggtgaagc cttcggagac cctgtccctc      60
atgtgcactg tctccggagg ctccatcaat aattactact ggagctggat ccggcagccc     120
ccagggaagg gactgaatg gattggatat atttataacg gtgggatcac caagtacaac      180
ccctccctca agagtcgagt caccatatca gtggacacgt ccaagagcca gatctccctg     240
aagttgaact ctgtgaccgc tgcggacacg gccttttatt actgtactaa ggaacaactg     300
gaacgacgag aggggcacat ctggttcgac ccctggggcc agggaaccct ggtcaccgtc     360
tcctcagcct ccaccaaggg cccatcggtc ttccccctgg cacccctcc caagagcacc     420
tctgggggca gcggccct gggctgcctg gtcaaggact acttccccga accggtgacg      480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagaaagtt     660
gagcccaaat cttgtgacaa aactcacaca tgcccaccgt gcccagcacc tgaactcctg     720
gggggaccgt cagtcttcct cttccccca aaacccaagg acaccctcat gatctcccgg      780
accctgagg tcacatgcgt ggtggtggac gtgagccacg aagaccctga ggtcaagttc      840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcaa ggtctccaac aaagccctcc cagcccccat cgagaaaacc    1020
atctccaaag ccaaagggca gccccgagaa ccacaggtgt acaccctgcc cccatcccgg    1080
```

```
gatgagctga ccaagaacca ggtcagcctg acctgcctgg tcaaaggctt ctatcccagc    1140
gacatcgccg tggagtggga gagcaatggg cagccggaga caactacaa gaccacgcct     1200 cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga agtccctctc cctgtctccg ggtaaatga                           1359
```

<210> SEQ ID NO 118
<211> LENGTH: 452
<212> TYPE: PRT
<213> ORGANISM: Artificial Sequence
<220> FEATURE:
<223> OTHER INFORMATION: Synthetic

<400> SEQUENCE: 118

```
Gln Val Gln Leu Gln Glu Ser Gly Pro Gly Leu Val Lys Pro Ser Glu
1               5                   10                  15

Thr Leu Ser Leu Met Cys Thr Val Ser Gly Gly Ser Ile Asn Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Asn Gly Gly Ile Thr Lys Tyr Asn Pro Ser Leu Lys
    50                  55                  60

Ser Arg Val Thr Ile Ser Val Asp Thr Ser Lys Ser Gln Ile Ser Leu
65                  70                  75                  80

Lys Leu Asn Ser Val Thr Ala Ala Asp Thr Ala Phe Tyr Tyr Cys Thr
                85                  90                  95

Lys Glu Gln Leu Glu Arg Arg Glu Gly His Ile Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
```

```
            305                 310                 315                 320
Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 119
<211> LENGTH: 645
<212> TYPE: DNA
<213> ORGANISM: Artificial Sequence
<220> FEATURE:
<223> OTHER INFORMATION: Synthetic

<400> SEQUENCE: 119
gacatccaga tgacccagtc tccttcctcc ctgtctgcgt ctgtaggaga cagagtcacc      60
atcacttgcc gggcaagtca gaccattaac aactatttaa attggtatca ccagaaacca     120
gggaaagccc ctaaactcct gatctatggt acatccagtt tgcaaagtgg ggtcccatca     180
aggttcagtg gcagtggatc tgggacagaa ttcgctctca ccatcagcag tctgcaacct     240
gaagattttg caacctacta ctgtcaacag agttccagta cccgtacac ttttggccag      300 gggaccaagc tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga aaacacaaa gtctacgcct gcgaagtcac ccatcagggc      600
ctgagctcgc ccgtcacaaa gagcttcaac aggggagagt gttag                     645

<210> SEQ ID NO 120
<211> LENGTH: 214
<212> TYPE: PRT
<213> ORGANISM: Artificial Sequence
<220> FEATURE:
<223> OTHER INFORMATION: Synthetic

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asn Asn Tyr
            20                  25                  30

Leu Asn Trp Tyr His Gln Lys Pro Gly Lys Ala Pro Lys Leu Leu Ile
        35                  40                  45
```

Tyr Gly Thr Ser Ser Leu Gln Ser Gly Val Pro Ser Arg Phe Ser Gly
            50                  55                  60

Ser Gly Ser Gly Thr Glu Phe Ala Leu Thr Ile Ser Ser Leu Gln Pro
 65                  70                  75                  80

Glu Asp Phe Ala Thr Tyr Tyr Cys Gln Gln Ser Ser Ser Thr Pro Tyr
                85                  90                  95

Thr Phe Gly Gln Gly Thr Lys Leu Glu Ile Lys Arg Thr Val Ala Ala
               100                 105                 110

Pro Ser Val Phe Ile Phe Pro Pro Ser Asp Glu Gln Leu Lys Ser Gly
           115                 120                 125

Thr Ala Ser Val Val Cys Leu Leu Asn Asn Phe Tyr Pro Arg Glu Ala
       130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 121
<211> LENGTH: 354
<212> TYPE: DNA
<213> ORGANISM: Artificial Sequence
<220> FEATURE:
<223> OTHER INFORMATION: Synthetic

<400> SEQUENCE: 121
gaggtgcagc tggtggagtc tgggggaggc ttggtacagc ctgggggggtc cctgagactc    60 tcctgtgcag cctctggatt caccttcagt agatacgaca tgcactgggt ccgccaagtt   120
acaggaaaag gtctggagtg gtctcagtt attggtactg ctggtgacac ttactatcca   180
gactccgtga agggccgatt caccatctcc agagaaaatg ccaagaactc cttgtctctt   240
caaatgaaca gcctgagagc cggggacacg gctgtgtatt actgtacaag atcctataac   300
tggaactttc cctttggcta ctggggccag ggaaccctgg tcaccgtctc ctca         354

<210> SEQ ID NO 122
<211> LENGTH: 118
<212> TYPE: PRT
<213> ORGANISM: Artificial Sequence
<220> FEATURE:
<223> OTHER INFORMATION: Synthetic

<400> SEQUENCE: 122

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
             20                  25                  30

Asp Met His Trp Val Arg Gln Thr Gly Lys Gly Leu Glu Trp Val
            35                  40                  45

Ser Val Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Ser Leu

Gln Met Asn Ser Leu Arg Ala Gly Asp Thr Ala Val Tyr Tyr Cys Thr
65                  70                  75                  80

Arg Ser Tyr Asn Trp Asn Phe Pro Phe Gly Tyr Trp Gly Gln Gly Thr
            85                  90                  95

Leu Val Thr Val Ser Ser
        100                 105                 110

115

<210> SEQ ID NO 123
<211> LENGTH: 24
<212> TYPE: DNA
<213> ORGANISM: Artificial Sequence
<220> FEATURE:
<223> OTHER INFORMATION: Synthetic

<400> SEQUENCE: 123
ggattcacct tcagtagata cgac                                          24

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Gly Phe Thr Phe Ser Arg Tyr Asp
1               5

<210> SEQ ID NO 125
<211> LENGTH: 21
<212> TYPE: DNA
<213> ORGANISM: Artificial Sequence
<220> FEATURE:
<223> OTHER INFORMATION: Synthetic

<400> SEQUENCE: 125
attggtactg ctggtgacac t                                             21

<210> SEQ ID NO 126
<211> LENGTH: 7
<212> TYPE: PRT
<213> ORGANISM: Artificial Sequence
<220> FEATURE:
<223> OTHER INFORMATION: Synthetic

<400> SEQUENCE: 126

Ile Gly Thr Ala Gly Asp Thr
1               5

<210> SEQ ID NO 127
<211> LENGTH: 36
<212> TYPE: DNA
<213> ORGANISM: Artificial Sequence
<220> FEATURE:
<223> OTHER INFORMATION: Synthetic

<400> SEQUENCE: 127
acaagatcct ataactggaa ctttcccttt ggctac                             36

<210> SEQ ID NO 128
<211> LENGTH: 12
<212> TYPE: PRT
<213> ORGANISM: Artificial Sequence
<220> FEATURE:

<223> OTHER INFORMATION: Synthetic

<400> SEQUENCE: 128

Thr Arg Ser Tyr Asn Trp Asn Phe Pro Phe Gly Tyr
1               5                   10

<210> SEQ ID NO 129
<211> LENGTH: 321
<212> TYPE: DNA
<213> ORGANISM: Artificial Sequence
<220> FEATURE:
<223> OTHER INFORMATION: Synthetic

<400> SEQUENCE: 129
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctagactcct gatctatgag gcgtctagtt tagaaactgg ggtcccatca   180
aggttcagcg gcagtggatc tgggacagaa ttcactctca ccatcagcag cctgcagcct   240
gatgattttg caacttatta ctgccaacag tataatcgtt atccgtggac gttcggccaa   300
gggaccaagg tggaaatcaa a                                             321

<210> SEQ ID NO 130
<211> LENGTH: 107
<212> TYPE: PRT
<213> ORGANISM: Artificial Sequence
<220> FEATURE:
<223> OTHER INFORMATION: Synthetic

<400> SEQUENCE: 130

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Arg Leu Leu Ile
        35                  40                  45

Tyr Glu Ala Ser Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Arg Tyr Pro Trp
                85                  90                  95

Thr Phe Gly Gln Gly Thr Lys Val Glu Ile Lys
            100                 105

<210> SEQ ID NO 131
<211> LENGTH: 18
<212> TYPE: DNA
<213> ORGANISM: Artificial Sequence
<220> FEATURE:
<223> OTHER INFORMATION: Synthetic

<400> SEQUENCE: 131
cagagtatta gtagctgg                                                  18

<210> SEQ ID NO 132
<211> LENGTH: 6
<212> TYPE: PRT
<213> ORGANISM: Artificial Sequence
<220> FEATURE:
<223> OTHER INFORMATION: Synthetic

<400> SEQUENCE: 132

Gln Ser Ile Ser Ser Trp
1               5

<210> SEQ ID NO 133
<211> LENGTH: 9
<212> TYPE: DNA
<213> ORGANISM: Artificial Sequence
<220> FEATURE:
<223> OTHER INFORMATION: Synthetic

<400> SEQUENCE: 133 gaggcgtct                                                                    9

<210> SEQ ID NO 134
<211> LENGTH: 3
<212> TYPE: PRT
<213> ORGANISM: Artificial Sequence
<220> FEATURE:
<223> OTHER INFORMATION: Synthetic

<400> SEQUENCE: 134

Glu Ala Ser
1

<210> SEQ ID NO 135
<211> LENGTH: 27
<212> TYPE: DNA
<213> ORGANISM: Artificial Sequence
<220> FEATURE:
<223> OTHER INFORMATION: Synthetic

<400> SEQUENCE: 135
caacagtata atcgttatcc gtggacg                                               27

<210> SEQ ID NO 136
<211> LENGTH: 9
<212> TYPE: PRT
<213> ORGANISM: Artificial Sequence
<220> FEATURE:
<223> OTHER INFORMATION: Synthetic

<400> SEQUENCE: 136

Gln Gln Tyr Asn Arg Tyr Pro Trp Thr
1               5

<210> SEQ ID NO 137
<211> LENGTH: 1347
<212> TYPE: DNA
<213> ORGANISM: Artificial Sequence
<220> FEATURE:
<223> OTHER INFORMATION: Synthetic

<400> SEQUENCE: 137
gaggtgcagc tggtggagtc tgggggaggc ttggtacagc ctggggggtc cctgagactc      60
tcctgtgcag cctctggatt caccttcagt agatacgaca tgcactgggt ccgccaagtt     120
acaggaaaag gtctggagtg ggtctcagtt attggtactg ctggtgacac ttactatcca     180
gactccgtga agggccgatt caccatctcc agagaaaatg ccaagaactc cttgtctctt     240
caaatgaaca gcctgagagc cggggacacg gctgtgtatt actgtacaag atcctataac     300
tggaactttc cctttggcta ctgggccag ggaaccctgg tcaccgtctc ctcagcctcc     360
accaagggcc catcggtctt ccccctggca ccctcctcca agagcacctc tgggggcaca     420

```
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcaccca gacctacatc      600 tgcaacgtga atcacaagcc cagcaacacc aaggtggaca gaaagttga cccaaatct       660 tgtgacaaaa ctcacacatg cccaccgtgc ccagcacctg aactcctggg gggaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
taccgtgtgg tcagcgtcct caccgtcctg caccaggact ggctgaatgg caaggagtac     960
aagtgcaagg tctccaacaa agccctccca gcccccatcg agaaaaccat ctccaaagcc    1020
aaagggcagc cccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
tccctctccc tgtctccggg taaatga                                        1347
```

<210> SEQ ID NO 138
<211> LENGTH: 448
<212> TYPE: PRT
<213> ORGANISM: Artificial Sequence
<220> FEATURE:
<223> OTHER INFORMATION: Synthetic

<400> SEQUENCE: 138

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Arg Tyr
            20                  25                  30

Asp Met His Trp Val Arg Gln Val Thr Gly Lys Gly Leu Glu Trp Val
        35                  40                  45

Ser Val Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Ser Leu
65                  70                  75                  80

Gln Met Asn Ser Leu Arg Ala Gly Asp Thr Ala Val Tyr Tyr Cys Thr
                85                  90                  95

Arg Ser Tyr Asn Trp Asn Phe Pro Phe Gly Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190
```

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 139
<211> LENGTH: 645
<212> TYPE: DNA
<213> ORGANISM: Artificial Sequence
<220> FEATURE:
<223> OTHER INFORMATION: Synthetic

<400> SEQUENCE: 139

```
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctagactcct gatctatgag gcgtctagtt tagaaactgg ggtcccatca     180
aggttcagcg gcagtggatc tgggacagaa ttcactctca ccatcagcag cctgcagcct     240
gatgattttg caacttatta ctgccaacag tataatcgtt atccgtggac gttcggccaa     300
gggaccaagg tggaaatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                     645
```

<210> SEQ ID NO 140
<211> LENGTH: 214
<212> TYPE: PRT
<213> ORGANISM: Artificial Sequence
<220> FEATURE:
<223> OTHER INFORMATION: Synthetic

<400> SEQUENCE: 140

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Arg Leu Leu Ile
        35                  40                  45

Tyr Glu Ala Ser Ser Leu Glu Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Arg Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 141
<211> LENGTH: 375
<212> TYPE: DNA
<213> ORGANISM: Artificial Sequence
<220> FEATURE:
<223> OTHER INFORMATION: Synthetic

<400> SEQUENCE: 141

```
gaggtgcagc tggtggagtc tgggggaggc ttggtacagc ctggggggtc cctgagactc        60
tcctgtgcag cctctggatt cacctttagc agctctgcca tgagctgggt ccgccaggct       120
ccagggaagg gactggagtg gtctcaact cttaatgttg gtgctgatag cacattctac       180
gcaggctccg tgaggggccg gttcaccatc tccagagaca attccaagaa cacgctgttt       240
ctgcaaatga acagcctgag agccgaggac acggccgtat attactgtgc gaaagattgg       300 gggggggattc catattacta ctactactac ggtatggacg tctggggcca agggaccacg       360
gtcaccgtct cctca                                                         375
```

<210> SEQ ID NO 142

<211> LENGTH: 125
<212> TYPE: PRT
<213> ORGANISM: Artificial Sequence
<220> FEATURE:
<223> OTHER INFORMATION: Synthetic

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Thr Leu Asn Val Gly Ala Asp Ser Thr Phe Tyr Ala Gly Ser Val
    50                  55                  60

Arg Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Asp Trp Gly Gly Ile Pro Tyr Tyr Tyr Tyr Tyr Gly Met
            100                 105                 110

Asp Val Trp Gly Gln Gly Thr Thr Val Thr Val Ser Ser
            115                 120                 125

<210> SEQ ID NO 143
<211> LENGTH: 24
<212> TYPE: DNA
<213> ORGANISM: Artificial Sequence
<220> FEATURE:
<223> OTHER INFORMATION: Synthetic

<400> SEQUENCE: 143
ggattcacct ttagcagctc tgcc                                          24

<210> SEQ ID NO 144
<211> LENGTH: 8
<212> TYPE: PRT
<213> ORGANISM: Artificial Sequence
<220> FEATURE:
<223> OTHER INFORMATION: Synthetic

<400> SEQUENCE: 144

Gly Phe Thr Phe Ser Ser Ser Ala
1               5

<210> SEQ ID NO 145
<211> LENGTH: 24
<212> TYPE: DNA
<213> ORGANISM: Artificial Sequence
<220> FEATURE:
<223> OTHER INFORMATION: Synthetic

<400> SEQUENCE: 145
cttaatgttg gtgctgatag caca                                          24

<210> SEQ ID NO 146
<211> LENGTH: 8
<212> TYPE: PRT
<213> ORGANISM: Artificial Sequence
<220> FEATURE:
<223> OTHER INFORMATION: Synthetic

<400> SEQUENCE: 146

<210> SEQ ID NO 147
<211> LENGTH: 54
<212> TYPE: DNA
<213> ORGANISM: Artificial Sequence
<220> FEATURE:
<223> OTHER INFORMATION: Synthetic

<400> SEQUENCE: 147

```
gcgaaagatt gggggggat tccatattac tactactact acggtatgga cgtc        54
```

<210> SEQ ID NO 148
<211> LENGTH: 18
<212> TYPE: PRT
<213> ORGANISM: Artificial Sequence
<220> FEATURE:
<223> OTHER INFORMATION: Synthetic

<400> SEQUENCE: 148

Ala Lys Asp Trp Gly Gly Ile Pro Tyr Tyr Tyr Tyr Tyr Tyr Gly Met
1               5                   10                  15

Asp Val

<210> SEQ ID NO 149
<211> LENGTH: 321
<212> TYPE: DNA
<213> ORGANISM: Artificial Sequence
<220> FEATURE:
<223> OTHER INFORMATION: Synthetic

<400> SEQUENCE: 149

```
gacatccagt tgacccagtc tccatccttc ctgtctgcat ctgtaggaga cagagtcacc     60
atcacttgct gggccagtca gggcattagc agttatttag cctggtatca gcaaaaacca    120
gggaaagccc ctaacctcct gatctatact gcatccactt tgcaaagtgg ggtcccatcg    180
aggttcagcg gcagtggatc tgggacagaa ttcactctca caatcagcag cctgcagcct    240
gaagattttg caacttatta ctgtcaacag cttaatagtt acccgctcac tttcggcgga    300
gggaccaagg tggagatcaa a                                              321
```

<210> SEQ ID NO 150
<211> LENGTH: 107
<212> TYPE: PRT
<213> ORGANISM: Artificial Sequence
<220> FEATURE:
<223> OTHER INFORMATION: Synthetic

<400> SEQUENCE: 150

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
                20                  25                  30

Leu Ala Trp Tyr Gln Gln Lys Pro Gly Lys Ala Pro Asn Leu Leu Ile
            35                  40                  45

Tyr Thr Ala Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105

<210> SEQ ID NO 151
<211> LENGTH: 18
<212> TYPE: DNA
<213> ORGANISM: Artificial Sequence
<220> FEATURE:
<223> OTHER INFORMATION: Synthetic

<400> SEQUENCE: 151
cagggcatta gcagttat                                                 18

<210> SEQ ID NO 152
<211> LENGTH: 6
<212> TYPE: PRT
<213> ORGANISM: Artificial Sequence
<220> FEATURE:
<223> OTHER INFORMATION: Synthetic

<400> SEQUENCE: 152

Gln Gly Ile Ser Ser Tyr
1               5

<210> SEQ ID NO 153
<211> LENGTH: 9
<212> TYPE: DNA
<213> ORGANISM: Artificial Sequence
<220> FEATURE:
<223> OTHER INFORMATION: Synthetic

<400> SEQUENCE: 153 actgcatcc                                                            9

<210> SEQ ID NO 154
<211> LENGTH: 3
<212> TYPE: PRT
<213> ORGANISM: Artificial Sequence
<220> FEATURE:
<223> OTHER INFORMATION: Synthetic

<400> SEQUENCE: 154

Thr Ala Ser
1

<210> SEQ ID NO 155
<211> LENGTH: 27
<212> TYPE: DNA
<213> ORGANISM: Artificial Sequence
<220> FEATURE:
<223> OTHER INFORMATION: Synthetic

<400> SEQUENCE: 155
caacagctta atagttaccc gctcact                                       27

<210> SEQ ID NO 156
<211> LENGTH: 9
<212> TYPE: PRT
<213> ORGANISM: Artificial Sequence
<220> FEATURE:
<223> OTHER INFORMATION: Synthetic

<400> SEQUENCE: 156

Gln Gln Leu Asn Ser Tyr Pro Leu Thr
1               5

<210> SEQ ID NO 157
<211> LENGTH: 1368
<212> TYPE: DNA
<213> ORGANISM: Artificial Sequence
<220> FEATURE:
<223> OTHER INFORMATION: Synthetic

<400> SEQUENCE: 157

```
gaggtgcagc tggtggagtc tgggggaggc ttggtacagc ctgggggggtc cctgagactc      60
tcctgtgcag cctctggatt cacctttagc agctctgcca tgagctgggt ccgccaggct     120
ccagggaagg gactggagtg gtctcaact cttaatgttg gtgctgatag cacattctac     180
gcaggctccg tgaggggccg gttcaccatc tccagagaca attccaagaa cacgctgttt     240
ctgcaaatga acagcctgag agccgaggac acggccgtat attactgtgc gaaagattgg     300
gggggggattc catattacta ctactactac ggtatggacg tctggggcca agggaccacg     360
gtcaccgtct cctcagcctc caccaagggc ccatcggtct tccccctggc accctcctcc     420
aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagaaagttg agcccaaatc ttgtgacaaa actcacacat gcccaccgtg cccagcacct     720
gaactcctgg ggggaccgtc agtcttcctc ttccccccaa acccaaggga caccctcatg     780
atctcccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgtgtg gtcagcgtcc tcaccgtcct gcaccaggac     960
tggctgaatg gcaaggagta caagtgcaag gtctccaaca aagccctccc agcccccatc    1020
gagaaaacca tctccaaagc caagggcag ccccgagaac cacaggtgta caccctgccc    1080
ccatcccggg atgagctgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacgcagaa gtccctctcc ctgtctccgg gtaaatga               1368
```

<210> SEQ ID NO 158
<211> LENGTH: 455
<212> TYPE: PRT
<213> ORGANISM: Artificial Sequence
<220> FEATURE:
<223> OTHER INFORMATION: Synthetic

<400> SEQUENCE: 158

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Thr Leu Asn Val Gly Ala Asp Ser Thr Phe Tyr Ala Gly Ser Val
    50                  55                  60

Arg Gly Arg Phe Thr Ile Ser Arg Asp Asn Ser Lys Asn Thr Leu Phe
```

```
             65                  70                  75                  80
Leu Gln Met Asn Ser Leu Arg Ala Glu Asp Thr Ala Val Tyr Tyr Cys
                 85                  90                  95

Ala Lys Asp Trp Gly Gly Ile Pro Tyr Tyr Tyr Tyr Gly Met
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
            450                 455

<210> SEQ ID NO 159
<211> LENGTH: 645
<212> TYPE: DNA
<213> ORGANISM: Artificial Sequence
```

<220> FEATURE:
<223> OTHER INFORMATION: Synthetic

<400> SEQUENCE: 159

```
gacatccagt tgacccagtc tccatccttc ctgtctgcat ctgtaggaga cagagtcacc      60
atcacttgct gggccagtca gggcattagc agttatttag cctggtatca gcaaaaacca    120
gggaaagccc ctaacctcct gatctatact gcatccactt tgcaaagtgg ggtcccatcg    180
aggttcagcg gcagtggatc tgggacagaa ttcactctca caatcagcag cctgcagcct    240
gaagattttg caacttatta ctgtcaacag cttaatagtt acccgctcac tttcggcgga    300
gggaccaagg tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```

<210> SEQ ID NO 160
<211> LENGTH: 214
<212> TYPE: PRT
<213> ORGANISM: Artificial Sequence
<220> FEATURE:
<223> OTHER INFORMATION: Synthetic

<400> SEQUENCE: 160

```
Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 161
<211> LENGTH: 375
<212> TYPE: DNA
<213> ORGANISM: Artificial Sequence
<220> FEATURE:
<223> OTHER INFORMATION: Synthetic

<400> SEQUENCE: 161

```
caggtgcagc tgcaggagtc gggcccagga ctggtgaagc cttcggagac cctgtccctc      60
acctgcactg tctctggtgg ctccatcagt ggttatttct ggggctggat ccggcagacc     120
ccagggaagg gactggaatg gattggatat atcttttaca gtgggagcac ccactataat     180
ccctccttca agagtcgagt caccatgtca gtagacacgt ccaagaacca gttcgccctg     240
aagctgaggt ctgtgaccgc cgcagacacg gccaaatatt actgttcgag acagagggaa     300
tactatggtt cgggaaatta tcgctacttc ggtatggacg tctggggcca agggaccacg     360
gtcaccgtct cctca                                                     375
```

<210> SEQ ID NO 162
<211> LENGTH: 125
<212> TYPE: PRT
<213> ORGANISM: Artificial Sequence
<220> FEATURE:
<223> OTHER INFORMATION: Synthetic

<400> SEQUENCE: 162

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Gly Tyr
            20                  25                  30

Phe Trp Gly Trp Ile Arg Gln Thr Pro Gly Lys Gly Leu Glu Trp Ile
        35                  40                  45

Gly Tyr Ile Phe Tyr Ser Gly Ser Thr His Tyr Asn Pro Ser Phe Lys
    50                  55                  60

Ser Arg Val Thr Met Ser Val Asp Thr Ser Lys Asn Gln Phe Ala Leu
65                  70                  75                  80

Lys Leu Arg Ser Val Thr Ala Ala Asp Thr Ala Lys Tyr Tyr Cys Ser
                85                  90                  95

Arg Gln Arg Glu Tyr Tyr Gly Ser Gly Asn Tyr Arg Tyr Phe Gly Met
            100                 105                 110

Asp Val Trp Gly Gln Gly Thr Thr Val Thr Val Ser Ser
        115                 120                 125

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163

```
ggtggctcca tcagtggtta tttc                                            24
```

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

```
Gly Gly Ser Ile Ser Gly Tyr Phe
1               5
```

<210> SEQ ID NO 165
<211> LENGTH: 21
<212> TYPE: DNA
<213> ORGANISM: Artificial Sequence
<220> FEATURE:
<223> OTHER INFORMATION: Synthetic

<400> SEQUENCE: 165

```
atcttttaca gtgggagcac c                                              21
```

<210> SEQ ID NO 166
<211> LENGTH: 7
<212> TYPE: PRT
<213> ORGANISM: Artificial Sequence
<220> FEATURE:
<223> OTHER INFORMATION: Synthetic

<400> SEQUENCE: 166

```
Ile Phe Tyr Ser Gly Ser Thr
1               5
```

<210> SEQ ID NO 167
<211> LENGTH: 57
<212> TYPE: DNA
<213> ORGANISM: Artificial Sequence
<220> FEATURE:
<223> OTHER INFORMATION: Synthetic

<400> SEQUENCE: 167

```
tcgagacaga gggaatacta tggttcggga aattatcgct acttcggtat ggacgtc      57
```

<210> SEQ ID NO 168
<211> LENGTH: 19
<212> TYPE: PRT
<213> ORGANISM: Artificial Sequence
<220> FEATURE:
<223> OTHER INFORMATION: Synthetic

<400> SEQUENCE: 168

```
Ser Arg Gln Arg Glu Tyr Tyr Gly Ser Gly Asn Tyr Arg Tyr Phe Gly
1               5                   10                  15
Met Asp Val
```

<210> SEQ ID NO 169
<211> LENGTH: 321
<212> TYPE: DNA
<213> ORGANISM: Artificial Sequence
<220> FEATURE:
<223> OTHER INFORMATION: Synthetic

<400> SEQUENCE: 169

```
gccatccaga tgacccagtc tccatcctcc ctgtctgcat ctgttggaga gagagtcacc    60
atcacttgcc gggcaagtca ggacattaga gatgatttag ctggtatca gcagagacca   120 gggaaagccc ctaacctcct gatttatgct gcatctagtt tacacagtgg tgtcccatca   180
agattcagcg gcagtgggtc tggcacagat ttcactctca ccatcagcag cctgcagcct   240
gaagattttg caacttatta ctgtctacaa gactacaatt acccgtggac gttcggccaa   300
gggaccaagg tggaaatcaa a                                              321
```

<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

```
Ala Ile Gln Met Thr Gln Ser Pro Ser Ser Leu Ser Ala Ser Val Gly
1               5                   10                  15

Glu Arg Val Thr Ile Thr Cys Arg Ala Ser Gln Asp Ile Arg Asp Asp
            20                  25                  30

Leu Gly Trp Tyr Gln Gln Arg Pro Gly Lys Ala Pro Asn Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105
```

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171
caggacatta gagatgat                                                    18

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

```
Gln Asp Ile Arg Asp Asp
1               5
```

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 gctgcatct                                                               9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

```
Ala Ala Ser
1
```

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
ctacaagact acaattaccc gtggacg                                              27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Leu Gln Asp Tyr Asn Tyr Pro Trp Thr
1               5

<210> SEQ ID NO 177
<211> LENGTH: 1368
<212> TYPE: DNA
<213> ORGANISM: Artificial Sequence
<220> FEATURE:
<223> OTHER INFORMATION: Synthetic

<400> SEQUENCE: 177
caggtgcagc tgcaggagtc gggcccagga ctggtgaagc cttcggagac cctgtccctc        60
acctgcactg tctctggtgg ctccatcagt ggttatttct ggggctggat ccggcagacc       120
ccagggaagg gactggaatg gattggatat atctttttaca gtgggagcac ccactataat      180
ccctccttca gagtcgagt caccatgtca gtagacacgt ccaagaacca gttcgccctg        240
aagctgaggt ctgtgaccgc cgcagacacg gccaaatatt actgttcgag acagagggaa       300
tactatggtt cgggaaatta tcgctacttc ggtatggacg tctggggcca agggaccacg       360
gtcaccgtct cctcagcctc caccaagggc ccatcggtct tccccctggc accctcctcc       420
aagagcacct ctgggggcac agcggccctg gcctgcctgg tcaaggacta cttccccgaa       480
ccggtgacgg tgtcgtggaa ctcaggcgcc ctgaccagcg gcgtgcacac cttcccggct      540
gtcctacagt cctcaggact ctactccctc agcagcgtgg tgaccgtgcc ctccagcagc      600
ttgggcaccc agacctacat ctgcaacgtg aatcacaagc ccagcaacac caaggtggac     660
aagaaagttg agcccaaatc ttgtgacaaa actcacacat gcccaccgtg cccagcacct   720
gaactcctgg gggaccgtc agtcttcctc ttccccccaa acccaaggga caccctcatg     780
atctcccgga ccctgaggt cacatgcgtg gtggtggacg tgagccacga agaccctgag    840
gtcaagttca actggtacgt ggacggcgtg gaggtgcata atgccaagac aaagccgcgg     900
gaggagcagt acaacagcac gtaccgtgtg gtcagcgtcc tcaccgtcct gcaccaggac     960
tggctgaatg gcaaggagta caagtgcaag gtctccaaca aagccctccc agcccccatc   1020
gagaaaacca tctccaaagc caaagggcag ccccgagaac cacaggtgta caccctgccc  1080
ccatcccggg atgagctgac caagaaccag gtcagcctga cctgcctggt caaaggcttc  1140
tatcccagcg acatcgccgt ggagtgggag agcaatgggc agccggagaa caactacaag  1200
accacgcctc ccgtgctgga ctccgacggc tccttcttcc tctacagcaa gctcaccgtg  1260
gacaagagca ggtggcagca ggggaacgtc ttctcatgct ccgtgatgca tgaggctctg  1320
cacaaccact acacgcagaa gtccctctcc ctgtctccgg gtaaatga 1368

<210> SEQ ID NO 178
<211> LENGTH: 455
<212> TYPE: PRT
<213> ORGANISM: Artificial Sequence
<220> FEATURE:
<223> OTHER INFORMATION: Synthetic

<400> SEQUENCE: 178

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Gly Tyr
            20                  25                  30

Phe Trp Gly Trp Ile Arg Gln Thr Pro Gly Lys Gly Leu Glu Trp Ile
        35                  40                  45

Gly Tyr Ile Phe Tyr Ser Gly Ser Thr His Tyr Asn Pro Ser Phe Lys
    50                  55                  60

Ser Arg Val Thr Met Ser Val Asp Thr Ser Lys Asn Gln Phe Ala Leu
65                  70                  75                  80

Lys Leu Arg Ser Val Thr Ala Ala Asp Thr Ala Lys Tyr Tyr Cys Ser
                85                  90                  95

Arg Gln Arg Glu Tyr Tyr Gly Ser Gly Asn Tyr Arg Tyr Phe Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

```
Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455
```

<210> SEQ ID NO 179
<211> LENGTH: 645
<212> TYPE: DNA
<213> ORGANISM: Artificial Sequence
<220> FEATURE:
<223> OTHER INFORMATION: Synthetic

<400> SEQUENCE: 179

```
gccatccaga tgacccagtc tccatcctcc ctgtctgcat ctgttggaga gagagtcacc    60
atcacttgcc gggcaagtca ggacattaga gatgatttag ctggtatca gcagagacca   120
gggaaagccc ctaacctcct gatttatgct gcatctagtt tacacagtgg tgtcccatca   180
agattcagcg gcagtgggtc tggcacagat ttcactctca ccatcagcag cctgcagcct   240
gaagattttg caacttatta ctgtctacaa gactacaatt accgtggac gttcggccaa   300
gggaccaagg tggaaatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg ataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                    645
```

<210> SEQ ID NO 180
<211> LENGTH: 214
<212> TYPE: PRT
<213> ORGANISM: Artificial Sequence
<220> FEATURE:
<223> OTHER INFORMATION: Synthetic

<400> SEQUENCE: 180

```
Ala Ile Gln Met Thr Gln Ser Pro Ser Ser Leu Ser Ala Ser Val Gly
1               5                   10                  15

Glu Arg Val Thr Ile Thr Cys Arg Ala Ser Gln Asp Ile Arg Asp Asp
            20                  25                  30

Leu Gly Trp Tyr Gln Gln Arg Pro Gly Lys Ala Pro Asn Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
```

```
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 181
<211> LENGTH: 378
<212> TYPE: DNA
<213> ORGANISM: Artificial Sequence
<220> FEATURE:
<223> OTHER INFORMATION: Synthetic

<400> SEQUENCE: 181
gaggtgcagc tggtggagtc tgggggaggc ttggtccagc ctggggggtc cctgagactc      60
tcctgtggag cctctggatt cacctttagt tactattgga tgacctgggt ccgccaggct     120
ccagggaagg gctggagtg gtggccaac ataaatcaag atggaagtga gaaattctat      180
gtggactctg tgaggggccg attcaccatc tccagagaca cgcgaagaa gtcactgtat      240 cttcaaatga acagtctgag agccgaggac acggctgtgt attattgtgc gagagacgga     300
tattgtagta gtatcggctg ttataaccte tacggcatgg acgtctgggg ccaagggacc     360
acggtcaccg tctcctca                                                   378

<210> SEQ ID NO 182
<211> LENGTH: 126
<212> TYPE: PRT
<213> ORGANISM: Artificial Sequence
<220> FEATURE:
<223> OTHER INFORMATION: Synthetic

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Ser Tyr Tyr
            20                  25                  30

Trp Met Thr Trp Val Arg Gln Ala Pro Gly Lys Gly Leu Glu Trp Val
        35                  40                  45

Ala Asn Ile Asn Gln Asp Gly Ser Glu Lys Phe Tyr Val Asp Ser Val
    50                  55                  60

Arg Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Cys Ser Ser Ile Gly Cys Tyr Asn Leu Tyr Gly
```

```
                100              105              110
Met Asp Val Trp Gly Gln Gly Thr Thr Val Thr Val Ser Ser
            115              120              125
```

<210> SEQ ID NO 183
<211> LENGTH: 24
<212> TYPE: DNA
<213> ORGANISM: Artificial Sequence
<220> FEATURE:
<223> OTHER INFORMATION: Synthetic

<400> SEQUENCE: 183
ggattcacct ttagttacta ttgg        24

<210> SEQ ID NO 184
<211> LENGTH: 8
<212> TYPE: PRT
<213> ORGANISM: Artificial Sequence
<220> FEATURE:
<223> OTHER INFORMATION: Synthetic

<400> SEQUENCE: 184

```
Gly Phe Thr Phe Ser Tyr Tyr Trp
1               5
```

<210> SEQ ID NO 185
<211> LENGTH: 24
<212> TYPE: DNA
<213> ORGANISM: Artificial Sequence
<220> FEATURE:
<223> OTHER INFORMATION: Synthetic

<400> SEQUENCE: 185
ataaatcaag atggaagtga gaaa        24

<210> SEQ ID NO 186
<211> LENGTH: 8
<212> TYPE: PRT
<213> ORGANISM: Artificial Sequence
<220> FEATURE:
<223> OTHER INFORMATION: Synthetic

<400> SEQUENCE: 186

```
Ile Asn Gln Asp Gly Ser Glu Lys
1               5
```

<210> SEQ ID NO 187
<211> LENGTH: 57
<212> TYPE: DNA
<213> ORGANISM: Artificial Sequence
<220> FEATURE:
<223> OTHER INFORMATION: Synthetic

<400> SEQUENCE: 187
gcgagagacg gatattgtag tagtatcggc tgttataacc tctacggcat ggacgtc        57

<210> SEQ ID NO 188
<211> LENGTH: 19
<212> TYPE: PRT
<213> ORGANISM: Artificial Sequence
<220> FEATURE:
<223> OTHER INFORMATION: Synthetic

<400> SEQUENCE: 188

```
Ala Arg Asp Gly Tyr Cys Ser Ser Ile Gly Cys Tyr Asn Leu Tyr Gly
1               5                   10                  15
```

Met Asp Val

<210> SEQ ID NO 189
<211> LENGTH: 321
<212> TYPE: DNA
<213> ORGANISM: Artificial Sequence
<220> FEATURE:
<223> OTHER INFORMATION: Synthetic

<400> SEQUENCE: 189

```
gacatccaga tgacccagtc tccatcctcc ctgtctgcat ctgtaggaga cagagtcacc      60
atcacttgcc gggcaagtca gaacattaac aagtatttaa attggtatca gcagaaacca     120
gggcaagccc ctaagctcct gatctatact acatccagtt tgcaaagtgg ggtcccatca     180
aggttcagtg gcagtggatc tgggacagat ttcactctca ccatcagcag tctgcaacct     240
gaagattttg caacttattc ctgtcaacag agttacaatt ccccgctcac tttcggcgga     300
gggaccaagg tggagatcaa a                                               321
```

<210> SEQ ID NO 190
<211> LENGTH: 107
<212> TYPE: PRT
<213> ORGANISM: Artificial Sequence
<220> FEATURE:
<223> OTHER INFORMATION: Synthetic

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Lys Tyr
            20                  25                  30

Leu Asn Trp Tyr Gln Gln Lys Pro Gly Gln Ala Pro Lys Leu Leu Ile
        35                  40                  45

Tyr Thr Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Ser Cys Gln Gln Ser Tyr Asn Ser Pro Leu
                85                  90                  95

Thr Phe Gly Gly Gly Thr Lys Val Glu Ile Lys
            100                 105

<210> SEQ ID NO 191
<211> LENGTH: 18
<212> TYPE: DNA
<213> ORGANISM: Artificial Sequence
<220> FEATURE:
<223> OTHER INFORMATION: Synthetic

<400> SEQUENCE: 191
cagaacatta acaagtat                                                    18

<210> SEQ ID NO 192
<211> LENGTH: 6
<212> TYPE: PRT
<213> ORGANISM: Artificial Sequence
<220> FEATURE:
<223> OTHER INFORMATION: Synthetic

<400> SEQUENCE: 192

Gln Asn Ile Asn Lys Tyr

<210> SEQ ID NO 193
<211> LENGTH: 9
<212> TYPE: DNA
<213> ORGANISM: Artificial Sequence
<220> FEATURE:
<223> OTHER INFORMATION: Synthetic

<400> SEQUENCE: 193 actacatcc                                                                9

<210> SEQ ID NO 194
<211> LENGTH: 3
<212> TYPE: PRT
<213> ORGANISM: Artificial Sequence
<220> FEATURE:
<223> OTHER INFORMATION: Synthetic

<400> SEQUENCE: 194

Thr Thr Ser
1

<210> SEQ ID NO 195
<211> LENGTH: 27
<212> TYPE: DNA
<213> ORGANISM: Artificial Sequence
<220> FEATURE:
<223> OTHER INFORMATION: Synthetic

<400> SEQUENCE: 195
caacagagtt acaattcccc gctcact                                           27

<210> SEQ ID NO 196
<211> LENGTH: 9
<212> TYPE: PRT
<213> ORGANISM: Artificial Sequence
<220> FEATURE:
<223> OTHER INFORMATION: Synthetic

<400> SEQUENCE: 196

Gln Gln Ser Tyr Asn Ser Pro Leu Thr
1               5

<210> SEQ ID NO 197
<211> LENGTH: 1371
<212> TYPE: DNA
<213> ORGANISM: Artificial Sequence
<220> FEATURE:
<223> OTHER INFORMATION: Synthetic

<400> SEQUENCE: 197
gaggtgcagc tggtggagtc tgggggaggc ttggtccagc ctggggggtc cctgagactc        60
tcctgtggag cctctggatt caccttagt tactattgga tgacctgggt ccgccaggct       120
ccagggaagg ggctggagtg ggtggccaac ataaatcaag atggaagtga aaattctat       180 gtggactctg tgaggggccg attcaccatc tccagagaca acgcgaagaa gtcactgtat       240
cttcaaatga acagtctgag agccgaggac acggctgtgt attattgtgc gagagacgga       300
tattgtagta gtatcggctg ttataacctc tacggcatgg acgtctgggg ccaagggacc       360
acggtcaccg tctcctcagc ctccaccaag ggcccatcgg tcttcccct ggcaccctcc       420 tccaagagca cctctggggg cacagcggcc ctgggctgcc tggtcaagga ctacttcccc       480
gaaccggtga cggtgtcgtg gaactcaggc gccctgacca gcggcgtgca caccttcccg       540

```
gctgtcctac agtcctcagg actctactcc ctcagcagcg tggtgaccgt gccctccagc   600
agcttgggca cccagaccta catctgcaac gtgaatcaca agcccagcaa caccaaggtg   660
gacaagaaag ttgagcccaa atcttgtgac aaaactcaca catgcccacc gtgcccagca   720
cctgaactcc tggggggacc gtcagtcttc ctcttccccc caaaacccaa ggacaccctc   780
atgatctccc ggacccctga ggtcacatgc gtggtggtgg acgtgagcca cgaagaccct   840
gaggtcaagt tcaactggta cgtggacggc gtggaggtgc ataatgccaa gacaaagccg   900
cgggaggagc agtacaacag cacgtaccgt gtggtcagcg tcctcaccgt cctgcaccag   960
gactggctga atggcaagga gtacaagtgc aaggtctcca acaaagccct cccagccccc  1020
atcgagaaaa ccatctccaa agccaaaggg cagccccgag aaccacaggt gtacaccctg  1080
cccccatccc gggatgagct gaccaagaac caggtcagcc tgacctgcct ggtcaaaggc  1140
ttctatccca gcgacatcgc cgtggagtgg gagagcaatg ggcagccgga gaacaactac  1200
aagaccacgc ctcccgtgct ggactccgac ggctccttct cctctacag caagctcacc  1260 gtggacaaga gcaggtggca gcaggggaac gtcttctcat gctccgtgat gcatgaggct  1320
ctgcacaacc actacacgca gaagtccctc tccctgtctc cgggtaaatg a           1371
```

<210> SEQ ID NO 198
<211> LENGTH: 456
<212> TYPE: PRT
<213> ORGANISM: Artificial Sequence
<220> FEATURE:
<223> OTHER INFORMATION: Synthetic

<400> SEQUENCE: 198

```
Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Ser Tyr Tyr
            20                  25                  30

Trp Met Thr Trp Val Arg Gln Ala Pro Gly Lys Gly Leu Glu Trp Val
        35                  40                  45

Ala Asn Ile Asn Gln Asp Gly Ser Glu Lys Phe Tyr Val Asp Ser Val
    50                  55                  60

Arg Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Cys Ser Ser Ile Gly Cys Tyr Asn Leu Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
```

|  |  |  |  |  | 210 |  |  |  |  | 215 |  |  |  |  | 220 |  |
|---|---|---|---|---|---|---|---|---|---|---|---|---|---|---|---|---|

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
        260                 265                 270

Val Asp Val Ser His Glu Asp Pro Glu Val Lys Phe Asn Trp Tyr Val
    275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
        340                 345                 350

Arg Glu Pro Gln Val Tyr Thr Leu Pro Pro Ser Arg Asp Glu Leu Thr
    355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
        420                 425                 430

Ser Cys Ser Val Met His Glu Ala Leu His Asn His Tyr Thr Gln Lys
    435                 440                 445

Ser Leu Ser Leu Ser Pro Gly Lys
    450                 455

<210> SEQ ID NO 199
<211> LENGTH: 645
<212> TYPE: DNA
<213> ORGANISM: Artificial Sequence
<220> FEATURE:
<223> OTHER INFORMATION: Synthetic

<400> SEQUENCE: 199
gacatccaga tgacccagtc tccatcctcc ctgtctgcat ctgtaggaga cagagtcacc      60
atcacttgcc gggcaagtca gaacattaac aagtatttaa attggtatca gcagaaacca     120
gggcaagccc ctaagctcct gatctatact acatccagtt tgcaaagtgg ggtcccatca     180
aggttcagtg gcagtggatc tgggacagat ttcactctca ccatcagcag tctgcaacct     240
gaagattttg caacttattc ctgtcaacag agttacaatt ccccgctcac tttcggcgga     300
gggaccaagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                    645

<210> SEQ ID NO 200
<211> LENGTH: 214
<212> TYPE: PRT
<213> ORGANISM: Artificial Sequence
<220> FEATURE:
<223> OTHER INFORMATION: Synthetic

<400> SEQUENCE: 200

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asn Ile Asn Lys Tyr
             20                  25                  30

Leu Asn Trp Tyr Gln Gln Lys Pro Gly Gln Ala Pro Lys Leu Leu Ile
         35                  40                  45

Tyr Thr Thr Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Ser Cys Gln Gln Ser Tyr Asn Ser Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 201
<211> LENGTH: 375
<212> TYPE: DNA
<213> ORGANISM: Artificial Sequence
<220> FEATURE:
<223> OTHER INFORMATION: Synthetic

<400> SEQUENCE: 201

```
gaggtgcagc tggtggagtc tgggggaggc ttggtgcagc ctggggggtc cctgagactc      60
tcctgtgcag cctctggatt cacctttagc agatatgaca tgagctgggt ccgccaggct     120
ccagggaagg ggctagagtg ggtctcagct atttcttata gtggtgacag cacatactac     180
gcagactccg tgcagggccg gttcaccata tctagagaca attccaagaa tacgctgtat     240
ctgcaaatga acagtctgag agccgaggac acggccttat atcactgtgc gaaagataat     300
gggtatagtg ggacctacta ctactactac ggtatggacg tctggggcca agggaccacg     360
gtcaccgtct cctca                                                      375
```

<210> SEQ ID NO 202
<211> LENGTH: 125

```
<212> TYPE: PRT
<213> ORGANISM: Artificial Sequence
<220> FEATURE:
<223> OTHER INFORMATION: Synthetic

<400> SEQUENCE: 202

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Asp Met Ser Trp Val Arg Gln Ala Pro Gly Lys Gly Leu Glu Trp Val
        35                  40                  45

Ser Ala Ile Ser Tyr Ser Gly Asp Ser Thr Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr His Cys
                85                  90                  95

Ala Lys Asp Asn Gly Tyr Ser Gly Thr Tyr Tyr Tyr Tyr Gly Met
            100                 105                 110

Asp Val Trp Gly Gln Gly Thr Thr Val Thr Val Ser Ser
        115                 120                 125

<210> SEQ ID NO 203
<211> LENGTH: 24
<212> TYPE: DNA
<213> ORGANISM: Artificial Sequence
<220> FEATURE:
<223> OTHER INFORMATION: Synthetic

<400> SEQUENCE: 203
ggattcacct ttagcagata tgac                                          24

<210> SEQ ID NO 204
<211> LENGTH: 8
<212> TYPE: PRT
<213> ORGANISM: Artificial Sequence
<220> FEATURE:
<223> OTHER INFORMATION: Synthetic

<400> SEQUENCE: 204

Gly Phe Thr Phe Ser Arg Tyr Asp
1               5

<210> SEQ ID NO 205
<211> LENGTH: 24
<212> TYPE: DNA
<213> ORGANISM: Artificial Sequence
<220> FEATURE:
<223> OTHER INFORMATION: Synthetic

<400> SEQUENCE: 205
atttcttata gtggtgacag caca                                          24

<210> SEQ ID NO 206
<211> LENGTH: 8
<212> TYPE: PRT
<213> ORGANISM: Artificial Sequence
<220> FEATURE:
<223> OTHER INFORMATION: Synthetic

<400> SEQUENCE: 206

Ile Ser Tyr Ser Gly Asp Ser Thr
```

<210> SEQ ID NO 207
<211> LENGTH: 54
<212> TYPE: DNA
<213> ORGANISM: Artificial Sequence
<220> FEATURE:
<223> OTHER INFORMATION: Synthetic

<400> SEQUENCE: 207
gcgaaagata atgggtatag tgggacctac tactactact acggtatgga cgtc        54

<210> SEQ ID NO 208
<211> LENGTH: 18
<212> TYPE: PRT
<213> ORGANISM: Artificial Sequence
<220> FEATURE:
<223> OTHER INFORMATION: Synthetic

<400> SEQUENCE: 208

Ala Lys Asp Asn Gly Tyr Ser Gly Thr Tyr Tyr Tyr Tyr Gly Met
1               5                   10                  15

Asp Val

<210> SEQ ID NO 209
<211> LENGTH: 321
<212> TYPE: DNA
<213> ORGANISM: Artificial Sequence
<220> FEATURE:
<223> OTHER INFORMATION: Synthetic

<400> SEQUENCE: 209
gacatccaga tgacccagtc tccatcctca ctgtctgcat ctgtaggaga cagagtcacc     60
atcacttgtc gggcgagtca gggcattagc aattacttag cctggtttca gcagaaacca    120
gggaaagccc ctaagttcct gatttatgct gcatccagtt tgcaaagtgg ggtcccatca    180
aagttcagcg gcagtggatc tgggacagat ttcactctca ccatcagcag cctgcagcct    240
gaagattttg caacttatta ctgccaacaa tataatagtt acccgtacac ttttggccag    300
gggaccaagc tggagatcaa a                                              321

<210> SEQ ID NO 210
<211> LENGTH: 107
<212> TYPE: PRT
<213> ORGANISM: Artificial Sequence
<220> FEATURE:
<223> OTHER INFORMATION: Synthetic

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Phe Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
        100               105

<210> SEQ ID NO 211
<211> LENGTH: 18
<212> TYPE: DNA
<213> ORGANISM: Artificial Sequence
<220> FEATURE:
<223> OTHER INFORMATION: Synthetic

<400> SEQUENCE: 211
cagggcatta gcaattac                                               18

<210> SEQ ID NO 212
<211> LENGTH: 6
<212> TYPE: PRT
<213> ORGANISM: Artificial Sequence
<220> FEATURE:
<223> OTHER INFORMATION: Synthetic

<400> SEQUENCE: 212

Gln Gly Ile Ser Asn Tyr
1             5

<210> SEQ ID NO 213
<211> LENGTH: 9
<212> TYPE: DNA
<213> ORGANISM: Artificial Sequence
<220> FEATURE:
<223> OTHER INFORMATION: Synthetic

<400> SEQUENCE: 213 gctgcatcc                                                           9

<210> SEQ ID NO 214
<211> LENGTH: 3
<212> TYPE: PRT
<213> ORGANISM: Artificial Sequence
<220> FEATURE:
<223> OTHER INFORMATION: Synthetic

<400> SEQUENCE: 214

Ala Ala Ser
1

<210> SEQ ID NO 215
<211> LENGTH: 27
<212> TYPE: DNA
<213> ORGANISM: Artificial Sequence
<220> FEATURE:
<223> OTHER INFORMATION: Synthetic

<400> SEQUENCE: 215
caacaatata atagttaccc gtacact                                 27

<210> SEQ ID NO 216
<211> LENGTH: 9
<212> TYPE: PRT
<213> ORGANISM: Artificial Sequence
<220> FEATURE:
<223> OTHER INFORMATION: Synthetic

<400> SEQUENCE: 216

Gln Gln Tyr Asn Ser Tyr Pro Tyr Thr
1             5

<210> SEQ ID NO 217
<211> LENGTH: 1368
<212> TYPE: DNA
<213> ORGANISM: Artificial Sequence
<220> FEATURE:
<223> OTHER INFORMATION: Synthetic

<400> SEQUENCE: 217

```
gaggtgcagc tggtggagtc tgggggaggc ttggtgcagc ctggggggtc cctgagactc      60
tcctgtgcag cctctggatt cacctttagc agatatgaca tgagctgggt ccgccaggct     120
ccagggaagg ggctagagtg ggtctcagct atttcttata gtggtgacag cacatactac     180
gcagactccg tgcagggccg gttcaccata tctagagaca attccaagaa tacgctgtat     240
ctgcaaatga acagtctgag agccgaggac acggcttat atcactgtgc gaaagataat     300
gggtatagtg ggacctacta ctactactac ggtatggacg tctggggcca agggaccacg     360
gtcaccgtct cctcagcctc caccaagggc ccatcggtct tccccctggc accctcctcc     420
aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagaaagttg agcccaaatc ttgtgacaaa actcacacat gcccaccgtg cccagcacct     720
gaactcctgg ggggaccgtc agtcttcctc ttccccccaa aacccaagga caccctcatg     780
atctcccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgtgtg gtcagcgtcc tcaccgtcct gcaccaggac     960
tggctgaatg gcaaggagta caagtgcaag gtctccaaca aagccctccc agcccccatc    1020
gagaaaacca tctccaaagc caaagggcag ccccgagaac cacaggtgta caccctgccc    1080
ccatcccggg atgagctgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacgcagaa gtccctctcc ctgtctccgg gtaaatga                 1368
```

<210> SEQ ID NO 218
<211> LENGTH: 455
<212> TYPE: PRT
<213> ORGANISM: Artificial Sequence
<220> FEATURE:
<223> OTHER INFORMATION: Synthetic

<400> SEQUENCE: 218

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Asp Met Ser Trp Val Arg Gln Ala Pro Gly Lys Gly Leu Glu Trp Val
        35                  40                  45

Ser Ala Ile Ser Tyr Ser Gly Asp Ser Thr Tyr Tyr Ala Asp Ser Val
    50                  55                  60

Gln Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Leu Tyr His Cys
                85                  90                  95

Ala Lys Asp Asn Gly Tyr Ser Gly Thr Tyr Tyr Tyr Tyr Gly Met
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 219
<211> LENGTH: 645
<212> TYPE: DNA
<213> ORGANISM: Artificial Sequence
<220> FEATURE:
```

<223> OTHER INFORMATION: Synthetic

<400> SEQUENCE: 219

```
gacatccaga tgacccagtc tccatcctca ctgtctgcat ctgtaggaga cagagtcacc    60
atcacttgtc gggcgagtca gggcattagc aattacttag cctggtttca gcagaaacca   120
gggaaagccc ctaagttcct gatttatgct gcatccagtt tgcaaagtgg ggtcccatca   180
aagttcagcg gcagtggatc tgggacagat ttcactctca ccatcagcag cctgcagcct   240
gaagattttg caacttatta ctgccaacaa tataatagtt acccgtacac ttttggccag   300
gggaccaagc tggagatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                   645
```

<210> SEQ ID NO 220
<211> LENGTH: 214
<212> TYPE: PRT
<213> ORGANISM: Artificial Sequence
<220> FEATURE:
<223> OTHER INFORMATION: Synthetic

<400> SEQUENCE: 220

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Phe Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 221
<211> LENGTH: 375
<212> TYPE: DNA
<213> ORGANISM: Artificial Sequence
<220> FEATURE:
<223> OTHER INFORMATION: Synthetic

<400> SEQUENCE: 221

```
caggtgcagc tgcaggagtc gggcccagga ctggtgaagc cttcggagac cctgtccctc    60
acctgcactg tctctggtgg ctccatcagt ggttacttct ggggctgggt ccggcagccc   120
ccagggaagg gactggaatg gattggatat atcttttaca gtgggagtac caattacaac   180
ccctccctca agagtcgaat caccttgtca gttgacacgt ccaagaacca gttctccctg   240
aaactgagct ctgtgaccgc cgcagacacg gccatatatt actgtgcgag acacagggaa   300
tactatggtt cgggaaatta tcggtactac gctttggacg tctggggcca agggaccacg   360
gtcaccgtct cctca                                                   375
```

<210> SEQ ID NO 222
<211> LENGTH: 125
<212> TYPE: PRT
<213> ORGANISM: Artificial Sequence
<220> FEATURE:
<223> OTHER INFORMATION: Synthetic

<400> SEQUENCE: 222

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Gly Tyr
            20                  25                  30

Phe Trp Gly Trp Val Arg Gln Pro Pro Gly Lys Gly Leu Glu Trp Ile
        35                  40                  45

Gly Tyr Ile Phe Tyr Ser Gly Ser Thr Asn Tyr Asn Pro Ser Leu Lys
    50                  55                  60

Ser Arg Ile Thr Leu Ser Val Asp Thr Ser Lys Asn Gln Phe Ser Leu
65                  70                  75                  80

Lys Leu Ser Ser Val Thr Ala Ala Asp Thr Ala Ile Tyr Tyr Cys Ala
                85                  90                  95

Arg His Arg Glu Tyr Tyr Gly Ser Gly Asn Tyr Arg Tyr Tyr Ala Leu
            100                 105                 110

Asp Val Trp Gly Gln Gly Thr Thr Val Thr Val Ser Ser
        115                 120                 125

<210> SEQ ID NO 223
<211> LENGTH: 24
<212> TYPE: DNA
<213> ORGANISM: Artificial Sequence
<220> FEATURE:
<223> OTHER INFORMATION: Synthetic

<400> SEQUENCE: 223

```
ggtggctcca tcagtggtta cttc                                           24
```

<210> SEQ ID NO 224
<211> LENGTH: 8
<212> TYPE: PRT
<213> ORGANISM: Artificial Sequence
<220> FEATURE:
<223> OTHER INFORMATION: Synthetic

<400> SEQUENCE: 224

Gly Gly Ser Ile Ser Gly Tyr Phe
1               5

<210> SEQ ID NO 225
<211> LENGTH: 21
<212> TYPE: DNA
<213> ORGANISM: Artificial Sequence
<220> FEATURE:
<223> OTHER INFORMATION: Synthetic

<400> SEQUENCE: 225
atcttttaca gtgggagtac c                                               21

<210> SEQ ID NO 226
<211> LENGTH: 7
<212> TYPE: PRT
<213> ORGANISM: Artificial Sequence
<220> FEATURE:
<223> OTHER INFORMATION: Synthetic

<400> SEQUENCE: 226

Ile Phe Tyr Ser Gly Ser Thr
1               5

<210> SEQ ID NO 227
<211> LENGTH: 57
<212> TYPE: DNA
<213> ORGANISM: Artificial Sequence
<220> FEATURE:
<223> OTHER INFORMATION: Synthetic

<400> SEQUENCE: 227
gcgagacaca gggaatacta tggttcggga aattatcggt actacgcttt ggacgtc       57

<210> SEQ ID NO 228
<211> LENGTH: 19
<212> TYPE: PRT
<213> ORGANISM: Artificial Sequence
<220> FEATURE:
<223> OTHER INFORMATION: Synthetic

<400> SEQUENCE: 228

Ala Arg His Arg Glu Tyr Tyr Gly Ser Gly Asn Tyr Arg Tyr Tyr Ala
1               5                   10                  15
Leu Asp Val

<210> SEQ ID NO 229
<211> LENGTH: 321
<212> TYPE: DNA
<213> ORGANISM: Artificial Sequence
<220> FEATURE:
<223> OTHER INFORMATION: Synthetic

<400> SEQUENCE: 229
gccatccaga tgacccagtc tccatcctcc ctgtctgcgt ctgtaggaga cagagtcacc     60
atcacttgcc gggcaagtca gggcattaga gatgatttag ctggtatca gcagaaacca    120 gggaaagccc ctaagctcct gatctatgct gcatccagtt tacaaagtgg ggtcccatca   180
aggttcagcg gcagtggatc tggcacagat ttcactctca ccatcagcag cctgcagcct   240
gaagattttg caacttatta ctgtctacaa gattataatt tcccgttgac gttcggccaa   300
gggaccaagg tggaaatcaa a                                              321

<210> SEQ ID NO 230

<211> LENGTH: 107
<212> TYPE: PRT
<213> ORGANISM: Artificial Sequence
<220> FEATURE:
<223> OTHER INFORMATION: Synthetic

<400> SEQUENCE: 230

```
Ala Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asp Asp
            20                  25                  30
Leu Gly Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Leu Gln Asp Tyr Asn Phe Pro Leu
                85                  90                  95
Thr Phe Gly Gln Gly Thr Lys Val Glu Ile Lys
            100                 105
```

<210> SEQ ID NO 231
<211> LENGTH: 18
<212> TYPE: DNA
<213> ORGANISM: Artificial Sequence
<220> FEATURE:
<223> OTHER INFORMATION: Synthetic

<400> SEQUENCE: 231
cagggcatta gagatgat                                                   18

<210> SEQ ID NO 232
<211> LENGTH: 6
<212> TYPE: PRT
<213> ORGANISM: Artificial Sequence
<220> FEATURE:
<223> OTHER INFORMATION: Synthetic

<400> SEQUENCE: 232

```
Gln Gly Ile Arg Asp Asp
1               5
```

<210> SEQ ID NO 233
<211> LENGTH: 9
<212> TYPE: DNA
<213> ORGANISM: Artificial Sequence
<220> FEATURE:
<223> OTHER INFORMATION: Synthetic

<400> SEQUENCE: 233 gctgcatcc                                                              9

<210> SEQ ID NO 234
<211> LENGTH: 3
<212> TYPE: PRT
<213> ORGANISM: Artificial Sequence
<220> FEATURE:
<223> OTHER INFORMATION: Synthetic

<400> SEQUENCE: 234

```
Ala Ala Ser
1
```

<210> SEQ ID NO 235
<211> LENGTH: 27
<212> TYPE: DNA
<213> ORGANISM: Artificial Sequence
<220> FEATURE:
<223> OTHER INFORMATION: Synthetic

<400> SEQUENCE: 235
ctacaagatt ataatttccc gttgacg                                    27

<210> SEQ ID NO 236
<211> LENGTH: 9
<212> TYPE: PRT
<213> ORGANISM: Artificial Sequence
<220> FEATURE:
<223> OTHER INFORMATION: Synthetic

<400> SEQUENCE: 236

Leu Gln Asp Tyr Asn Phe Pro Leu Thr
1               5

<210> SEQ ID NO 237
<211> LENGTH: 1368
<212> TYPE: DNA
<213> ORGANISM: Artificial Sequence
<220> FEATURE:
<223> OTHER INFORMATION: Synthetic

<400> SEQUENCE: 237
caggtgcagc tgcaggagtc gggcccagga ctggtgaagc cttcggagac cctgtccctc    60
acctgcactg tctctggtgg ctccatcagt ggttacttct ggggctgggt ccggcagccc   120
ccagggaagg gactggaatg gattggatat atcttttaca gtgggagtac caattacaac   180
ccctccctca agagtcgaat caccttgtca gttgacacgt ccaagaacca gttctccctg   240
aaactgagct ctgtgaccgc cgcagacacg gccatatatt actgtgcgag acacagggaa   300
tactatggtt cgggaaatta tcggtactac gctttggacg tctggggcca agggaccacg   360
gtcaccgtct cctcagcctc caccaagggc ccatcggtct tccccctggc accctcctcc   420
aagagcacct ctgggggcac agcggccctg ggctgcctgg tcaaggacta cttccccgaa   480
ccggtgacgg tgtcgtggaa ctcaggcgcc ctgaccagcg gcgtgcacac cttcccggct   540
gtcctacagt cctcaggact ctactccctc agcagcgtgg tgaccgtgcc ctccagcagc   600
ttgggcaccc agacctacat ctgcaacgtg aatcacaagc ccagcaacac caaggtggac   660
aagaaagttg agcccaaatc ttgtgacaaa actcacacat gcccaccgtg cccagcacct   720
gaactcctgg ggggaccgtc agtcttcctc ttccccccaa aacccaagga caccctcatg   780
atctcccgga cccctgaggt cacatgcgtg gtggtggacg tgagccacga agaccctgag   840
gtcaagttca actggtacgt ggacggcgtg gaggtgcata atgccaagac aaagccgcgg   900
gaggagcagt acaacagcac gtaccgtgtg gtcagcgtcc tcaccgtcct gcaccaggac   960
tggctgaatg gcaaggagta caagtgcaag gtctccaaca agccctccc  agcccccatc  1020
gagaaaacca tctccaaagc caaagggcag ccccgagaac cacaggtgta caccctgccc  1080
ccatcccggg atgagctgac caagaaccag gtcagcctga cctgcctggt caaaggcttc  1140
tatcccagcg acatcgccgt ggagtgggag agcaatgggc agccggagaa caactacaag  1200
accacgcctc ccgtgctgga ctccgacggc tccttcttcc tctacagcaa gctcaccgtg  1260
gacaagagca ggtggcagca ggggaacgtc ttctcatgct ccgtgatgca tgaggctctg  1320
cacaaccact acacgcagaa gtccctctcc ctgtctccgg gtaaatga          1368

<210> SEQ ID NO 238
<211> LENGTH: 455
<212> TYPE: PRT
<213> ORGANISM: Artificial Sequence
<220> FEATURE:
<223> OTHER INFORMATION: Synthetic

<400> SEQUENCE: 238

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Gly Tyr
             20                  25                  30

Phe Trp Gly Trp Val Arg Gln Pro Pro Gly Lys Gly Leu Glu Trp Ile
         35                  40                  45

Gly Tyr Ile Phe Tyr Ser Gly Ser Thr Asn Tyr Asn Pro Ser Leu Lys
     50                  55                  60

Ser Arg Ile Thr Leu Ser Val Asp Thr Ser Lys Asn Gln Phe Ser Leu
 65                  70                  75                  80

Lys Leu Ser Ser Val Thr Ala Ala Asp Thr Ala Ile Tyr Tyr Cys Ala
                 85                  90                  95

Arg His Arg Glu Tyr Tyr Gly Ser Gly Asn Tyr Arg Tyr Tyr Ala Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
```

```
                355                 360                 365
Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
                450                 455

<210> SEQ ID NO 239
<211> LENGTH: 645
<212> TYPE: DNA
<213> ORGANISM: Artificial Sequence
<220> FEATURE:
<223> OTHER INFORMATION: Synthetic

<400> SEQUENCE: 239
gccatccaga tgacccagtc tccatcctcc ctgtctgcgt ctgtaggaga cagagtcacc       60
atcacttgcc gggcaagtca gggcattaga gatgatttag ctggtatca gcagaaacca      120 gggaaagccc ctaagctcct gatctatgct gcatccagtt tacaaagtgg ggtcccatca      180
aggttcagcg gcagtggatc tggcacagat ttcactctca ccatcagcag cctgcagcct      240
gaagattttg caacttatta ctgtctacaa gattataatt tcccgttgac gttcggccaa      300
gggaccaagg tggaaatcaa acgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga aaacacaaa gtctacgcct gcgaagtcac ccatcagggc      600
ctgagctcgc ccgtcacaaa gagcttcaac aggggagagt gttag                     645

<210> SEQ ID NO 240
<211> LENGTH: 214
<212> TYPE: PRT
<213> ORGANISM: Artificial Sequence
<220> FEATURE:
<223> OTHER INFORMATION: Synthetic

<400> SEQUENCE: 240

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asp Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Phe Pro Leu
                85                  90                  95
```

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 241
<211> LENGTH: 357
<212> TYPE: DNA
<213> ORGANISM: Artificial Sequence
<220> FEATURE:
<223> OTHER INFORMATION: Synthetic

<400> SEQUENCE: 241
gaggtgcagc tggtggagtc tgggggagac ttggtacagc ctggagggtc cctgagactc      60
tcctgtgcag cctctggatt caccttcagt agttttgaga tgaactgggt ccgccaggct     120
ccagggaagg gctggagtg gtttcatac attagtagta gtggtagcac catttattat      180
gcagactctg tgaaggaccg attcaccgtc tccagagaca agacaagaa ttcactgtat      240 ctgcaaatga acagcctgag agccgaggac acggctgtgt attactgtgc gagagggagc     300
tggaaccaac cttactttga ctactggggc cagggaaccc tggtcaccgt ctcctca        357

<210> SEQ ID NO 242
<211> LENGTH: 119
<212> TYPE: PRT
<213> ORGANISM: Artificial Sequence
<220> FEATURE:
<223> OTHER INFORMATION: Synthetic

<400> SEQUENCE: 242

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Phe
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Asp Arg Phe Thr Val Ser Arg Asp Lys Asp Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Asn Gln Pro Tyr Phe Asp Tyr Trp Gly Gln Gly
            100                 105                 110

Thr Leu Val Thr Val Ser Ser

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct tcagtagttt tgag                                        24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Phe Ser Ser Phe Glu
1               5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
attagtagta gtggtagcac catt                                        24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Ser Ser Ser Gly Ser Thr Ile
1               5

<210> SEQ ID NO 247
<211> LENGTH: 36
<212> TYPE: DNA
<213> ORGANISM: Artificial Sequence
<220> FEATURE:
<223> OTHER INFORMATION: Synthetic

<400> SEQUENCE: 247
gcgagaggga gctggaacca accttacttt gactac                           36

<210> SEQ ID NO 248
<211> LENGTH: 12
<212> TYPE: PRT
<213> ORGANISM: Artificial Sequence
<220> FEATURE:
<223> OTHER INFORMATION: Synthetic

<400> SEQUENCE: 248

Ala Arg Gly Ser Trp Asn Gln Pro Tyr Phe Asp Tyr
1               5                   10

<210> SEQ ID NO 249

<211> LENGTH: 315
<212> TYPE: DNA
<213> ORGANISM: Artificial Sequence
<220> FEATURE:
<223> OTHER INFORMATION: Synthetic

<400> SEQUENCE: 249

```
gacatccaga tgacccagtc tccttccacc ctgtctgcat ctgtcggaga cagagtcacc      60
atcacttgcc gggccagtca gagtattagt agctggttgg cctggtatca gctgaaacca     120
gggaaagccc ctaaggtcct gatctataag gcgtctagtt tagaaagtgg ggtcccatca     180
aggttcagcg gcagtggatc tgggacagaa ttcactctca ccatcaacag cctgcagcct     240
gatgattttg caacttatta ctgtcaacag tataatagtt ggactttcgg ccaagggacc     300
aaggtggaaa tcaaa                                                      315
```

<210> SEQ ID NO 250
<211> LENGTH: 105
<212> TYPE: PRT
<213> ORGANISM: Artificial Sequence
<220> FEATURE:
<223> OTHER INFORMATION: Synthetic

<400> SEQUENCE: 250

```
Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Ser Ser Trp
            20                  25                  30
Leu Ala Trp Tyr Gln Leu Lys Pro Gly Lys Ala Pro Lys Val Leu Ile
        35                  40                  45
Tyr Lys Ala Ser Ser Leu Glu Ser Gly Val Pro Ser Arg Phe Ser Gly
    50                  55                  60
Ser Gly Ser Gly Thr Glu Phe Thr Leu Thr Ile Asn Ser Leu Gln Pro
65                  70                  75                  80
Asp Asp Phe Ala Thr Tyr Tyr Cys Gln Gln Tyr Asn Ser Trp Thr Phe
                85                  90                  95
Gly Gln Gly Thr Lys Val Glu Ile Lys
            100                 105
```

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251

```
cagagtatta gtagctgg                                                    18
```

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

```
Gln Ser Ile Ser Ser Trp
1               5
```

<210> SEQ ID NO 253
<211> LENGTH: 9

<212> TYPE: DNA
<213> ORGANISM: Artificial Sequence
<220> FEATURE:
<223> OTHER INFORMATION: Synthetic

<400> SEQUENCE: 253 aaggcgtct                                                                9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Lys Ala Ser
1

<210> SEQ ID NO 255
<211> LENGTH: 21
<212> TYPE: DNA
<213> ORGANISM: Artificial Sequence
<220> FEATURE:
<223> OTHER INFORMATION: Synthetic

<400> SEQUENCE: 255
caacagtata atagttggac t                                                 21

<210> SEQ ID NO 256
<211> LENGTH: 7
<212> TYPE: PRT
<213> ORGANISM: Artificial Sequence
<220> FEATURE:
<223> OTHER INFORMATION: Synthetic

<400> SEQUENCE: 256

Gln Gln Tyr Asn Ser Trp Thr
1               5

<210> SEQ ID NO 257
<211> LENGTH: 1350
<212> TYPE: DNA
<213> ORGANISM: Artificial Sequence
<220> FEATURE:
<223> OTHER INFORMATION: Synthetic

<400> SEQUENCE: 257
gaggtgcagc tggtggagtc tgggggagac ttggtacagc ctggagggtc cctgagactc        60
tcctgtgcag cctctggatt caccttcagt agttttgaga tgaactgggt ccgccaggct       120
ccagggaagg ggctggagtg ggtttcatac attagtagta gtggtagcac catttattat       180
gcagactctg tgaaggaccg attcaccgtc tccagagaca agacaagaa ttcactgtat        240 ctgcaaatga acagcctgag agccgaggac acggctgtgt attactgtgc gagagggagc       300
tggaaccaac cttactttga ctactggggc cagggaaccc tggtcaccgt ctcctcagcc       360
tccaccaagg gcccatcggt cttccccctg gcaccctcct ccaagagcac ctctgggggc       420
acagcggccc tgggctgcct ggtcaaggac tacttccccg aaccggtgac ggtgtcgtgg       480
aactcaggcg ccctgaccag cggcgtgcac accttcccgg ctgtcctaca gtcctcagga       540
ctctactccc tcagcagcgt ggtgaccgtg ccctccagca gcttgggcac ccagacctac       600
atctgcaacg tgaatcacaa gcccagcaac accaaggtgg acaagaaagt tgagcccaaa       660

```
tcttgtgaca aaactcacac atgcccaccg tgcccagcac ctgaactcct ggggggaccg    720
tcagtcttcc tcttcccccc aaaacccaag acacccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa    1020
gccaaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagtccctct ccctgtctcc gggtaaatga                                    1350
```

<210> SEQ ID NO 258
<211> LENGTH: 449
<212> TYPE: PRT
<213> ORGANISM: Artificial Sequence
<220> FEATURE:
<223> OTHER INFORMATION: Synthetic

<400> SEQUENCE: 258

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Phe
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Asp Arg Phe Thr Val Ser Arg Asp Lys Asp Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Asn Gln Pro Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

| | | | | | | | | | | | |
|---|---|---|---|---|---|---|---|---|---|---|---|
|Ser|Val|Phe|Leu|Phe|Pro|Pro|Lys|Pro|Lys|Asp|Thr|Leu|Met|Ile|Ser|
| | | |245| | | |250| | | |255|

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

```
<210> SEQ ID NO 259
<211> LENGTH: 639
<212> TYPE: DNA
<213> ORGANISM: Artificial Sequence
<220> FEATURE:
<223> OTHER INFORMATION: Synthetic

<400> SEQUENCE: 259
gacatccaga tgacccagtc tccttccacc ctgtctgcat ctgtcggaga cagagtcacc      60
atcacttgcc gggccagtca gagtattagt agctggttgg cctggtatca gctgaaacca     120
gggaaagccc ctaaggtcct gatctataag gcgtctagtt tagaaagtgg ggtcccatca     180
aggttcagcg gcagtggatc tgggacagaa ttcactctca ccatcaacag cctgcagcct     240
gatgattttg caacttatta ctgtcaacag tataatagtt ggactttcgg ccaagggacc     300
aaggtggaaa tcaaacgaac tgtggctgca ccatctgtct tcatcttccc gccatctgat     360
gagcagttga aatctggaac tgcctctgtt gtgtgcctgc tgaataactt ctatcccaga     420
gaggccaaag tacagtggaa ggtggataac gccctccaat cgggtaactc ccaggagagt     480
gtcacagagc aggacagcaa ggacagcacc tacagcctca gcagcaccct gacgctgagc     540
aaagcagact acgagaaaca caaagtctac gcctgcgaag tcacccatca gggcctgagc     600
tcgcccgtca caaagagctt caacagggga gagtgttag                            639

<210> SEQ ID NO 260
<211> LENGTH: 212
<212> TYPE: PRT
<213> ORGANISM: Artificial Sequence
<220> FEATURE:
```

<223> OTHER INFORMATION: Synthetic

<400> SEQUENCE: 260

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Leu Lys Pro Gly Lys Ala Pro Lys Val Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln Tyr Asn Ser Trp Thr Phe
                85                  90                  95

Gly Gln Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 261
<211> LENGTH: 360
<212> TYPE: DNA
<213> ORGANISM: Artificial Sequence
<220> FEATURE:
<223> OTHER INFORMATION: Synthetic

<400> SEQUENCE: 261
caggtgcagc tggtggagtc tgggggaggc ttggtcaggc ctggagggtc cctgagactc      60
tcctgtgaag cctctggatt caccttcaat gaacactaca tgagctggat ccgccaggct     120
ccagggaagg gctggagtg ggttgcattc attagtagtg gtggtagtat tatttactat     180
gcagactctg tgaagggccg attcaccata tcgagggaca gcgccaagaa ttcactgtat     240
cttcaaatga acagcctgag acccgaggac acggccattt attactgtgc gagagagccg     300
tttgggggaa ttatcgtctt tgactactgg ggccagggca ccctggtcac cgtctcctca     360

<210> SEQ ID NO 262
<211> LENGTH: 120
<212> TYPE: PRT
<213> ORGANISM: Artificial Sequence
<220> FEATURE:
<223> OTHER INFORMATION: Synthetic

<400> SEQUENCE: 262

Gln Val Gln Leu Val Glu Ser Gly Gly Gly Leu Val Arg Pro Gly Gly

```
                1               5                  10                  15
            Ser Leu Arg Leu Ser Cys Glu Ala Ser Gly Phe Thr Phe Asn Glu His
                        20                  25                  30

Tyr Met Ser Trp Ile Arg Gln Ala Pro Gly Lys Gly Leu Glu Trp Val
                        35                  40                  45

Ala Phe Ile Ser Ser Gly Gly Ser Ile Ile Tyr Tyr Ala Asp Ser Val
                    50                  55                  60

Lys Gly Arg Phe Thr Ile Ser Arg Asp Ser Ala Lys Asn Ser Leu Tyr
            65                  70                  75                  80

Leu Gln Met Asn Ser Leu Arg Pro Glu Asp Thr Ala Ile Tyr Tyr Cys
                            85                  90                  95

Ala Arg Glu Pro Phe Gly Gly Ile Ile Val Phe Asp Tyr Trp Gly Gln
                        100                 105                 110

Gly Thr Leu Val Thr Val Ser Ser
                        115                 120
```

<210> SEQ ID NO 263
<211> LENGTH: 24
<212> TYPE: DNA
<213> ORGANISM: Artificial Sequence
<220> FEATURE:
<223> OTHER INFORMATION: Synthetic

<400> SEQUENCE: 263
ggattcacct tcaatgaaca ctac                                            24

<210> SEQ ID NO 264
<211> LENGTH: 8
<212> TYPE: PRT
<213> ORGANISM: Artificial Sequence
<220> FEATURE:
<223> OTHER INFORMATION: Synthetic

<400> SEQUENCE: 264

```
            Gly Phe Thr Phe Asn Glu His Tyr
            1               5
```

<210> SEQ ID NO 265
<211> LENGTH: 24
<212> TYPE: DNA
<213> ORGANISM: Artificial Sequence
<220> FEATURE:
<223> OTHER INFORMATION: Synthetic

<400> SEQUENCE: 265
attagtagtg gtggtagtat tatt                                            24

<210> SEQ ID NO 266
<211> LENGTH: 8
<212> TYPE: PRT
<213> ORGANISM: Artificial Sequence
<220> FEATURE:
<223> OTHER INFORMATION: Synthetic

<400> SEQUENCE: 266

```
            Ile Ser Ser Gly Gly Ser Ile Ile
            1               5
```

<210> SEQ ID NO 267
<211> LENGTH: 39
<212> TYPE: DNA
<213> ORGANISM: Artificial Sequence
<220> FEATURE:

<223> OTHER INFORMATION: Synthetic

<400> SEQUENCE: 267
gcgagagagc cgtttggggg aattatcgtc tttgactac                39

<210> SEQ ID NO 268
<211> LENGTH: 13
<212> TYPE: PRT
<213> ORGANISM: Artificial Sequence
<220> FEATURE:
<223> OTHER INFORMATION: Synthetic

<400> SEQUENCE: 268

Ala Arg Glu Pro Phe Gly Gly Ile Ile Val Phe Asp Tyr
1               5                   10

<210> SEQ ID NO 269
<211> LENGTH: 324
<212> TYPE: DNA
<213> ORGANISM: Artificial Sequence
<220> FEATURE:
<223> OTHER INFORMATION: Synthetic

<400> SEQUENCE: 269
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                            324

<210> SEQ ID NO 270
<211> LENGTH: 108
<212> TYPE: PRT
<213> ORGANISM: Artificial Sequence
<220> FEATURE:
<223> OTHER INFORMATION: Synthetic

<400> SEQUENCE: 270

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 271
<211> LENGTH: 18
<212> TYPE: DNA
<213> ORGANISM: Artificial Sequence
<220> FEATURE:
<223> OTHER INFORMATION: Synthetic

<400> SEQUENCE: 271
cagagcatta gcagctat                                                     18

<210> SEQ ID NO 272
<211> LENGTH: 6
<212> TYPE: PRT
<213> ORGANISM: Artificial Sequence
<220> FEATURE:
<223> OTHER INFORMATION: Synthetic

<400> SEQUENCE: 272

Gln Ser Ile Ser Ser Tyr
1               5

<210> SEQ ID NO 273
<211> LENGTH: 9
<212> TYPE: DNA
<213> ORGANISM: Artificial Sequence
<220> FEATURE:
<223> OTHER INFORMATION: Synthetic

<400> SEQUENCE: 273 gctgcatcc                                                                9

<210> SEQ ID NO 274
<211> LENGTH: 3
<212> TYPE: PRT
<213> ORGANISM: Artificial Sequence
<220> FEATURE:
<223> OTHER INFORMATION: Synthetic

<400> SEQUENCE: 274

Ala Ala Ser
1

<210> SEQ ID NO 275
<211> LENGTH: 30
<212> TYPE: DNA
<213> ORGANISM: Artificial Sequence
<220> FEATURE:
<223> OTHER INFORMATION: Synthetic

<400> SEQUENCE: 275
caacagagtt acagtacccc tccgatcacc                                        30

<210> SEQ ID NO 276
<211> LENGTH: 10
<212> TYPE: PRT
<213> ORGANISM: Artificial Sequence
<220> FEATURE:
<223> OTHER INFORMATION: Synthetic

<400> SEQUENCE: 276

Gln Gln Ser Tyr Ser Thr Pro Pro Ile Thr
1               5                   10

<210> SEQ ID NO 277
<211> LENGTH: 1353
<212> TYPE: DNA
<213> ORGANISM: Artificial Sequence
<220> FEATURE:
<223> OTHER INFORMATION: Synthetic

<400> SEQUENCE: 277
caggtgcagc tggtggagtc tgggggaggc ttggtcaggc ctggagggtc cctgagactc        60

```
tcctgtgaag cctctggatt caccttcaat gaacactaca tgagctggat ccgccaggct    120
ccagggaagg ggctggagtg ggttgcattc attagtagtg gtggtagtat tatttactat    180
gcagactctg tgaagggccg attcaccata tcgaggaca gcgccaagaa ttcactgtat    240
cttcaaatga acagcctgag acccgaggac acggccattt attactgtgc gagagagccg    300
tttgggggaa ttatcgtctt tgactactgg ggccagggca ccctggtcac cgtctcctca    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctggggga    720 ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc    1020
aaagccaaag ggcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagtccc tctccctgtc tccgggtaaa tga                                 1353
```

<210> SEQ ID NO 278
<211> LENGTH: 450
<212> TYPE: PRT
<213> ORGANISM: Artificial Sequence
<220> FEATURE:
<223> OTHER INFORMATION: Synthetic

<400> SEQUENCE: 278

```
Gln Val Gln Leu Val Glu Ser Gly Gly Gly Leu Val Arg Pro Gly Gly
1               5                   10                  15

Ser Leu Arg Leu Ser Cys Glu Ala Ser Gly Phe Thr Phe Asn Glu His
            20                  25                  30

Tyr Met Ser Trp Ile Arg Gln Ala Pro Gly Lys Gly Leu Glu Trp Val
        35                  40                  45

Ala Phe Ile Ser Ser Gly Gly Ser Ile Ile Tyr Tyr Ala Asp Ser Val
    50                  55                  60

Lys Gly Arg Phe Thr Ile Ser Arg Asp Ser Ala Lys Asn Ser Leu Tyr
65                  70                  75                  80

Leu Gln Met Asn Ser Leu Arg Pro Glu Asp Thr Ala Ile Tyr Tyr Cys
                85                  90                  95

Ala Arg Glu Pro Phe Gly Gly Ile Ile Val Phe Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 279
<211> LENGTH: 648
<212> TYPE: DNA
<213> ORGANISM: Artificial Sequence
<220> FEATURE:
<223> OTHER INFORMATION: Synthetic

<400> SEQUENCE: 279
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccgtca     180
```

```
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttag                648
```

<210> SEQ ID NO 280
<211> LENGTH: 215
<212> TYPE: PRT
<213> ORGANISM: Artificial Sequence
<220> FEATURE:
<223> OTHER INFORMATION: Synthetic

<400> SEQUENCE: 280

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 281
<211> LENGTH: 363
<212> TYPE: DNA
<213> ORGANISM: Artificial Sequence
<220> FEATURE:
<223> OTHER INFORMATION: Synthetic

<400> SEQUENCE: 281

```
caggtgcagc tgcaggagtc gggcctagga ctggtgaaac cttcggagac cctgtccctc     60
```

```
acttgcactg tctcgggtga ctccatcggt acttactact ggagctggat ccggcagccc    120
ccagggaagg gactggagtg gattgcgtat atttatgaca gtaggcacag caattccaat    180
ccttccctca agagtcgagt caccacatca gtagacatgt ccaagaacca gttctccctg    240
caattaaagt ctgtgaccgc tgcggacacg gccgtatatt tttgtgcgag agattgggga    300
acctggaagc cgagggtgc ttttgatatc tggggccaag ggacaatggt caccgtctct    360
tca                                                                 363
```

<210> SEQ ID NO 282
<211> LENGTH: 121
<212> TYPE: PRT
<213> ORGANISM: Artificial Sequence
<220> FEATURE:
<223> OTHER INFORMATION: Synthetic

<400> SEQUENCE: 282

```
Gln Val Gln Leu Gln Glu Ser Gly Leu Gly Leu Val Lys Pro Ser Glu
1               5                   10                  15

Thr Leu Ser Leu Thr Cys Thr Val Ser Gly Asp Ser Ile Gly Thr Tyr
            20                  25                  30

Tyr Trp Ser Trp Ile Arg Gln Pro Pro Gly Lys Gly Leu Glu Trp Ile
        35                  40                  45

Ala Tyr Ile Tyr Asp Ser Arg His Ser Asn Ser Asn Pro Ser Leu Lys
    50                  55                  60

Ser Arg Val Thr Thr Ser Val Asp Met Ser Lys Asn Gln Phe Ser Leu
65                  70                  75                  80

Gln Leu Lys Ser Val Thr Ala Ala Asp Thr Ala Val Tyr Phe Cys Ala
                85                  90                  95

Arg Asp Trp Gly Thr Trp Lys Pro Glu Gly Ala Phe Asp Ile Trp Gly
            100                 105                 110

Gln Gly Thr Met Val Thr Val Ser Ser
        115                 120
```

<210> SEQ ID NO 283
<211> LENGTH: 24
<212> TYPE: DNA
<213> ORGANISM: Artificial Sequence
<220> FEATURE:
<223> OTHER INFORMATION: Synthetic

<400> SEQUENCE: 283

```
ggtgactcca tcggtactta ctac                                           24
```

<210> SEQ ID NO 284
<211> LENGTH: 8
<212> TYPE: PRT
<213> ORGANISM: Artificial Sequence
<220> FEATURE:
<223> OTHER INFORMATION: Synthetic

<400> SEQUENCE: 284

```
Gly Asp Ser Ile Gly Thr Tyr Tyr
1               5
```

<210> SEQ ID NO 285
<211> LENGTH: 21
<212> TYPE: DNA
<213> ORGANISM: Artificial Sequence
<220> FEATURE:
<223> OTHER INFORMATION: Synthetic

<400> SEQUENCE: 285
atttatgaca gtaggcacag c                                                    21

<210> SEQ ID NO 286
<211> LENGTH: 7
<212> TYPE: PRT
<213> ORGANISM: Artificial Sequence
<220> FEATURE:
<223> OTHER INFORMATION: Synthetic

<400> SEQUENCE: 286

Ile Tyr Asp Ser Arg His Ser
1               5

<210> SEQ ID NO 287
<211> LENGTH: 45
<212> TYPE: DNA
<213> ORGANISM: Artificial Sequence
<220> FEATURE:
<223> OTHER INFORMATION: Synthetic

<400> SEQUENCE: 287
gcgagagatt ggggaacctg gaagcccgag ggtgcttttg atatc            45

<210> SEQ ID NO 288
<211> LENGTH: 15
<212> TYPE: PRT
<213> ORGANISM: Artificial Sequence
<220> FEATURE:
<223> OTHER INFORMATION: Synthetic

<400> SEQUENCE: 288

Ala Arg Asp Trp Gly Thr Trp Lys Pro Glu Gly Ala Phe Asp Ile
1               5                   10                  15

<210> SEQ ID NO 289
<211> LENGTH: 1356
<212> TYPE: DNA
<213> ORGANISM: Artificial Sequence
<220> FEATURE:
<223> OTHER INFORMATION: Synthetic

<400> SEQUENCE: 289
caggtgcagc tgcaggagtc gggcctagga ctggtgaaac cttcggagac cctgtccctc    60
acttgcactg tctcgggtga ctccatcggt acttactact ggagctggat ccggcagccc   120
ccagggaagg gactggagtg gattgcgtat atttatgaca gtaggcacag caattccaat   180
ccttccctca agagtcgagt caccacatca gtagacatgt ccaagaacca gttctccctg   240
caattaaagt ctgtgaccgc tgcggacacg gccgtatatt tttgtgcgag agattgggga   300
acctggaagc cgagggtgc ttttgatatc tggggccaag gacaatggt caccgtctct   360 tcagcctcca ccaagggccc atcggtcttc cccctggcac cctcctccaa gagcacctct   420
gggggcacag cggccctggg ctgcctggtc aaggactact tccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gaaagttgag   660
cccaaatctt gtgacaaaac tcacacatgc ccaccgtgcc cagcacctga actcctgggg   720
ggaccgtcag tcttcctctt ccccccaaaa cccaaggaca cctcatgat ctcccggacc   780

```
cctgaggtca catgcgtggt ggtggacgtg agccacgaag accctgaggt caagttcaac      840
tggtacgtgg acggcgtgga ggtgcataat gccaagacaa agccgcggga ggagcagtac      900
aacagcacgt accgtgtggt cagcgtcctc accgtcctgc accaggactg gctgaatggc      960
aaggagtaca agtgcaaggt ctccaacaaa gccctcccag cccccatcga gaaaaccatc     1020
tccaaagcca aagggcagcc ccgagaacca caggtgtaca ccctgccccc atcccgggat     1080
gagctgacca agaaccaggt cagcctgacc tgcctggtca aaggcttcta tcccagcgac     1140
atcgccgtgg agtgggagag caatgggcag ccggagaaca actacaagac cacgcctccc     1200
gtgctggact ccgacggctc cttcttcctc tacagcaagc tcaccgtgga caagagcagg     1260
tggcagcagg ggaacgtctt ctcatgctcc gtgatgcatg aggctctgca caaccactac     1320
acgcagaagt ccctctcccc tgtctccggg taaatga                              1356
```

<210> SEQ ID NO 290
<211> LENGTH: 451
<212> TYPE: PRT
<213> ORGANISM: Artificial Sequence
<220> FEATURE:
<223> OTHER INFORMATION: Synthetic

<400> SEQUENCE: 290

```
Gln Val Gln Leu Gln Glu Ser Gly Leu Gly Leu Val Lys Pro Ser Glu
1               5                   10                  15

Thr Leu Ser Leu Thr Cys Thr Val Ser Gly Asp Ser Ile Gly Thr Tyr
            20                  25                  30

Tyr Trp Ser Trp Ile Arg Gln Pro Gly Lys Gly Leu Glu Trp Ile
        35                  40                  45

Ala Tyr Ile Tyr Asp Ser Arg His Ser Asn Ser Asn Pro Ser Leu Lys
    50                  55                  60

Ser Arg Val Thr Thr Ser Val Asp Met Ser Lys Asn Gln Phe Ser Leu
65                  70                  75                  80

Gln Leu Lys Ser Val Thr Ala Ala Asp Thr Ala Val Tyr Phe Cys Ala
                85                  90                  95

Arg Asp Trp Gly Thr Trp Lys Pro Glu Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
```

-continued

```
              260                 265                 270
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450
```

HUMAN ANTIBODIES TO *S. AUREUS* HEMOLYSIN A TOXIN

CROSS-REFERENCE TO RELATED APPLICATION

This application is a continuation of U.S. application Ser. No. 16/575,755, filed Sep. 19, 2019, which is a division of U.S. application Ser. No. 15/860,174, filed Jan. 2, 2018, now U.S. Pat. No. 10,463,748, which claims the benefit under 35 USC § 119(e) of U.S. Provisional Patent Application No. 62/441,786, filed Jan. 3, 2017, each of which is herein incorporated by reference in its entirety.

REFERENCE TO A SEQUENCE LISTING

This application incorporates by reference the Sequence Listing submitted in computer readable form as file 10268US03-Sequence.txt, created on Jan. 27, 2021, and containing 198,402 bytes.

FIELD OF THE INVENTION

The present invention is related to human antibodies and antigen-binding fragments thereof that specifically bind to *Staphylococcus aureus* Hemolysin A toxin, and to therapeutic and diagnostic methods of using such antibodies and fragments.

BACKGROUND

*Staphylococcus aureus* is a Gram-positive, facultative aerobic bacterium that often colonizes the skin and nose of healthy individuals. The bacterium is considered an opportunistic pathogen and can cause a variety of diseases/conditions in a number of body sites. It is a leading cause of bloodstream, skin and soft tissue and respiratory infections worldwide. The frequency of healthcare and community-associated infections caused by *S. aureus* has been increasing and efforts to combat these infections have been hampered by the emergence of drug-resistant strains, particularly the methicillin-resistant or MRSA strains.

*S. aureus* expresses a number of virulence factors (both cell surface expressed and secreted) that aid in bacterial invasion and dissemination in the host. Among the secreted virulence factors are a number of toxins, the most prominent of which is the pore-forming toxin Hemolysin A. *S. aureus* Hemolysin A is a 33 kDa secreted monomer that oligomerizes into a heptameric structure in the membrane of host cells to form a pore leading to cell lysis, epithelial barrier disruption, inflammation, and tissue damage (Berube et al., (2013), Toxins 5:1140-1166).

Multiple mammalian cell types, including platelets, monocytes, endothelial and epithelial cells, are lysed by Hemolysin A. It has been proposed that one or more of these cell types are the physiologically relevant targets of Hemolysin A rather than red blood cells (RBCs), as human RBCs are susceptible to lysis only when exposed to high concentrations of Hemolysin A (Hildebrand et al., (1991), J. Biol. Chem. 266:17195-17200; Wilke et al., (2010), Proc. Natl. Acad. Sci. USA 107:13473-13478; Berube et al., (2013), Toxins 5:1140-1166).

Hemolysin A has been shown to play a role in pneumonia, dermonecrosis, endocarditis, and sepsis in animal models of *S. aureus* infection (Tkaczyk et al., (2012), Clin. Vaccine Immunol. 19:377-385, and Kennedy et al., (2010), J. Infect. Dis. 202:1050-1058). *S. aureus* is a leading cause of skin and soft tissue infections (Moran, et al. (2006), N. Engl. J. Med. 355:666-674)), often causing cellulitis and skin abscesses. In mouse models, active immunization with a non-toxigenic form of Hemolysin A or passive immunization with Hemolysin A-specific antisera or monoclonal antibodies (mAbs) significantly reduces the size of skin lesions and prevents dermonecrosis caused by Hemolysin A-producing *S. aureus* strains (Kennedy et al., (2010), J. Infect. Dis. 202:1050-1058; Tkaczyk et al., (2012), Clin. Vaccine Immunol. 19:377-385). *S. aureus* is also a leading cause of pneumonia in hospitalized patients (Kollef et al., (2005), Chest 128:3854-3862 (Erratum in Chest 129:831); Shorr et al., (2006), Crit. Care 10:R97) and has been shown to play a role in mouse models of lung infection (Bubeck Wardenberg et al., (2007), Infect. Immun. 75:1040-1044). Active immunization with a non-toxigenic form of Hemolysin A or passive immunization with Hemolysin A-specific antisera or mAbs significantly reduces morbidity and mortality in mouse models of pneumonia (Bubeck Wardenburg and Schneewind, (2008), J. Exp. Med. 205:287-294; Hua et al., (2014), Antimicrob. Agents Chemother. 58:1108-1117).

*Staphylococcus aureus* is a leading cause of infection in hospitals and in the community. The emergence of antibiotic-resistant strains of *S. aureus* such as methicillin-resistant *Staphylococcus aureus* (MRSA), which are more difficult to treat with standard types of antibiotics, is a current problem in clinical medicine and necessitates the development of new approaches to antibacterial prophylaxis and therapy (Kennedy et al., (2010), J. Infect. Dis. 202:1050-1058).

SUMMARY OF THE INVENTION

The invention provides fully human monoclonal antibodies (mAbs) and antigen-binding fragments thereof that bind specifically to *Staphylococcus aureus* Hemolysin A. Such antibodies may be useful to neutralize the activity of Hemolysin A. The antibodies may act to prevent, halt the progression, or to lessen the severity of a *S. aureus* infections, or reduce the number, the duration, or the severity of infection recurrence, or ameliorate at least one symptom associated with infections. In some cases, the antibodies may be used to prevent or treat a condition or indication associated with *S. aureus* infection such as dermonecrosis, skin and soft-tissue infections (including abscesses), surgical site infections, prosthetic joint infections, bacteremia, septicemia, septic arthritis, meningitis, osteomyelitis, endocarditis, pneumonia, toxic shock syndrome, mastitis, and furunculosis and carbunculosis (boils). Such antibodies may be used alone or in conjunction with a second agent useful for treating *S. aureus* infections. In certain embodiments, the antibodies specific for Hemolysin A may be given therapeutically in conjunction with a second agent to lessen the severity of the *S. aureus* infection, or to reduce the number, the duration, or the severity of infection recurrence, or ameliorate at least one symptom associated with the *S. aureus* infection. In some cases, the combination therapy can be used to treat a condition or indication associated with *S. aureus* infection such as dermonecrosis, skin and soft-tissue infections (including abscesses), surgical site infections, prosthetic joint infections, bacteremia, septicemia, septic arthritis, meningitis, osteomyelitis, endocarditis, pneumonia, toxic shock syndrome, mastitis, and furunculosis and carbunculosis (boils). In certain embodiments, the antibodies may be used prophylactically as stand-alone therapy to protect patients who are at risk for developing a *S. aureus* infection. For example, certain patient populations may be at risk for developing a *S. aureus* infection, including elderly patients, patients who have weakened immune systems, or patients who are at a greater risk of nosocomial infection such as post-operative patients. Any of these patient populations may benefit from treatment with the antibodies of the invention, when given alone or in conjunction with a second agent.

The antibodies of the present invention may be used to treat *Staphylococcus aureus* infection in a patient. The antibodies can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., (2000), J. Immunol. 164: 1925-1933) or increase mAb half-life (Zalevsky et al., (2010), Nature Biotechnology 28:157-159). The present invention includes any antibody or antigen-binding fragment thereof which comprises any of the $V_H$ regions specified herein linked to a heavy chain constant region (e.g., human constant region) such as gamma (e.g., gamma-1, gamma-2, gamma-3 or gamma-4), delta, alpha, mu or epsilon and/or any $V_L$ region specified herein linked to a light chain constant region (e.g., human constant region) such as lambda or kappa.

Accordingly, in a first aspect, the invention provides an isolated fully human monoclonal antibody or antigen-binding fragment thereof that specifically binds to Hemolysin A.

In some cases, the human monoclonal antibody binds to wild type Hemolysin A (SEQ ID NO: 291) or a modified Hemolysin A (SEQ ID NO: 295).

In one embodiment, the isolated human antibody or antigen-binding fragment thereof binds to Hemolysin A with a $K_D$ equal to or less than $10^{-7}$ M as measured by surface plasmon resonance.

In some embodiments, the isolated antibody or antigen-binding fragment thereof exhibits one or more properties selected from the group consisting of: (a) binds to wild type Hemolysin A at 37° C. with a binding dissociation equilibrium constant ($K_D$) of less than about 80 nM as measured by surface plasmon resonance; (b) binds to wild type Hemolysin A at 37° C. with a dissociative half-life (t½) of greater than about 0.5 minutes as measured by surface plasmon resonance; (c) binds to wild type Hemolysin A at 25° C. with a $K_D$ of less than about 30 nM as measured by surface plasmon resonance; (d) binds to wild type Hemolysin A at 25° C. with a t½ of greater than about 1.5 minutes as measured by surface plasmon resonance; (e) binds to a modified hemolysin A at 37° C. with a binding dissociation equilibrium constant ($K_D$) of less than about 20 nM as measured by surface plasmon resonance; (f) binds to a modified Hemolysin A at 37° C. with a dissociative half-life (t½) of greater than about 0.5 minutes as measured by surface plasmon resonance; (g) binds to a modified Hemolysin A at 25° C. with a $K_D$ of less than about 10 nM as measured by surface plasmon resonance; and (11) binds to a modified hemolysin A at 25° C. with a t½ of greater than about 1.5 minutes as measured by surface plasmon resonance.

In some cases, the isolated human antibody or antigen-binding fragment thereof which binds to Hemolysin A comprises three heavy chain complementarity determining regions (CDRs) (HCDR1, HCDR2 and HCDR3) contained within any one of the heavy chain variable region (HCVR) sequences selected from the group consisting of SEQ ID NOs: 2, 22, 42, 62, 82, 102, 122, 142, 162, 182, 202, 222, 242, 262, and 282; and/or three light chain CDRs (LCDR1, LCDR2 and LCDR3) contained within any one of the light chain variable region (LCVR) sequences selected from the group consisting of SEQ ID NOs: 10, 30, 50, 70, 90, 110, 130, 150, 170, 190, 210, 230, 250, and 270. Methods and techniques for identifying CDRs within HCVR and LCVR amino acid sequences are well known in the art and can be used to identify CDRs within the specified heavy chain variable region(s) (HCVR) and/or light chain variable region(s) (LCVR) amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., (1997), *J. Mol. Biol.* 273:927-948; and Martin et al., (1989), *Proc. Natl. Acad. Sci. USA* 86:9268-9272. Public databases are also available for identifying CDR sequences within an antibody.

In some embodiments, the isolated human antibody or antigen-binding fragment thereof, which binds to Hemolysin A, comprises a HCVR having an amino acid sequence selected from the group consisting of SEQ ID NOs: 2, 22, 42, 62, 82, 102, 122, 142, 162, 182, 202, 222, 242, 262, and 282.

In some embodiments, the isolated human antibody or antigen-binding fragment thereof, which binds to Hemolysin A, comprises a LCVR having an amino acid sequence selected from the group consisting of SEQ ID NOs: 10, 30, 50, 70, 90, 110, 130, 150, 170, 190, 210, 230, 250, and 270.

In some cases, the isolated human antibody or antigen-binding fragment thereof, which binds to Hemolysin A, comprises (a) a HCVR having an amino acid sequence selected from the group consisting of SEQ ID NOs: 2, 22, 42, 62, 82, 102, 122, 142, 162, 182, 202, 222, 242, 262, and 282; and (b) a LCVR having an amino acid sequence selected from the group consisting of SEQ ID NO: 10, 30, 50, 70, 90, 110, 130, 150, 170, 190, 210, 230, 250, and 270.

In one embodiment, the isolated human antibody or antigen-binding fragment thereof, which binds to Hemolysin A, comprises:
(a) a HCDR1 domain having an amino acid sequence selected from the group consisting of SEQ ID NOs: 4, 24, 44, 64, 84, 104, 124, 144, 164, 184, 204, 224, 244, 264, and 284;
(b) a HCDR2 domain having an amino acid sequence selected from the group consisting of SEQ ID NOs: 6, 26, 46, 66, 86, 106, 126, 146, 166, 186, 206, 226, 246, 266, and 286;
(c) a HCDR3 domain having an amino acid sequence selected from the group consisting of SEQ ID NOs: 8, 28, 48, 68, 88, 108, 128, 148, 168, 188, 208, 228, 248, 268, and 288;
(d) a LCDR1 domain having an amino acid sequence selected from the group consisting of SEQ ID NOs: 12, 32, 52, 72, 92, 112, 132, 152, 172, 192, 212, 232, 252, and 272;
(e) a LCDR2 domain having an amino acid sequence selected from the group consisting of SEQ ID NOs: 14, 34, 54, 74, 94, 114, 134, 154, 174, 194, 214, 234, 254, and 274; and
(f) a LCDR3 domain having an amino acid sequence selected from the group consisting of SEQ ID NOs: 16, 36, 56, 76, 96, 116, 136, 156, 176, 196, 216, 236, 256, and 276.

In various embodiments, the invention provides a fully human monoclonal antibody or antigen-binding fragment thereof that binds to Hemolysin A, wherein the antibody or fragment thereof exhibits one or more of the following characteristics: (i) comprises a HCVR having an amino acid sequence selected from the group consisting of SEQ ID NO: 2, 22, 42, 62, 82, 102, 122, 142, 162, 182, 202, 222, 242, 262, and 282, or a substantially similar sequence thereof having at least 90%, at least 95%, at least 98% or at least 99% sequence identity; (ii) comprises a LCVR having an amino acid sequence selected from the group consisting of SEQ ID NO: 10, 30, 50, 70, 90, 110, 130, 150, 170, 190, 210, 230, 250, and 270, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 28, 48, 68, 88, 108, 128, 148, 168, 188, 208, 228, 248, 268, and 288, 536, 552, 568, and 584, or a substantially similar sequence thereof having at least 90%, at least 95%, at least 98% or at least 99% sequence identity; and a LCDR3 domain having an amino acid sequence selected from the group consisting of SEQ ID NO: 16, 36, 56, 76, 96, 116, 136, 156, 176, 196, 216, 236, 256, and 276, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 24, 44, 64, 84, 104, 124, 144, 164, 184, 204, 224, 244, 264, and 284, or a substantially similar sequence thereof having at least 90%, at least 95%, at least 98% or at least 99% sequence identity; a HCDR2 domain having an amino acid sequence selected from the group consisting of SEQ ID NO: 6, 26, 46, 66, 86, 106, 126, 146, 166, 186, 206, 226, 246, 266, and 286, or a substantially similar sequence thereof having at least 90%, at least 95%, at least 98% or at least 99% sequence identity; a LCDR1 domain having an amino acid sequence selected from the group consisting of SEQ ID NO: 12, 32, 52, 72, 92, 112, 132, 152, 172, 192, 212, 232, 252, and 272, or a substantially similar sequence thereof having at least 90%, at least 95%, at least 98% or at least 99% sequence identity; and a LCDR2 domain having an amino acid sequence selected from the group consisting of SEQ ID NO: 14, 34, 54, 74, 94, 114, 134, 154, 174, 194, 214, 234, 254, and 274, or a substantially similar sequence thereof having at least 90%, at least 95%, at least 98% or at least 99% sequence identity; and/or (v) binds to Hemolysin A with a $K_D$ equal to or less than $10^{-7}$ M as measured by surface plasmon resonance.

In another aspect, the invention provides an isolated antibody or antigen-binding fragment thereof that competes for binding to Hemolysin A with a reference antibody or antigen-binding fragment comprising the complementarity determining regions (CDRs) of a heavy chain variable region (HCVR) comprising the amino acid sequence selected from the group consisting of SEQ ID NOs: 2, 22, 42, 62, 82, 102, 122, 142, 162, 182, 202, 222, 242, 262, and 282; and the CDRs of a light chain variable region (LCVR) comprising the amino acid sequence selected from the group consisting of SEQ ID NOs: 10, 30, 50, 70, 90, 110, 130, 150, 170, 190, 210, 230, 250, and 270.

In another aspect, the invention provides an isolated antibody or antigen-binding fragment thereof that binds the same epitope on Hemolysin A as a reference antibody or antigen-binding fragment comprising the CDRs of a heavy chain variable region (HCVR) comprising the amino acid sequence selected from the group consisting of SEQ ID NOs: 2, 22, 42, 62, 82, 102, 122, 142, 162, 182, 202, 222, 242, 262, and 282; and the CDRs of a light chain variable region (LCVR) comprising the amino acid sequence selected from the group consisting of SEQ ID NOs: 10, 30, 50, 70, 90, 110, 130, 150, 170, 190, 210, 230, 250, and 270.

In some embodiments, the invention provides an isolated human antibody or antigen-binding fragment thereof that binds Hemolysin A, wherein the antibody or fragment thereof comprises a HCVR/LCVR amino acid sequence pair selected from the group consisting of SEQ ID NOs: 2/10, 22/30, 42/50, 62/70, 82/90, 102/110, 122/130, 142/150, 162/170, 182/190, 202/210, 222/230, 242/250, 262/270, and 282/270.

In another aspect, the invention provides nucleic acid molecules encoding anti-Hemolysin A antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In some embodiments, the invention provides an antibody or fragment thereof comprising a HCVR encoded by a nucleic acid sequence selected from the group consisting of SEQ ID NO: 1, 21, 41, 61, 81, 101, 121, 141, 161, 181, 201, 221, 241, 261, and 281, or a substantially identical sequence having at least 90%, at least 95%, at least 98%, or at least 99% homology thereof.

In some embodiments, the antibody or fragment thereof further comprises a LCVR encoded by a nucleic acid sequence selected from the group consisting of SEQ ID NO: 9, 29, 49, 69, 89, 109, 129, 149, 169, 189, 209, 229, 249, and 269, or a substantially identical sequence having at least 90%, at least 95%, at least 98%, or at least 99% homology thereof.

In some cases, the invention provides an antibody or antigen-binding fragment of an antibody comprising a HCDR3 domain encoded by a nucleotide sequence selected from the group consisting of SEQ ID NO: 7, 27, 47, 67, 87, 107, 127, 147, 167, 187, 207, 227, 247, 267, and 287, or a substantially similar sequence thereof having at least 90%, at least 95%, at least 98% or at least 99% sequence identity; and a LCDR3 domain encoded by a nucleotide sequence selected from the group consisting of SEQ ID NO: 15, 35, 55, 75, 95, 115, 135, 155, 175, 195, 215, 235, 255, and 275, or a substantially similar sequence thereof having at least 90%, at least 95%, at least 98% or at least 99% sequence identity.

In some embodiments, the invention provides an antibody or fragment thereof further comprising a HCDR1 domain encoded by a nucleotide sequence selected from the group consisting of SEQ ID NO: 3, 23, 43, 63, 83, 103, 123, 143, 163, 183, 203, 223, 243, 263, and 283, 563, and 579, or a substantially similar sequence thereof having at least 90%, at least 95%, at least 98% or at least 99% sequence identity; a HCDR2 domain encoded by a nucleotide sequence selected from the group consisting of SEQ ID NO: 5, 25, 45, 65, 85, 105, 125, 145, 165, 185, 205, 225, 245, 265, and 285, or a substantially similar sequence thereof having at least 90%, at least 95%, at least 98% or at least 99% sequence identity; a LCDR1 domain encoded by a nucleotide sequence selected from the group consisting of SEQ ID NO: 11, 31, 51, 71, 91, 111, 131, 151, 171, 191, 211, 231, 251, and 271, or a substantially similar sequence thereof having at least 90%, at least 95%, at least 98% or at least 99% sequence identity; and a LCDR2 domain encoded by a nucleotide sequence selected from the group consisting of SEQ ID NO: 13, 33, 53, 73, 93, 113, 133, 153, 173, 193, 213, 233, 253, and 273, or a substantially similar sequence thereof having at least 90%, at least 95%, at least 98% or at least 99% sequence identity.

In some embodiments, the antibody or antigen-binding fragment thereof that binds to Hemolysin A, as described herein, may be linked to a detectable label such as a radionuclide label or an MRI-detectable label.

In another aspect, the invention provides a pharmaceutical composition comprising an isolated fully human monoclonal antibody or antigen-binding fragment thereof that binds to Hemolysin A, as described above or herein, and a pharmaceutically acceptable carrier or diluent.

In some embodiments, the pharmaceutical composition comprises a fully human monoclonal antibody that binds to Hemolysin A having any one or more of the characteristics described above or herein. In one embodiment, the antibody binds to Hemolysin A with a $K_D$ equal to or less than $10^{-7}$ M. In various embodiments, the composition comprises an antibody that binds to Hemolysin A and has a HCVR/LCVR amino acid sequence pair selected from the group consisting of SEQ ID NOs: 2/10, 22/30, 42/50, 62/70, 82/90, 102/110, 122/130, 142/150, 162/170, 182/190, 202/210, 222/230, 242/250, 262/270, and 282/270. The present invention also provides an isolated human antibody or antigen-binding fragment, wherein the antibody or antigen-binding fragment comprises (i) a light chain immunoglobulin comprising the amino acid sequence set forth in SEQ ID NO: 20, and a heavy chain immunoglobulin comprising the amino acid sequence set forth in SEQ ID NO: 18; (ii) a light chain immunoglobulin comprising the amino acid sequence set forth in SEQ ID NO: 40, and a heavy chain immunoglobulin comprising the amino acid sequence set forth in SEQ ID NO: 38; (iii) a light chain immunoglobulin comprising the amino acid sequence set forth in SEQ ID NO: 60, and a heavy chain immunoglobulin comprising the amino acid sequence set forth in SEQ ID NO: 58; (iv) a light chain immunoglobulin comprising the amino acid sequence set forth in SEQ ID NO: 80, and a heavy chain immunoglobulin comprising the amino acid sequence set forth in SEQ ID NO: 78; (v) a light chain immunoglobulin comprising the amino acid sequence set forth in SEQ ID NO: 100, and a heavy chain immunoglobulin comprising the amino acid sequence set forth in SEQ ID NO: 98; (vi) a light chain immunoglobulin comprising the amino acid sequence set forth in SEQ ID NO: 120, and a heavy chain immunoglobulin comprising the amino acid sequence set forth in SEQ ID NO: 118; (vii) a light chain immunoglobulin comprising the amino acid sequence set forth in SEQ ID NO: 140, and a heavy chain immunoglobulin comprising the amino acid sequence set forth in SEQ ID NO: 138; (viii) a light chain immunoglobulin comprising the amino acid sequence set forth in SEQ ID NO: 160, and a heavy chain immunoglobulin comprising the amino acid sequence set forth in SEQ ID NO: 158; (ix) a light chain immunoglobulin comprising the amino acid sequence set forth in SEQ ID NO: 180, and a heavy chain immunoglobulin comprising the amino acid sequence set forth in SEQ ID NO: 178; (x) a light chain immunoglobulin comprising the amino acid sequence set forth in SEQ ID NO: 200, and a heavy chain immunoglobulin comprising the amino acid sequence set forth in SEQ ID NO: 198; (xi) a light chain immunoglobulin comprising the amino acid sequence set forth in SEQ ID NO: 220, and a heavy chain immunoglobulin comprising the amino acid sequence set forth in SEQ ID NO: 218; (xii) a light chain immunoglobulin comprising the amino acid sequence set forth in SEQ ID NO: 240, and a heavy chain immunoglobulin comprising the amino acid sequence set forth in SEQ ID NO: 238; (xiii) a light chain immunoglobulin comprising the amino acid sequence set forth in SEQ ID NO: 260, and a heavy chain immunoglobulin comprising the amino acid sequence set forth in SEQ ID NO: 258; (xiv) a light chain immunoglobulin comprising the amino acid sequence set forth in SEQ ID NO: 280, and a heavy chain immunoglobulin comprising the amino acid sequence set forth in SEQ ID NO: 278; or (xv) a light chain immunoglobulin comprising the amino acid sequence set forth in SEQ ID NO: 280, and a heavy chain immunoglobulin comprising the amino acid sequence set forth in SEQ ID NO: 290.

In some cases, the invention features a composition, which is a combination of an antibody or antigen-binding fragment of an antibody of the invention, and a second therapeutic agent. The second therapeutic agent may be a small molecule drug, a protein/polypeptide, an antibody, a nucleic acid molecule, such as an anti-sense oligonucleotide, or a siRNA. The second therapeutic agent may be synthetic or naturally derived. The second therapeutic agent may be any agent that is advantageously combined with the antibody or fragment thereof of the invention.

In certain embodiments, the second therapeutic agent may be an agent that helps to counteract or reduce any possible side effect(s) associated with the antibody or antigen-binding fragment of an antibody of the invention, if such side effect(s) should occur.

It will also be appreciated that the antibodies and pharmaceutically acceptable compositions of the present invention can be employed in combination therapies, that is, the antibodies and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an antibody may be administered concurrently with another agent used to treat the same disorder), or they may achieve different effects (e.g., control of any adverse effects). As used herein, additional therapeutic agents that are normally administered to treat or prevent a particular disease, or condition, are appropriate for the disease, or condition, being treated. When multiple therapeutics are co-administered, dosages may be adjusted accordingly, as is recognized in the pertinent art.

In another aspect, the invention provides a method for preventing, treating or managing primary infections caused by *Staphylococcus aureus*, and reducing, eliminating or preventing relapse from *S. aureus* infections. In some cases, the invention includes a method for preventing and/or treating a disease or disorder associated with *S. aureus* infection, such as dermonecrosis, skin and soft-tissue infections (including abscesses), surgical site infections, prosthetic joint infections, bacteremia, septicemia, septic arthritis, meningitis, osteomyelitis, endocarditis, pneumonia, toxic shock syndrome, mastitis, and furunculosis and carbunculosis (boils). In certain embodiments, the invention provides a method for treating a patient suffering from *S. aureus* infection, or for treating at least one symptom or complication associated with *S. aureus* infection, or halting the progression of *S. aureus* infection, the method comprising administering to the patient an effective amount of an antibody or an antigen-binding fragment thereof that binds to Hemolysin A; or a pharmaceutical composition comprising an effective amount of an antibody or an antigen-binding fragment thereof that binds to Hemolysin A, such that the *Staphylococcus aureus* infection-associated condition or disease is either prevented, or lessened in severity and/or duration, or at least one symptom or complication associated with the condition or disease is prevented, or ameliorated, or that the frequency and/or duration of, or the severity of *S. aureus* infection is reduced. In various embodiments of the methods discussed above, the *S. aureus* bacteria may be resistant to one or more types of antibiotic treatments. In one embodiment, the bacteria are methicillin-resistant *S. aureus* (MRSA).

In some embodiments of the method, the pharmaceutical composition comprising the antibodies of the invention is administered to the patient in combination with a second therapeutic agent.

In embodiments of the invention, the antibody or antigen-binding fragment thereof or the pharmaceutical composition comprising the antibody is administered subcutaneously, intravenously, intradermally, orally or intramuscularly.

In related embodiments, the invention includes the use of an isolated anti-Hemolysin A antibody or antigen binding portion of an antibody of the invention in the manufacture of a medicament for the prevention or treatment of a disease or disorder related to or caused by *S. aureus* infection or the presence of Hemolysin A toxin. The invention also includes use of an isolated anti-Hemolysin A antibody or antigen binding portion thereof for preventing or treating a disease or disorder related to or caused by *S. aureus* infection or the presence of Hemolysin A toxin. In various embodiments, these diseases or disorders include dermonecrosis, skin and soft-tissue infections (including abscesses), surgical site infections, prosthetic joint infections, bacteremia, septicemia, septic arthritis, meningitis, osteomyelitis, endocarditis, pneumonia, toxic shock syndrome, mastitis, and furunculosis and carbunculosis (boils). In one embodiment, the invention includes the use of an isolated anti-Hemolysin A antibody or antigen-binding fragment thereof in the manufacture of a medicament for the treatment of a *S. aureus* infection. In some cases, the invention includes the use of an anti-Hemolysin A antibody or antigen-binding fragment thereof as discussed above or herein for treating a patient suffering from or at risk of developing a *Staphylococcus aureus* infection. In some embodiments, the invention includes the use of an anti-Hemolysin A antibody or antigen-binding fragment thereof as discussed above or herein for treating a patient suffering from dermonecrosis, skin and soft-tissue infections (including abscesses), surgical site infections, prosthetic joint infections, bacteremia, septicemia, septic arthritis, meningitis, osteomyelitis, endocarditis, pneumonia, toxic shock syndrome, mastitis, and furunculosis and carbunculosis (boils).

Other embodiments will become apparent from a review of the ensuing detailed description.

BRIEF DESCRIPTION OF THE DRAWINGS

FIG. 2a shows binding to LukF; FIG. 2b shows binding to LukD; and FIG. 2c shows binding to HlgB.

FIGS. 3a, 3b and 3c show binding of anti-Hemolysin A antibody H1H15381P to components of *S. aureus* bicomponent toxins: FIG. 3a shows binding to LukF, LukS, and LukE; FIG. 3b shows binding to HlgA and HlgC; and FIG. 3c shows binding to delta toxin.

FIGS. 4a and 4b: FIG. 4a shows blocking of toxin-induced ADAM10 activity by anti-Hemolysin A antibody H1H15377P, H1H15381P or H1H15399P and FIG. 4b shows prevention of Hemolysin A binding to rabbit red blood cell membranes by anti-Hemolysin A antibody H1H15377 or H1H15399.

FIGS. 5a, 5b and 5c show size of dermonecrotic lesions in mice infected with *S.aureus* CA-127 and treated with various antibodies (H1H15377P, H1H15381P, H1H15399P, LTM14, LC10 or control antibody) at 5, 0.5 or 0.125 mg/kg.

FIGS. 6a, 6b and 6c show size of dermonecrotic lesions in mice infected with *S.aureus* Newman and treated with various antibodies (H1H15377P, H1H15381P, H1H15399P, LTM14, LC10 or control antibody) at 5, 0.5 or 0.125 mg/kg.

DETAILED DESCRIPTION

Figure 1:
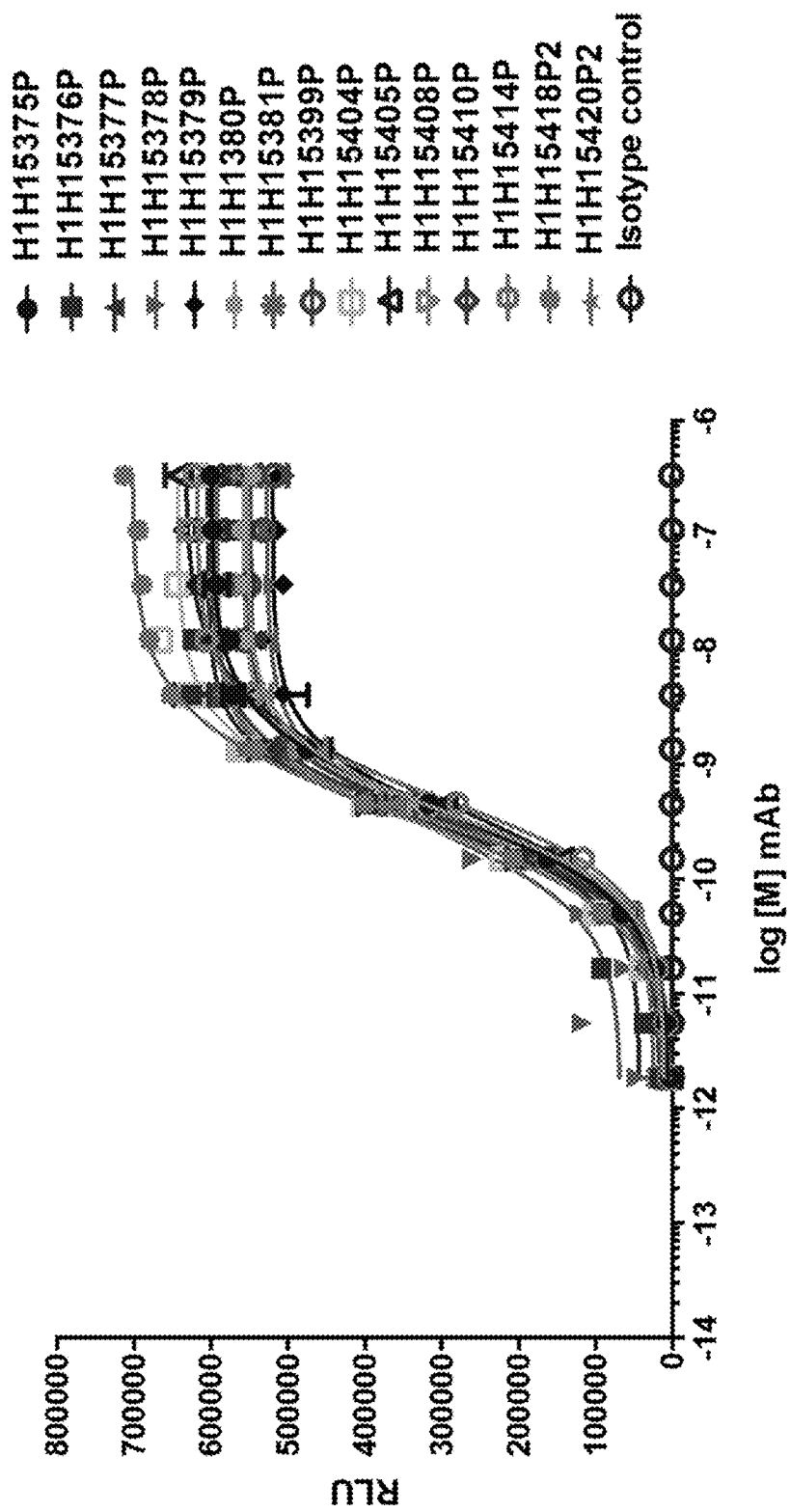
FIG. 1 shows binding of anti-Hemolysin A antibodies to *S. aureus* Hemolysin A.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The terms "Hemolysin A" and "Hemolysin A toxin" refer, interchangeably, to a 33 kDa monomeric protein secreted by *S. aureus* that oligomerizes into a heptameric structure in the membrane of host cells to form a pore leading to cell lysis, inflammation, and tissue damage. The amino acid sequence of wild type Hemolysin A is shown in SEQ ID NO: 291. The amino acid sequence of a modified Hemolysin A (H35L mutant) is shown in SEQ ID NO: 295. Unless otherwise noted, reference to Hemolysin A refers to the wild type form. Hla-H35L is Hemolysin A in which the histidine at position 35 has been changed to a leucine. This allows for the toxin to assemble on the host cell membrane up to the pre-pore formation step but a fully functional pore is not formed. This renders Hemolysin A non-toxigenic.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (FASEB J. 1995, 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-Hemolysin A monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments that comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-Hemolysin A monoclonal antibodies comprising variants of any of the HCVR, LCVR, and/or CDR amino acid sequences disclosed herein having one or more conservative substitutions. For example, the present invention includes anti-hemolysin A antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies that bind specifically to Hemolysin A have been identified by surface plasmon resonance, e.g., BIACORE™. Moreover, multi-specific antibodies that bind to one domain in Hemolysin A and one or more additional antigens or a bi-specific that binds to two different regions of Hemolysin A are nonetheless considered antibodies that "specifically bind", as used herein.

The term "high affinity" antibody refers to those mAbs having a binding affinity to Hemolysin A, expressed as $K_D$, of at least $10^{-7}$ M; preferably $10^{-8}$ M; more preferably $10^{-9}$M, even more preferably $10^{-10}$ M, even more preferably $10^{-11}$ M, as measured by surface plasmon resonance, e.g., BIACORE™ or solution-affinity ELISA.

By the term "slow off rate", "Koff" or "kd" is meant to describe an antibody that dissociates from Hemolysin A with a rate constant of $1\times10^{-3}$ $s^{-1}$ or less, preferably $1\times10^{-4}$ $s^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to Hemolysin A.

In specific embodiments, antibody or antibody fragments of the invention may be conjugated to a therapeutic moiety ("immunoconjugate"), such as an antibiotic, a second anti-Hemolysin A antibody, or an antibody to a cytokine such as IL-1, IL-6, or TGF-β, or any other therapeutic moiety useful for treating a disease or condition including *Staphylococcus aureus* infection, skin and soft-tissue infections (including abscesses), surgical site infections, prosthetic joint infections, bacteremia, septicemia, septic arthritis, meningitis, osteomyelitis, endocarditis, pneumonia, toxic shock syndrome, mastitis, and furunculosis and carbunculosis (boils).

An "isolated antibody", as used herein, is intended to refer to an antibody that is substantially free of other antibodies (Abs) having different antigenic specificities (e.g., an isolated antibody that specifically binds Hemolysin A, or a fragment thereof, is substantially free of Abs that specifically bind antigens other than Hemolysin A).

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol.

215: 403-410 and (1997) Nucleic Acids Res. 25: 3389-3402, each of which is herein incorporated by reference.

In specific embodiments, the antibody or antibody fragment for use in the method of the invention may be monospecific, bi-specific, or multi-specific. Multi-specific antibodies may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise an Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 mAbs; N44S, K52N, and V82I (IMGT; N384S, K392N, and V422I by EU) in the case of IgG2 mAbs; and Q15R, N44S, K52N, V57M, R69K, E79Q, and V82I (by IMGT; Q355R, N384S, K392N, V397M, R409K, E419Q, and V422I by EU) in the case of IgG4 mAbs. Variations on the bi-specific antibody format described above are contemplated within the scope of the present invention.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

General Description

*Staphylococcus aureus* Hemolysin A toxin is a 33 kDa secreted monomeric protein that oligomerizes into a heptameric structure in the membrane of host cells to form a pore leading to cell lysis, inflammation, and tissue damage. Hemolysin A has been shown to play a role in pneumonia, dermonecrosis, endocarditis, and sepsis.

The antibodies described herein demonstrate specific binding to Hemolysin A and in some embodiments, may be useful for treating patients suffering from *S. aureus* infections, or preventing such infections. The use of such antibodies may be an effective means of treating patients suffering from *S. aureus* infection, or may be used to lessen the severity of the symptoms of a *S. aureus* infection. They may be used alone or as adjunct therapy with other therapeutic moieties or modalities known in the art for treating *Staphylococcus aureus* infection, such as, but not limited to, an antibiotic, a non-steroidal anti-inflammatory drug (NSIAD) (or other palliative therapy), or a corticosteroid such as prednisone. They may be used in conjunction with additional antibodies specific for antigens other than Hemolysin A, or may combined with other types of treatments.

In some embodiments, the antibodies described herein may be useful in preventing, treating or managing a disease or condition of *Staphylococcus aureus* infection including, but not limited to, dermonecrosis, skin and soft-tissue infections (including abscesses), surgical site infections, prosthetic joint infections, bacteremia, septicemia, septic arthritis, meningitis, osteomyelitis, endocarditis, pneumonia, toxic shock syndrome, mastitis, and furunculosis and carbunculosis (boils).

In certain embodiments, the antibodies of the invention are obtained from mice immunized with a primary immunogen, such as a native, full length Hemolysin A (SEQ ID NO: 291) or with a modified form of Hemolysin A (SEQ ID NO: 295) or Hemolysin A fragments, followed by immunization with a secondary immunogen, or with an immunogenically active fragment of Hemolysin A.

The immunogen may be an immunogenic fragment of Hemolysin A or DNA encoding the fragment thereof. The immunogen may be Hemolysin A coupled to a histidine tag and/or to a fragment of Fc region of an antibody.

The amino acid sequence of full length Hemolysin A is shown as SEQ ID NO: 291. The full length amino acid sequence of modified Hemolysin A is shown as SEQ ID NO: 295.

In certain embodiments, antibodies that bind specifically to Hemolysin A may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of Hemolysin A-specific antibodies. In certain embodiments, any one or more of the above-noted regions of Hemolysin A, or fragments thereof may be used for preparing monospecific, bispecific, or multispecific antibodies.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to Hemolysin A. An antibody fragment may include a Fab fragment, a F(ab')$_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single-domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; $V_H$-$C_H$2; $V_H$-$C_H$3; (iv) $V_H$-$C_H$1-$C_H$2; (V) $V_H$-$C_H$1-$C_H$2-$C_H$3; (Vi) $V_H$-$C_H$2-$C_H$3; (Vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

The present invention includes anti-hemolysin A antibodies and antigen-binding fragments having immunoglobulin chains that include the amino acid sequences set forth herein as well as variants having cellular and/or in vitro post-translational modifications. For example, the present invention includes antibodies and antigen-binding fragments thereof that specifically bind to hemolysin A comprising heavy and/or light chain amino acid sequences set forth herein (e.g., CDR-H1, CDR-H2, CDR-H3, CDR-L1, CDR-L2 and/or CDR-L3) as well as antibodies and fragments wherein one or more amino acid residues is glycosylated, one or more Asn residues is deamidated, one or more residues (e.g., Met, Trp and/or His) is oxidized, the N-terminal Gln is pyroglutamate (pyroE) and/or the C-terminal Lysine is missing.

The present invention includes recombinant methods for making anti-hemolysin A antibodies or antigen-binding fragments thereof of the present invention, or an immunoglobulin chain thereof, comprising (i) introducing one or more polynucleotides encoding a light and/or a heavy immunoglobulin chain of said antibody or antigen-binding fragment (e.g., a heavy chain or $V_H$ thereof or immunoglobulin comprising the HCDR1, HCDR2 and HCDR3 thereof and/or a light chain or $V_L$ thereof or immunoglobulin comprising the LCDR1, LCDR2 and LCDR3 thereof), for example, wherein the polynucleotide is in a vector and/or is operably linked to a promoter; (ii) culturing the host cell (e.g., Chinese hamster ovary (CHO) cell or *Pichia* cell or *Pichia pastoris* cell) under condition favorable to expression of the polynucleotide(s) and, (iii) optionally, isolating the antibody or fragment or chain from the host cell and/or medium in which the host cell is grown. When making an antibody or antigen-binding fragment comprising more than one immunoglobulin chain, e.g., an antibody that comprises two heavy immunoglobulin chains and two light immunoglobulin chains, co-expression of the chains in a single host cell leads to association of the chains, e.g., in the cell or on the cell surface or outside the cell if such chains are secreted, so as to form the antibody or antigen-binding fragment molecule. The methods include those wherein only a heavy immunoglobulin chain or only a light immunoglobulin chain (e.g., any of those discussed herein including mature fragments and/or variable domains thereof) is expressed. Such chains are useful, for example, as intermediates in the expression of an antibody or antigen-binding fragment that includes such a chain. The present invention includes the products of such expression methods (e.g., antibodies, antigen-binding fragments, $V_H$s, or $V_L$s).

Preparation of Human Antibodies

Methods for generating human antibodies in transgenic mice are known in the art. Any such known methods can be used in the context of the present invention to make human antibodies that specifically bind to Hemolysin A.

Using VELOCIMMUNE™ technology (see, for example, U.S. Pat. No. 6,596,541, Regeneron Pharmaceuticals, VELOCIMMUNE®) or any other known method for generating monoclonal antibodies, high affinity chimeric antibodies to Hemolysin A are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high-affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-12}$ through about $10^{-7}$ M, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Bioequivalents

The anti-Hemolysin A antibodies and antibody fragments of the present invention encompass proteins having amino acid sequences that vary from those of the described antibodies, but that retain the ability to bind Hemolysin A. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-Hemolysin A Antibodies Comprising Fc Variants

According to certain embodiments of the present invention, anti-Hemolysin A antibodies are provided comprising an Fc domain comprising one or more mutations which enhance or diminish antibody binding to the FcRn receptor, e.g., at acidic pH as compared to neutral pH. For example, the present invention includes anti-Hemolysin A antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification(s) (e.g., 308F and/or 308P). In yet another embodiment, the modification comprises a 265A (e.g., D265A) and/or a 297A (e.g., N297A) modification.

For example, the present invention includes anti-Hemolysin A antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E);

428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations, and other mutations within the antibody variable domains disclosed herein, are contemplated within the scope of the present invention.

The present invention also includes anti-Hemolysin A antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 ora human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013, the disclosure of which is hereby incorporated by reference in its entirety).

The present invention also includes anti-Hemolysin A antibodies comprising a modified heavy chain constant ($C_H$) regions in which one or more substitutions (e.g., mutations) that interfere with the binding of Protein A have been introduced. For example, in some embodiments, anti-Hemolysin A antibodies of the invention have an IgG1 constant regions in which His435 has been mutated to Arg. With this point mutation in the heavy chain constant regions, an anti-Hemolysin A antibody of the invention would not bind to Protein A. In other embodiments of the invention, anti-Hemolysin A antibodies contain a dipeptide mutation, H435R/Y436F (EU numbering; H95R/Y96F by IMGT) in the heavy chain constant regions in order to abrogate Protein A binding. (See, e.g., U.S. Pat. No. 8,586,713, filed Jun. 25, 2010, the disclosure of which is hereby incorporated by reference in its entirety.)

Biological Characteristics of the Antibodies

In general, the antibodies of the present invention may function by binding to Hemolysin A. In some embodiments, the antibodies of the present invention may bind to another antigen (cross-reactive antibodies).

In certain embodiments, antibodies of the present invention may bind to other bacterial toxins or toxin subunits, in addition to Hemolysin A. Additional toxins or toxin subunits of *S. aureus* to which antibodies of the present invention may bind include bicomponent pore-forming leukotoxins (e.g., leuckocidins or gamma hemolysin) and/or S or F subunits of these toxins (e.g., LukF, LukD, and/or HlgB). In certain embodiments, antibodies of the present invention only show significant binding to Hemolysin A. In certain embodiments, antibodies of the present invention only bind detectably to Hemolysin A.

In certain embodiments, the antibodies of the present invention may be bi-specific antibodies. The bi-specific antibodies of the invention may bind one epitope in one domain and may also bind one epitope in a second domain of Hemolysin A. In certain embodiments, the bi-specific antibodies of the invention may bind two different epitopes in the same domain.

In one embodiment, the invention provides a fully human monoclonal antibody or antigen-binding fragment thereof that binds to Hemolysin A, wherein the antibody or fragment thereof exhibits one or more of the following characteristics: (i) comprises a HCVR having an amino acid sequence selected from the group consisting of SEQ ID NO: 2, 22, 42, 62, 82, 102, 122, 142, 162, 182, 202, 222, 242, 262, and 282, or a substantially similar sequence thereof having at least 90%, at least 95%, at least 98% or at least 99% sequence identity; (ii) comprises a LCVR having an amino acid sequence selected from the group consisting of SEQ ID NO: 10, 30, 50, 70, 90, 110, 130, 150, 170, 190, 210, 230, 250, and 270, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 28, 48, 68, 88, 108, 128, 148, 168, 188, 208, 228, 248, 268, and 288, or a substantially similar sequence thereof having at least 90%, at least 95%, at least 98% or at least 99% sequence identity; and a LCDR3 domain having an amino acid sequence selected from the group consisting of SEQ ID NO: 16, 36, 56, 76, 96, 116, 136, 156, 176, 196, 216, 236, 256, and 276, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 24, 44, 64, 84, 104, 124, 144, 164, 184, 204, 224, 244, 264, and 284, or a substantially similar sequence thereof having at least 90%, at least 95%, at least 98% or at least 99% sequence identity; a HCDR2 domain having an amino acid sequence selected from the group consisting of SEQ ID NO: 6, 26, 46, 66, 86, 106, 126, 146, 166, 186, 206, 226, 246, 266, and 286, or a substantially similar sequence thereof having at least 90%, at least 95%, at least 98% or at least 99% sequence identity; a LCDR1 domain having an amino acid sequence selected from the group consisting of SEQ ID NO: 12, 32, 52, 72, 92, 112, 132, 152, 172, 192, 212, 232, 252, and 272, or a substantially similar sequence thereof having at least 90%, at least 95%, at least 98% or at least 99% sequence identity; and a LCDR2 domain having an amino acid sequence selected from the group consisting of SEQ ID NO: 14, 34, 54, 74, 94, 114, 134, 154, 174, 194, 214, 234, 254, and 274, or a substantially similar sequence thereof having at least 90%, at least 95%, at least 98% or at least 99% sequence identity; and (v) binds to Hemolysin A with a Ko equal to or less than $10^{-7}$.

Certain anti-Hemolysin A antibodies of the present invention are able to bind to and neutralize the activity of Hemolysin A, as determined by in vitro or in vivo assays. The ability of the antibodies of the invention to bind to and neutralize the activity of Hemolysin A may be measured using any standard method known to those skilled in the art, including binding assays, or activity assays, as described herein.

Non-limiting, exemplary in vitro assays for measuring binding activity are illustrated in Example 3 and 4, herein.

In Example 6, the binding affinities and kinetic constants of human anti-Hemolysin A antibodies were determined by surface plasmon resonance and the measurements were conducted on a T200 Biacore instrument. Example 5 describes neutralization of the *S. aureus* Hemolysin A using Hemolysin A-specific antibodies.

The present invention also includes anti-Hemolysin A antibodies and antigen binding fragments thereof which bind to at least one biologically active fragment of any of the following proteins, or peptides: SEQ ID NO: 291 (full length wild type Hemolysin A), or SEQ ID NO: 295 (modified form of Hemolysin A). Any of the Hemolysin A peptides described herein, or fragments thereof, may be used to generate anti-Hemolysin A antibodies.

The peptides may be modified to include addition or substitution of certain residues for tagging or for purposes of conjugation to carrier molecules, such as, KLH. For example, a cysteine may be added at either the N-terminal or C-terminal end of a peptide, or a linker sequence may be added to prepare the peptide for conjugation to, for example, KLH for immunization.

The antibodies specific for Hemolysin A may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antibodies may be used in diagnostic assays including imaging assays.

Epitope Mapping and Related Technologies

The present invention includes anti-Hemolysin A antibodies which interact with one or more amino acids found within one or more regions of Hemolysin A. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned regions of the Hemolysin A molecule (e.g. a linear epitope in a domain). Alternatively, the epitope may consist of a plurality of non-contiguous amino acids (or amino acid sequences) located within either or both of the aforementioned regions of the Hemolysin A molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in *Antibodies*, Harlow and Lane (Cold Spring Harbor Press, Cold Spring Harbor, N.Y.). Other methods include alanine scanning mutational analysis, peptide blot analysis (Reineke (2004) Methods Mol Biol 248:443-63), peptide cleavage analysis, crystallographic studies and NMR analysis. In addition, methods such as epitope excision, epitope extraction and chemical modification of antigens can be employed (Tomer (2000) Protein Science 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the peptides containing the deuterium-labeled residues that contain specific amino acids with which the antibody interacts. See, e.g., Ehring (1999) *Analytical Biochemistry* 267(2):252-259; Engen and Smith (2001) *Anal. Chem.* 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the anti-Hemolysin A antibodies or antigen-binding fragments thereof bind an epitope within any one or more of the regions exemplified in wild type Hemolysin A, as exemplified in SEQ ID NO: 291, or modified Hemolysin A, as exemplified in SEQ ID NO: 295, or to a fragment thereof.

The present invention includes human anti-Hemolysin A antibodies that bind to the same epitope, or a portion of the epitope, as any of the specific exemplary antibodies described herein, or an antibody having the CDR sequences of any of the exemplary antibodies described herein. Likewise, the present invention also includes anti-Hemolysin A antibodies that compete for binding to Hemolysin A or a Hemolysin A fragment with any of the specific exemplary antibodies described herein, or an antibody having the CDR sequences of any of the exemplary antibodies described herein.

One can easily determine whether an antibody binds to the same epitope as, or competes for binding with, a reference anti-Hemolysin A antibody by using routine methods known in the art. For example, to determine if a test antibody binds to the same epitope as a reference anti-Hemolysin A antibody of the invention, the reference antibody is allowed to bind to a Hemolysin A protein or peptide under saturating conditions. Next, the ability of a test antibody to bind to the Hemolysin A molecule is assessed. If the test antibody is able to bind to Hemolysin A following saturation binding with the reference anti-Hemolysin A antibody, it can be concluded that the test antibody binds to a different epitope than the reference anti-hemolysin A antibody. On the other hand, if the test antibody is not able to bind to the Hemolysin A protein following saturation binding with the reference anti-Hemolysin A antibody, then the test antibody may bind to the same epitope as the epitope bound by the reference anti-Hemolysin A antibody of the invention.

To determine if an antibody competes for binding with a reference anti-Hemolysin A antibody, the above-described binding methodology is performed in two orientations: In a first orientation, the reference antibody is allowed to bind to a Hemolysin A protein under saturating conditions followed by assessment of binding of the test antibody to the Hemolysin A molecule. In a second orientation, the test antibody is allowed to bind to a Hemolysin A molecule under saturating conditions followed by assessment of binding of the reference antibody to the Hemolysin A molecule. If, in both orientations, only the first (saturating) antibody is capable of binding to the Hemolysin A molecule, then it is concluded that the test antibody and the reference antibody compete for binding to Hemolysin A. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-Hemolysin A monoclonal antibody conjugated to a therapeutic moiety ("immunoconjugate"), such as an agent that is capable of reducing the severity of *Staphylococcus aureus* infection, or to ameliorate at least one symptom associated with *S. aureus* infection, or the severity thereof. As used herein, the term "immunoconjugate" refers to an antibody that is chemically or biologically linked to a radioactive agent, a cytokine, an interferon, a target or reporter moiety, an enzyme, a toxin, or a therapeutic agent. The antibody may be linked to the radioactive agent, cytokine, interferon, target or reporter moiety, enzyme, toxin, or therapeutic agent at any location along the molecule so long as it is able to bind its target. An example of immunoconjugate is an antibody drug conjugate. In some embodiments, the agent may be a second different antibody to Hemolysin A, or to a cytokine such as IL-1, IL-6, or a chemokine such as TGF-β. The type of therapeutic moiety that may be conjugated to the anti-Hemolysin A antibody will take into account the condition to be treated and the desired therapeutic effect to be achieved. Examples of suitable agents for forming immunoconjugates are known in the art; see for example, WO 05/103081. The preparation of immunoconjugates and immunotoxins is generally well known in the art (see, e.g., U.S. Pat. No. 4,340,535). Immunoconjugates are described in detail, for example, in U.S. Pat. Nos. 7,250,492, 7,420,040 and 7,411,046, each of which is incorporated herein in their entirety.

Multi-Specific Antibodies

The antibodies of the present invention may be mono-specific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity. For example, the present invention includes bi-specific antibodies wherein one arm of an immunoglobulin is specific for the N-terminal region of Hemolysin A, or a fragment thereof, and the other arm of the immunoglobulin is specific for the C-terminal region of Hemolysin A, or a second therapeutic target, or is conjugated to a therapeutic moiety. An exemplary bi-specific antibody format that can be used in the context of the present invention involves the use of a first immunoglobulin (Ig) $C_{H3}$ domain and a second Ig $C_{H3}$ domain, wherein the first and second Ig $C_{H3}$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_{H3}$ domain binds Protein A and the second Ig $C_{H3}$ domain contains a mutation that reduces or abolishes Protein A binding such as an H95R modification (by IMGT exon numbering; H435R by EU numbering). The second $C_{H3}$ may further comprise a Y96F modification (by IMGT; Y436F by EU). Further modifications that may be found within the second $C_{H3}$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

The invention provides therapeutic compositions comprising the anti-Hemolysin A antibodies or antigen-binding fragments thereof as discussed herein. The therapeutic compositions in accordance with the invention can be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When the antibody of the present invention is used for preventing or treating dermonecrosis, skin and soft-tissue infections (including abscesses), surgical site infections, prosthetic joint infections, bacteremia, septicemia, septic arthritis, meningitis, osteomyelitis, endocarditis, pneumonia, toxic shock syndrome, mastitis, or furunculosis and carbunculosis (boils) in an adult patient, or for preventing or treating an *S. aureus* infection, it is advantageous to intravenously administer the antibody of the present invention normally at a single dose of about 0.1 to about 100 mg/kg body weight, more preferably about 5 to about 100, about 10 to about 90, or about 20 to about 70 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles for drug delivery have also been described in, for example, U.S. Pat. Nos. 8,277,812, 8,258,256, 8,257,740, 8,246,995, 8,236,330, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms. The present invention includes an injection device (e.g., a pre-filled syringe or pre-filled autoinjector) or a vial (e.g., a glass or plastic vial) comprising an antibody or antigen-binding fragment of the present invention or pharmaceutical composition thereof which includes a pharmaceutically acceptable carrier.

Therapeutic Uses of the Antibodies

In certain embodiments of the invention, the present antibodies are useful for treating a *Staphylococcus aureus* infection, or at least one symptom associated with *S. aureus* infection. In some embodiments, the antibodies may be useful for treating a condition or symptom of dermonecrosis, skin and soft-tissue infections (including abscesses), surgical site infections, prosthetic joint infections, bacteremia, septicemia, septic arthritis, meningitis, osteomyelitis, endocarditis, pneumonia, toxic shock syndrome, mastitis, or furunculosis and carbunculosis (boils). The antibodies of the invention are also contemplated for prophylactic use in patients at risk for developing a *S. aureus* infection. These patients include the elderly, or patients immunocompromised due to illness or treatment with immunosuppressive therapeutics, or patients who are at a greater risk of nosocomial infection such as post-operative patients. In various embodiments of the therapeutic uses discussed above, the *S. aureus* bacteria may be resistant to one or more types of antibiotic treatments. In one embodiment, the bacteria are methicillin-resistant *S. aureus* (MRSA). It is contemplated that the antibodies of the invention may be used alone, or in conjunction with a second agent, or third agent for treating *S. aureus* infection, or for alleviating at least one symptom or complication associated with *S. aureus* infection. The second or third agents may be delivered concurrently with the antibodies of the invention, or they may be administered separately, either before or after the antibodies of the invention. A patient that may receive an antibody or antigen-binding fragment of the invention or a pharmaceutical composition thereof includes, for example, an animal such as a mammal such as a human (e.g., an elderly human, for example, 65 years of age or older), rabbit, mouse, rat, cow, pig, dog, primate, horse or sheep.

In certain embodiments, the present antibodies are useful for reducing the number of *Staphylococcus aureus* bacteria in an individual or a particular tissue or organ of the individual. In some embodiments, the *S. aureus* bacteria may be resistant to one or more types of antibiotic treatments. In one embodiment, the bacteria are methicillin-resistant *S. aureus* (MRSA). In certain embodiments, the present antibodies are useful for reducing the toxic activities of Hemolysin A produced by *Staphylococcus aureus* bacteria in an individual reducing the symptoms produced by the infection, and permitting other pharmaceutical agents and/or the immune system of the patient to control the infection.

In a further embodiment of the invention the present antibodies are used for the preparation of a pharmaceutical composition for treating patients suffering from *Staphylococcus aureus* infection, or a symptom associated with *S. aureus* infection.

Combination Therapies

Combination therapies may include an anti-Hemolysin A antibody of the invention and any additional therapeutic agent(s) that may be advantageously combined with an antibody of the invention, or with a biologically active fragment of an antibody of the invention.

The antibodies may be used in conjunction with other therapies, such as antibiotics NSAIDs, antibody LTM14, antibody LC10, corticosteroids or prednisone.

The additional therapeutically active component(s) may be administered prior to, concurrent with, or after the administration of the anti-Hemolysin A antibody of the present invention. For purposes of the present disclosure, such administration regimens are considered the administration of an anti-Hemolysin A antibody "in combination with" one or more additional therapeutically active component(s).

Diagnostic Uses of the Antibodies

The anti-Hemolysin A antibodies of the present invention may also be used to detect and/or measure Hemolysin A in a sample, e.g., for diagnostic purposes. It is envisioned that any one or more of the antibodies of the invention may be used to detect the presence and severity of *Staphylococcus aureus* infection. Exemplary diagnostic assays for Hemolysin A may comprise, e.g., contacting a sample, obtained from a patient, with an anti-Hemolysin A antibody of the invention, wherein the anti-Hemolysin A antibody is labeled with a detectable label or reporter molecule or used as a capture ligand to selectively isolate Hemolysin A from patient samples. Alternatively, an unlabeled anti-Hemolysin A antibody can be used in diagnostic applications in combination with a secondary antibody which is itself detectably labeled. The detectable label or reporter molecule can be a radioisotope, such as $^3H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure Hemolysin A in a sample include enzyme-linked immunosorbent assay (ELISA), radioimmunoassay (RIA), and fluorescence-activated cell sorting (FACS).

Samples that can be used in Hemolysin A diagnostic assays according to the present invention include any tissue or fluid sample obtainable from a patient, which contains detectable quantities of either Hemolysin A, or fragments thereof, under normal or pathological conditions. Generally, levels of Hemolysin A in a particular sample obtained from a healthy patient (e.g., a patient not afflicted with *Staphylococcus aureus* infection) will be measured to initially establish a baseline, or standard, level of Hemolysin A. This baseline level of Hemolysin A can then be compared against the levels of Hemolysin A measured in samples obtained from individuals suspected of having *S. aureus* infection related condition, or symptoms associated with such condition.

The antibodies specific for Hemolysin A may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In some embodiments, the label may be detectable label such as a radionuclide, a fluorescent dye or a MRI-detectable label. Detectable labels may be linked to the antibodies wherein such antibodies may be used in imaging assays.

EXAMPLES

The following examples are put forth so as to provide those of ordinary skill in the art with a complete disclosure and description of how to make and use the methods and compositions of the invention, and are not intended to limit the scope of what the inventors regard as their invention. Unless indicated otherwise, parts are parts by weight, molecular weight is average molecular weight, temperature is in degrees Centigrade, and pressure is at or near atmospheric.

Example 1. Generation of Human Antibodies to Hemolysin A

Two immunogens were used to immunize mice: full-length wild type Hemolysin A (Hla) without the signal sequence (amino acids 27-391) and full length non-toxic Hemolysin A (Hla-H35L); both were recombinant His-tagged proteins expressed in *E. coli* and purified. In certain embodiments, antibodies that bind specifically to Hemolysin A may be prepared using fragments of the above-noted regions, or peptides that extend beyond the designated regions by about 5 to about 20 amino acid residues from either, or both, the N- or C-terminal ends of the regions described herein. In certain embodiments, any combination of the above-noted regions or fragments thereof may be used in the preparation of Hemolysin A specific antibodies. In certain embodiments, any one or more of the above-noted domains of Hemolysin A, or fragments thereof may be used for preparing monospecific, bispecific, or multispecific antibodies. H1H15375P, H1H15376P, H1H15377P, H1H15378P, H1H15379P, H1H15380P and H1H15418P2 were produced by immunization with the nontoxic Hemolysin A; and H1H15381P, H1H15399P, H1H15404P, H1H15405P, H1H15408P, H1H15410P, H1H15414P, and H1H15420P2 were produced by immunization with wild-type Hemolysin A.

The full length proteins, or fragments thereof, that were used as immunogens, as noted above, were administered directly, with an adjuvant to stimulate the immune response, to a VELOCIMMUNE® mouse comprising DNA encoding human Immunoglobulin heavy and kappa light chain variable regions. The antibody immune response was monitored by a Hemolysin A-specific immunoassay. When a desired immune response was achieved, anti-Hemolysin A antibodies were isolated directly from antigen-positive B cells without fusion to myeloma cells, as described in U.S. 2007/0280945A1, herein specifically incorporated by reference in its entirety. Using this method, several fully human anti-Hemolysin A antibodies (i.e., antibodies possessing human variable domains and human constant domains) were obtained; exemplary antibodies generated in this manner were designated as follows: H1H15375P, H1H15376P, H1H15377P, H1H15378P, H1H15379P, H1H15380P, H1H15381P, H1H15399P, H1H15404P, H1H15405P, H1H15408P, H1H15410P, H1H15414P, H1H15418P2 and H1H15420P2.

The biological properties of the exemplary antibodies generated in accordance with the methods of this Example are described in detail in the Examples set forth below.

Example 2. Heavy and Light Chain Variable Region Amino Acid Sequences

Table 1 sets forth the heavy and light chain variable region amino acid sequence pairs of selected antibodies specific for Hemolysin A and their corresponding antibody identifiers. Antibodies are typically referred to herein according to the following nomenclature: Fc prefix (e.g. "H4H", "H2M"), followed by a numerical identifier (e.g., "5375" as shown in Table 1), followed by a "P" or "N" suffix. Thus, according to this nomenclature, an antibody may be referred to as, e.g., "H1H5375". The H4H, H1M, and H2M prefixes on the antibody designations used herein indicate the particular Fc region of the antibody. For example, an "H2M" antibody has a mouse IgG2 Fc, whereas an "H4H" antibody has a human IgG4 Fc. As will be appreciated by a person of ordinary skill in the art, an H1M or H2M antibody can be converted to an H4H antibody, and vice versa, but in any event, the variable domains (including the CDRs), which are indicated by the numerical identifiers shown in Table 1, will remain the same. Antibodies having the same numerical antibody designation, but differing by a letter suffix of N, B or P refer to antibodies having heavy and light chains with identical CDR sequences but with sequence variations in regions that fall outside of the CDR sequences (i.e., in the framework regions). Thus, N, B and P variants of a particular antibody have identical CDR sequences within their heavy and light chain variable regions but differ from one another within their framework regions.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H15375P | 2 | 4 | 6 | 8 | 10 | 12 | 14 | 16 |
| H1H15376P | 22 | 24 | 26 | 28 | 30 | 32 | 34 | 36 |
| H1H15377P | 42 | 44 | 46 | 48 | 50 | 52 | 54 | 56 |
| H1H15378P | 62 | 64 | 66 | 68 | 70 | 72 | 74 | 76 |
| H1H15379P | 82 | 84 | 86 | 88 | 90 | 92 | 94 | 96 |
| H1H15380P | 102 | 104 | 106 | 108 | 110 | 112 | 114 | 116 |
| H1H15381P | 122 | 124 | 126 | 128 | 130 | 132 | 134 | 136 |
| H1H15399P | 142 | 144 | 146 | 148 | 150 | 152 | 154 | 156 |
| H1H15404P | 162 | 164 | 166 | 168 | 170 | 172 | 174 | 176 |
| H1H15405P | 182 | 184 | 186 | 188 | 190 | 192 | 194 | 196 |
| H1H15408P | 202 | 204 | 206 | 208 | 210 | 212 | 214 | 216 |
| H1H15410P | 222 | 224 | 226 | 228 | 230 | 232 | 234 | 236 |
| H1H15414P | 242 | 244 | 246 | 248 | 250 | 252 | 254 | 256 |
| H1H15418P2 | 262 | 264 | 266 | 268 | 270 | 272 | 274 | 276 |
| H1H15420P2 | 282 | 284 | 286 | 288 | 270 | 272 | 274 | 276 |

Example 3. Binding of Human Monoclonal Antibodies to *S. aureus* Hemolysin A Toxin In order to determine if the antibodies of the invention were able to bind to the Hemolysin A monomer, purified antibodies (H1H15375P, H1H15376P, H1H15377P, H1H15378P, H1H15379P, H1H15380P, H1H15381P, H1H15399P, H1H15404P, H1H15405P, H1H15408P, H1H15410P, H1H15414P, H1H15418P2 and H1H15420P2) were tested by ELISA. MaxiSorp microtiter plates were coated overnight with 10 μg/mL purified *S. aureus* Hemolysin A per well. Titrations of invention antibodies and isotype-matched control antibody (ranging from 50 μM-1 pM with 1:3 serial dilutions) were added to toxin-containing wells and incubated for one hour at 25° C. Wells were washed three times and then incubated with 100 ng/mL anti-human HRP secondary antibody per well for one hour at 25° C. 100 μL of SuperSignal ELISA Pico Chemiluminescent Substrate, (ThermoFisher Scientific) was then added to each well and signal was detected (Victor X3 plate reader, Perkin Elmer). Luminescence values were analyzed by a three-parameter logistic equation over a 12-point response curve (GraphPad Prism).

Sub-nanomolar EC50 binding of the anti-Hemolysin A antibodies were observed for binding to *S. aureus* Hemolysin A toxin. (Table 2 and FIG. 1).

TABLE 2

Binding of anti-Hemolysin A mAbs to *S. aureus* Hemolysin A

| AbPID | EC$_{50}$ [M] for Hemolysin A binding |
|---|---|
| H1H15375P | 3.94E−10 |
| H1H15376P | 3.13E−10 |
| H1H15377P | 2.92E−10 |
| H1H15378P | 2.48E−10 |
| H1H15379P | 3.24E−10 |
| H1H15380P | 3.45E−10 |
| H1H15381P | 2.85E−10 |
| H1H15399P | 3.12E−10 |
| H1H15404P | 3.02E−10 |
| H1H15405P | 5.25E−10 |
| H1H15408P | 3.56E−10 |
| H1H15410P | 3.21E−10 |
| H1H15414P | 5.40E−10 |
| H1H15418P2 | 3.58E−10 |

TABLE 2-continued

Binding of anti-Hemolysin A mAbs to *S. aureus* Hemolysin A

| AbPID | EC$_{50}$ [M] for Hemolysin A binding |
|---|---|
| H1H15420P2 | 3.11E−10 |
| Isotype control | NB |

NB, no binding

Example 4. Binding of Human mAbs to *S. aureus* Hemolysin A to Bicomponent Toxins

*S. aureus* strains can produce additional pore-forming toxins, leukocidins and gamma hemolysin (Hlg), which also require oligomerization to form functional pores. Unlike Hemolysin A, leukocidins and Hlg are bicomponent toxins composed of 2 subunits, the S-subunit and the F-subunit. Currently, five S subunits (LukA, LukE, LukS-PV, HlgA, and HlgC) and four F subunits (LukB, LukD, LukF-PV, and HlgB) have been identified resulting in five functional toxins (LukAB, LukED, PVL, HlgAB, and HlgCB). While low sequence identity is observed between the S- and F-subunits and Hemolysin A (Aman M J and Adhikaari R P, (2014) Toxins. 6:950-972), all components show structural homology with Hemolysin A.

In order to determine if the anti-Hemolysin A antibodies of the invention cross bind to other toxins, purified antibodies (H1H15375P, H1H15376P, H1H15377P, H1H15378P, H1H15379P, H1H15380P, H1H15381P, H1H15399P, H1H15404P, H1H15405P, H1H15408P, H1H15410P, H1H15414P, H1H15418P2 and H1H15420P2) were tested for cross-reactivity to *S. aureus* bicomponent toxins by ELISA. MaxiSorp microtiter plates were coated overnight with 10 μg/mL of individual F-components of *S. aureus* bicomponent toxins per well. Recombinant toxin components were either obtained from IBT BioServices (Gaithersburg, Md.) or generated by GenScript (Piscataway Township, N.J.). Titrations of invention antibodies and an isotype-matched control antibody (ranging from 50 μM-100 pM with 1:3 dilutions) were added to toxin-containing wells and incubated for 1 hour at 25° C. Wells were washed 3 times and then incubated with 100 ng/mL anti-human HRP secondary antibody per well for one hour at 25° C. 100 μL of SuperSignal ELISA Pico Chemiluminescent Substrate, (ThermoFisher Scientific) was added to the wells and signal was detected (Victor X3 plate reader, Perkin Elmer). Luminescence values were analyzed by a three-parameter logistic equation over an 11-point response curve (GraphPad Prism). Isotype-matched irrelevant control antibody and S. aureus delta toxin were included as controls.

Figure 2A:
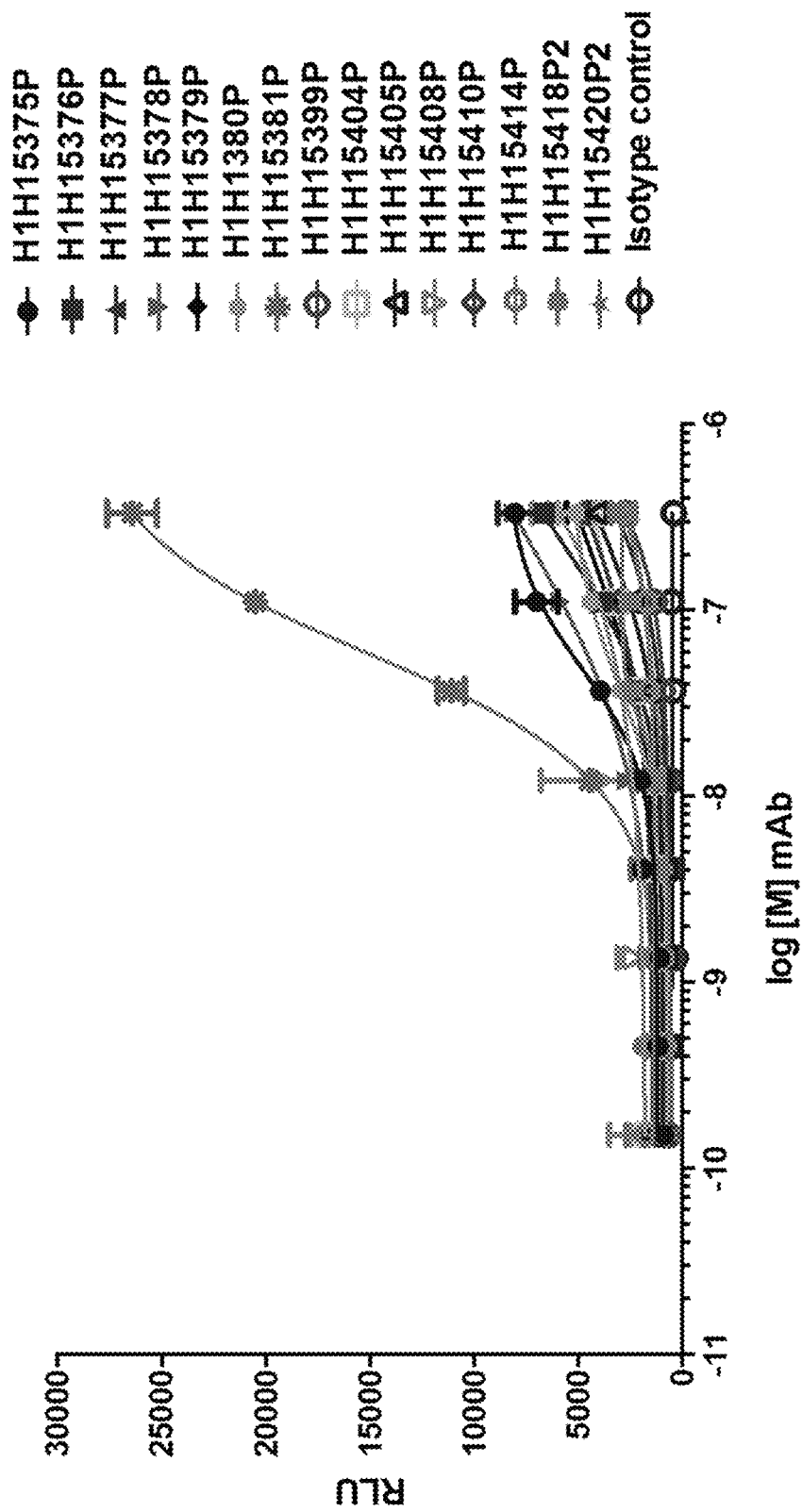
FIGS. 2a, 2b and 2c show binding of anti-Hemolysin A antibodies to F subunits of *S. aureus* bicomponent toxins.
Figure 2B:
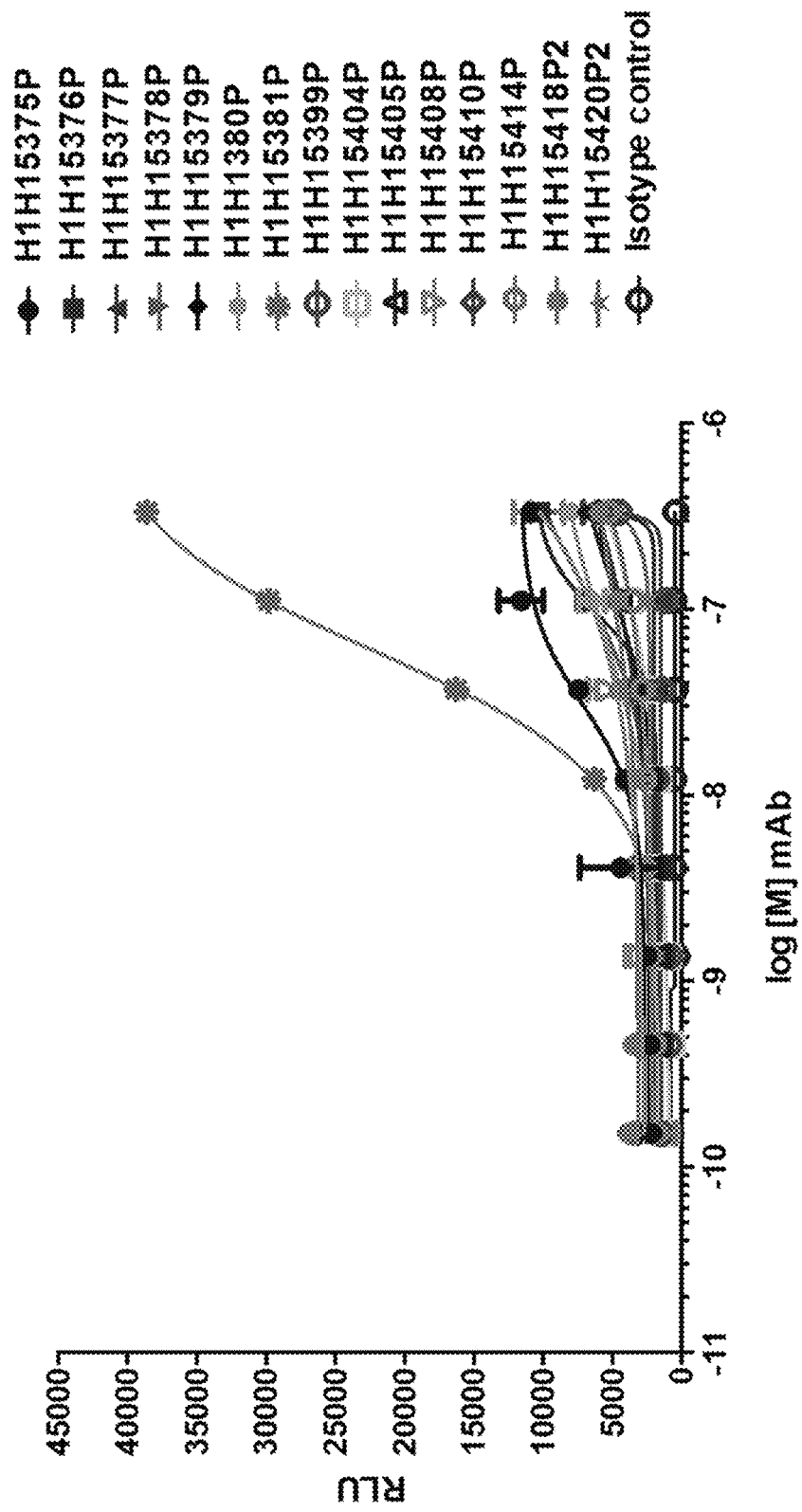
Figure 2C:
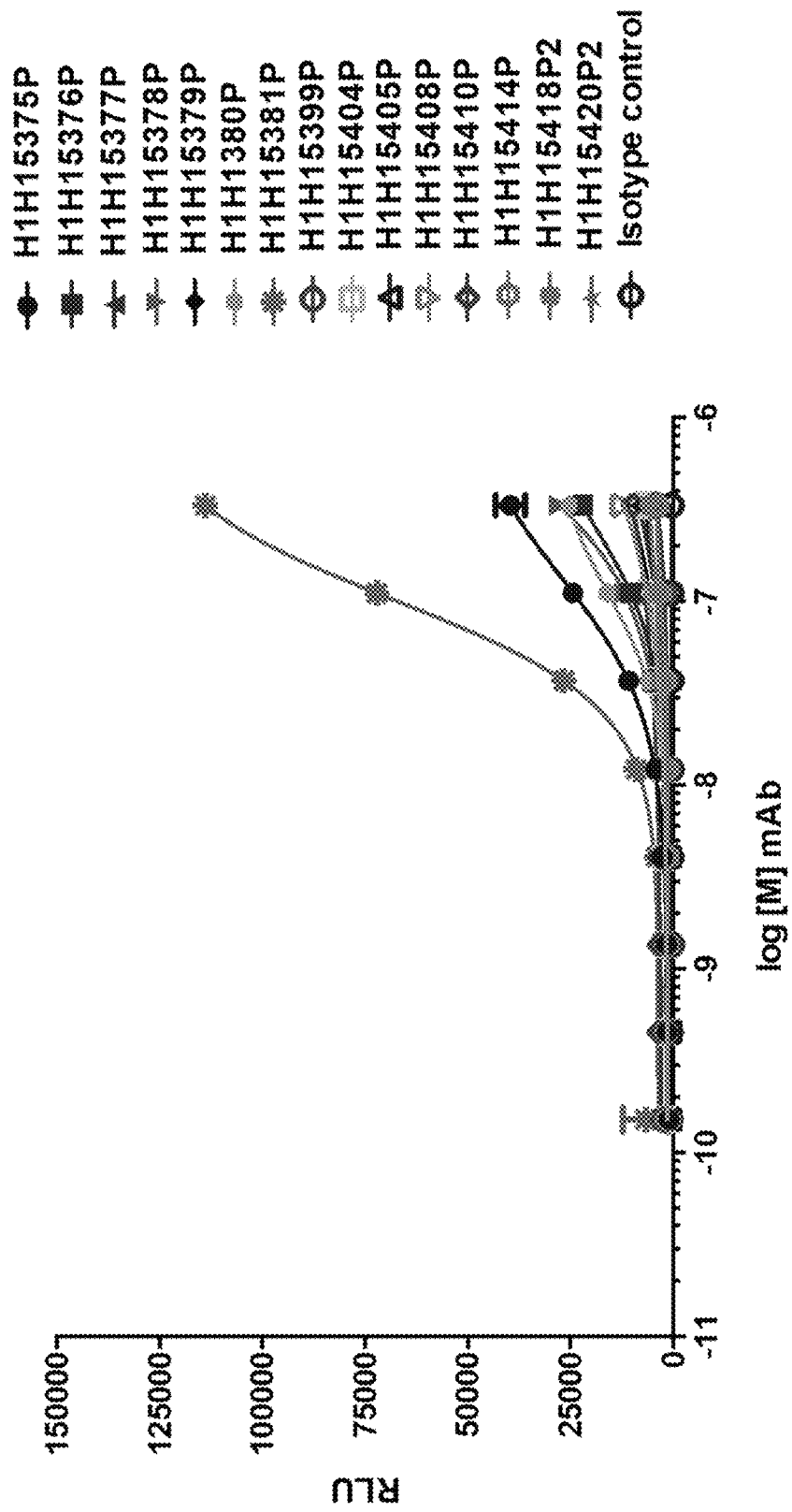
Figure 3B:
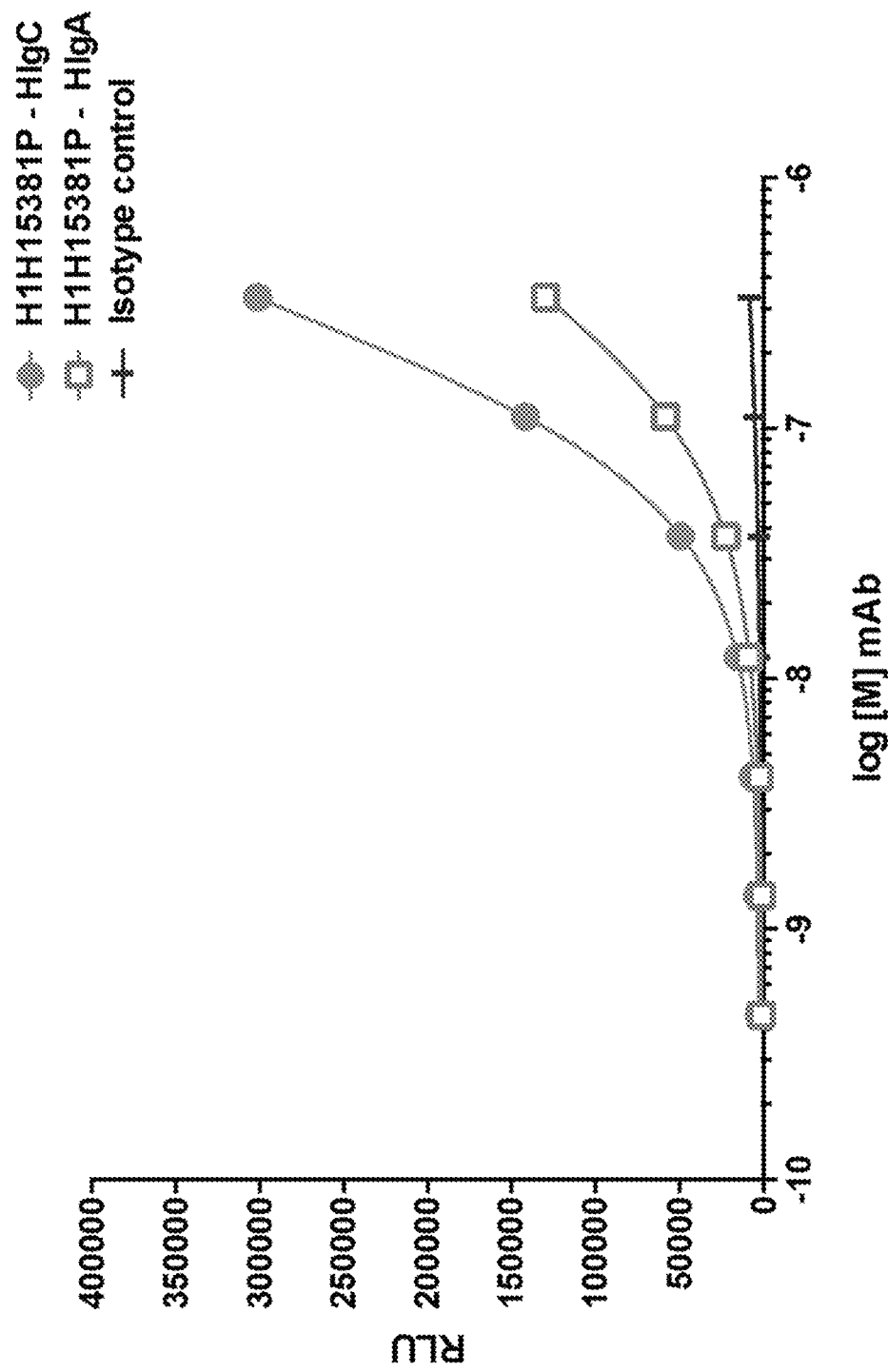

Testing of the 15 antibodies in the invention for cross-reactivity to bicomponent toxins revealed one mAb, H1H15381P, that displayed binding to the F-components LukF, LukD and HlgB, albeit with 2-log or 3-log lower affinity than that seen with Hemolysin A (Table 3 and FIGS. 2a-c). When H1H15381P was tested for cross-reactivity to the S-components LukS, LukE, HlgA and HlgC, binding affinities were significantly lower compared to binding to the F-components (FIGS. 3a-c). H1H15381P binding is specific for Hemolysin A and bicomponent toxins, as it showed no binding to S. aureus delta toxin Isotype-matched control antibody did not demonstrate any binding to the bicomponent toxin components.

TABLE 3

Binding of anti-Hemolysin A mAbs to S. aureus bicomponent toxins (F-component only)

| | $EC_{50}$ [M] for bicomponent toxin binding | | | | S. aureus |
|---|---|---|---|---|---|
| AbPID | LukF (GS) | LukF (IBT) | LukD (GS) | HlgB (GS) | Delta toxin |
| H1H15375P | NB | — | NB | NB | NB |
| H1H15376P | NB | — | NB | NB | NB |
| H1H15377P | NB | — | NB | NB | NB |
| H1H15378P | NB | — | NB | NB | NB |
| H1H15379P | NB | — | NB | NB | NB |
| H1H15380P | NB | — | NB | NB | NB |
| H1H15381P | 6.67E−08 | 1.65E−07 | 5.96E−08 | 1.021E−07 | NB |
| H1H15399P | NB | — | NB | NB | NB |
| H1H15404P | NB | — | NB | NB | NB |
| H1H15405P | NB | — | NB | NB | NB |
| H1H15408P | NB | — | NB | NB | NB |
| H1H15410P | NB | — | NB | NB | NB |
| H1H15414P | NB | — | NB | NB | NB |
| H1H15418P2 | NB | — | NB | NB | NB |
| H1H15420P2 | NB | — | NB | NB | NB |
| Isotype control | NB | — | NB | NB | NB |

GS, GenScript; IBT, IBT BioServices; NB, no binding; —, not tested

Example 5. Neutralization of S. aureus Hemolysin A in a THP-1 Cytotoxicity Assay The ability of purified mAbs to prevent Hemolysin A-mediated lysis was tested using the human monocyte cell line, THP-1. A total of $2.5 \times 10^5$ THP-1 cells in RPMI (supplemented with 1% heat-inactivated FBS, L-glutamine and non-essential amino acids) were seeded into 96-well clear bottom-black tissue culture treated plates and incubated for 1 hour at 37° C. with 5% $CO_2$. Titrations of purified antibodies (H1H15375P, H1H15376P, H1H15377P, H1H15378P, H1H15379P, H1H15380P, H1H15381P, H1H15399P, H1H15404P, H1H15405P, H1H15408P, H1H15410P, H1H15414P, H1H15418P2 and H1H15420P2), or isotype-matched control antibody (ranging from 10-0 μM with 1:3 serial dilutions in media) were incubated with 10 nM purified Hemolysin A in a 96 well plate for 30 minutes at 25° C. on a shaker prior to addition to the plated cells. A titration of purified Hemolysin A (1.5-0 μM with 1:3 dilutions) without antibody was also incubated with cells alone.

The cells with toxin:antibody or toxin alone were then incubated for three hours (37° C., 5% $CO_2$) and cell death was measured using the CytoTox-Glo Assay kit (Promega). Luminescence was detected using a plate reader (Victor X3, Perkin Elmer). All antibodies of the invention displayed similar neutralization activities against Hemolysin A, while isotype-matched antibody did not display any neutralization activity against Hemolysin A. See Table 4.

TABLE 4

Neutralization of S. aureus Hemolysin A in THP-1 cytotoxicity assay

| AbPID | $IC_{50}$ [M] for Hemolysin A neutralization |
|---|---|
| H1H15375P | 3.96E−09 |
| H1H15376P | 7.45E−09 |
| H1H15377P | 1.76E−09 |
| H1H15378P | 10.7E−09 |
| H1H15379P | 6.95E−09 |
| H1H15380P | 7.84E−09 |
| H1H15381P | 4.21E−09 |
| H1H15399P | 1.31E−09 |
| H1H15404P | 6.31E−09 |
| H1H15405P | 5.37E−09 |
| H1H15408P | 6.41E−09 |
| H1H15410P | 5.89E−09 |
| H1H15414P | 1.72E−09 |
| H1H15418P2 | 2.47E−09 |
| H1H15420P2 | 4.14E−09 |

Example 6. Neutralization of S. aureus Hemolysin A in Culture Supernatants Using a Rabbit RBC Hemolysis Assay The Hemolysin A neutralization potency of purified mAbs using S. aureus culture supernatants was assessed using rabbit red blood cells (rRBCs). Culture supernatants were obtained by incubating S. aureus strains (American Type Culture Collection, Manassas, Va.) in TSB for 16 h at 37° C. (with shaking), removing the bacteria by centrifugation and filtering the toxin-containing medium. Titrations of purified antibody H1H15399P or isotype-matched control antibody (ranging from 10-0 μM with 1:2 serial dilutions in 1×PBS) were incubated with sterile filtered S. aureus culture supernatants (that would result in ≥80% cell lysis) in a 96 well plate for 30 minutes at 25° C. on a shaker. After the 30 minute incubation, 100 μl of the culture supernatant:mAb mixtures were added to 96 well round bottom plates containing 100 μl of 4% rRBCs (Colorado Serum Company, Denver, Colo.) in 1×PBS. Following a 1 h incubation at 37° C., plates were centrifuged for 5 min, 100 μl of the supernatant was removed gently to a new microtiter plate, and luminescence was read using a plate reader (SpectraMax i3x, Molecular Devices). All antibodies of the invention displayed similar neutralization activities against Hemolysin A, while isotype-matched antibody did not display any neutralization activity against Hemolysin A. See Table 5.

TABLE 5

Inhibition of native S. aureus Hemolysin A with anti-Hemolysin A mAb H1H15399

| S. aureus strain Designation | PFGE type | $IC_{50}$ [M] for Hemolysin A binding |
|---|---|---|
| GA201 | USA100 | 6.697e−10 |
| MRSA252 | USA200 | No inhibition* |
| CA-127 | USA300 | 2.339e−09 |
| TCH1516 | USA300 | 4.047e−09 |

TABLE 5-continued

Inhibition of native *S. aureus* Hemolysin A with anti-Hemolysin A mAb H1H15399

| S. aureus strain Designation | PFGE type | IC$_{50}$ [M] for Hemolysin A binding |
|---|---|---|
| MW2 | USA400 | No inhibition |
| GA229 | USA500 | 6.725e−10 |
| 00:50 | USA600 | No inhibition |
| 8:03 | USA700 | 7.091e−10 |
| 27-05 | USA800 | 1.274e−09 |
| 94:1013 | USA1000 | 5.434e−09 |
| 7031 | USA1100 | 8.279e−10 |

*MRSA252 contains a stop codon in its Hemolysin A sequence resulting in no Hemolysin A protein secreted.

Example 7. Biacore Binding Affinities and Kinetic Constants of Human Anti-Hemolysin A Monoclonal Antibodies Binding association and dissociation rate constants ($k_a$ and $k_d$, respectively), equilibrium dissociation constants and dissociation half-lives ($K_D$ and $t_{1/2}$, respectively) for wild type and mutant (Hla-H35L) Hemolysin A, binding to purified anti-Hemolysin A antibodies were determined using a real-time surface plasmon resonance biosensor assay on a Biacore T200 instrument. The Biacore sensor surface was derivatized with a monoclonal mouse anti-human Fc antibody (BR-1008-39, GE Healthcare) to capture approximately 150-360 RUs of anti-Hemolysin A monoclonal antibodies, expressed with a human Fc. Different concentrations of Hemolysin A toxins ranging from 100 nM to 1.56 nM were injected over the anti-Hemolysin A monoclonal antibody captured surface at a flow rate of 50 μL/min on Biacore T200. The binding of the Hemolysin A toxins to captured monoclonal antibodies, at 25° C. and 37° C., was monitored for 4 minutes and dissociation from the antibodies was monitored for 10 minutes with HBS-ET (0.01 M HEPES pH 7.4, 0.15 M NaCl, 3 mM EDTA, 0.05% v/v Surfactant P20) as the running buffer.

Kinetic association ($k_a$) and dissociation ($k_d$) rate constants were determined by processing and fitting the data to a 1:1 binding model using Scrubber 2.0c curve fitting software. Binding dissociation equilibrium constants ($K_D$) and dissociative half-lives ($t_{1/2}$) were then calculated from the kinetic rate constants as: $K_D$ (M)=$k_d/k_a$ and $t_{1/2}$ (min)= [In2/(60*$k_d$)].

Binding kinetics parameters for binding of wild type Hemolysin A and mutant Hemolysin A to different anti-Hemolysin A monoclonal antibodies at 25° C. and 37° C. are tabulated in Tables 6-9. As shown in Table 6, at 25° C., all the anti-Hemolysin A antibodies of the invention bound to wild type Hemolysin A with $K_D$ values ranging from 171 pM to 26.2 nM. As shown in Table 7, at 37° C., all the anti-Hemolysin A antibodies of the invention bound to Hemolysin A with $K_D$ values ranging from 260 pM to 76.3 nM. As shown in Table 8, at 25° C., all the anti-Hemolysin A antibodies of the invention bound to mutant Hemolysin A with $K_D$ values ranging from 52.3 pM to 8.89 nM. As shown in Table 9, at 37° C., all the anti-Hemolysin A antibodies of the invention bound to mutant Hemolysin A with $K_D$ values ranging from 74.7 pM to 18.7 nM.

TABLE 6

Binding Kinetics parameters of anti-Hemolysin A monoclonal antibodies binding to wild type Hemolysin A at 25° C.

| | 25° C. | | | |
|---|---|---|---|---|
| Ab PID | $k_a$ (l/mol * s) | $k_d$ (1/s) | $K_D$ [M] | $t_{1/2}$ (min) |
| H1H15420P2 | 7.67E+05 | 1.31E−04 | 1.71E−10 | 88 |
| H1H15414P | 3.62E+05 | 1.15E−04 | 3.18E−10 | 100 |
| H1H15399P | 3.59E+05 | 1.15E−04 | 3.22E−10 | 100 |
| H1H15405P | 7.76E+04 | 6.69E−05 | 8.62E−10 | 173 |
| H1H15418P2 | 1.20E+05 | 1.02E−04 | 8.49E−10 | 113 |
| H1H15377P | 3.09E+05 | 3.15E−04 | 1.02E−09 | 37 |
| H1H15380P | 4.99E+05 | 4.43E−04 | 8.88E−10 | 26 |
| H1H15375P | 6.00E+04 | 1.27E−04 | 2.12E−09 | 91 |
| H1H15381P | 7.81E+05 | 1.50E−03 | 1.92E−09 | 8 |
| H1H15404P | 8.36E+04 | 3.37E−04 | 4.02E−09 | 34 |
| H1H15408P | 1.09E+05 | 8.32E−04 | 7.62E−09 | 14 |
| H1H15410P | 5.62E+04 | 4.62E−04 | 8.22E−09 | 25 |
| H1H15376P | 1.33E+05 | 2.18E−03 | 1.64E−08 | 5 |
| H1H15378P | 3.01E+05 | 7.88E−03 | 2.62E−08 | 1.5 |
| H1H15379P | 2.43E+05 | 6.34E−03 | 2.61E−08 | 1.8 |

TABLE 7

Binding Kinetics parameters of anti-Hemolysin A monoclonal antibodies binding to wild type Hemolysin A at 37° C.

| | 37° C. | | | |
|---|---|---|---|---|
| Ab PID | $k_a$ (l/mol * s) | $k_d$ (1/s) | $K_D$ [M] | $t_{1/2}$ (min) |
| H1H15420P2 | 1.18E+06 | 3.07E−04 | 2.60E−10 | 38 |
| H1H15414P | 5.57E+05 | 3.13E−04 | 5.62E−10 | 37 |
| H1H15399P | 4.90E+05 | 3.22E−04 | 6.57E−10 | 36 |
| H1H15405P | 1.17E+05 | 1.76E−04 | 1.51E−09 | 65 |
| H1H15418P2 | 1.78E+05 | 3.50E−04 | 1.96E−09 | 33 |
| H1H15377P | 4.81E+05 | 1.08E−03 | 2.25E−09 | 11 |
| H1H15380P | 6.49E+05 | 1.48E−03 | 2.28E−09 | 8 |
| H1H15375P | 9.40E+04 | 4.28E−04 | 4.56E−09 | 27 |
| H1H15381P | 9.32E+05 | 6.50E−03 | 6.97E−09 | 1.8 |
| H1H15404P | 1.18E+05 | 2.07E−03 | 1.75E−08 | 6 |
| H1H15408P | 1.48E+05 | 4.05E−03 | 2.73E−08 | 2.9 |
| H1H15410P | 8.68E+04 | 2.51E−03 | 2.89E−08 | 5 |
| H1H15376P | 1.70E+05 | 8.42E−03 | 4.96E−08 | 1.4 |
| H1H15378P | 4.21E+05 | 2.29E−02 | 5.45E−08 | 0.5 |
| H1H15379P | 3.04E+05 | 2.32E−02 | 7.63E−08 | 0.5 |

TABLE 8

Binding kinetics parameters of anti-Hemolysin A monoclonal antibodies binding to mutant Hemolysin A at 25° C.

| | 25° C. | | | |
|---|---|---|---|---|
| Ab PID | $k_a$ (l/mol * s) | $k_d$ (1/s) | $K_D$ [M] | $t_{1/2}$ (min) |
| H1H15420P2 | 2.28E+06 | 1.19E−04 | 5.23E−11 | 97 |
| H1H15414P | NB | NB | NB | NB |
| H1H15399P | 9.98E+05 | 1.00E−04 | 1.00E−10 | 116 |
| H1H15405P | 2.46E+05 | 5.82E−05 | 2.37E−10 | 199 |
| H1H15418P2 | 3.96E+05 | 7.43E−05 | 1.88E−10 | 155 |
| H1H15377P | 1.12E+06 | 4.11E−04 | 3.67E−10 | 28 |
| H1H15380P | 1.39E+06 | 3.87E−04 | 2.79E−10 | 30 |
| H1H15375P | 1.76E+05 | 1.17E−04 | 6.65E−10 | 99 |
| H1H15381P | 2.26E+06 | 1.22E−03 | 5.40E−10 | 9 |
| H1H15404P | 2.68E+05 | 2.94E−04 | 1.10E−09 | 39 |
| H1H15408P | 3.47E+05 | 7.05E−04 | 2.03E−09 | 16 |
| H1H15410P | 1.52E+05 | 3.99E−04 | 2.63E−09 | 29 |
| H1H15376P | 4.22E+05 | 1.45E−03 | 3.43E−09 | 8 |

TABLE 8-continued

Binding kinetics parameters of anti-Hemolysin A monoclonal antibodies binding to mutant Hemolysin A at 25° C.

| Ab PID | 25° C. | | | |
|---|---|---|---|---|
| | $k_a$ (1/mol * s) | $k_d$ (1/s) | $K_D$ [M] | $t_{1/2}$ (min) |
| H1H15378P | 7.66E+05 | 6.81E-03 | 8.89E-09 | 1.7 |
| H1H15379P | 6.81E+05 | 4.43E-03 | 6.51E-09 | 2.6 |

*NB indicates that under the experimental conditions, Hemolysin A toxin did not bind to the captured anti-Hemolysin A monoclonal antibody.

TABLE 9

Binding Kinetics parameters of anti-Hemolysin A monoclonal antibodies binding to mutant Hemolysin A at 37° C.

| Ab PID | 37° C. | | | |
|---|---|---|---|---|
| | $k_a$ (1/mol * s) | $k_d$ (1/s) | $K_D$ [M] | $t_{1/2}$ (min) |
| H1H15420P2 | 3.56E+06 | 2.66E-04 | 7.47E-11 | 43 |
| H1H15414P | NB | NB | NB | NB |
| H1H15399P | 1.42E+06 | 2.78E-04 | 1.96E-10 | 42 |
| H1H15405P | 4.30E+05 | 1.52E-04 | 3.54E-10 | 76 |
| H1H15418P2 | 5.68E+05 | 2.29E-04 | 4.03E-10 | 51 |
| H1H15377P | 1.59E+06 | 1.37E-03 | 8.64E-10 | 8 |
| H1H15380P | 1.88E+06 | 1.31E-03 | 6.95E-10 | 9 |
| H1H15375P | 3.11E+05 | 3.70E-04 | 1.19E-09 | 31 |
| H1H15381P | 2.45E+06 | 4.66E-03 | 1.90E-09 | 2.5 |
| H1H15404P | 3.35E+05 | 1.81E-03 | 5.41E-09 | 6 |
| H1H15408P | 4.38E+05 | 2.93E-03 | 6.68E-09 | 4 |
| H1H15410P | 2.26E+05 | 2.19E-03 | 9.72E-09 | 5 |
| H1H15376P | 4.73E+05 | 4.41E-03 | 9.32E-09 | 2.6 |
| H1H15378P | 9.43E+05 | 1.68E-02 | 1.78E-08 | 0.7 |
| H1H15379P | 6.41E+05 | 1.20E-02 | 1.87E-08 | 1 |

*NB indicates that under the experimental conditions, Hemolysin A toxin did not bind to the captured anti-Hemolysin A monoclonal antibody.

Example 8. Mechanism of Anti-Hemolysin A mAb Blocking Activity

To determine if Hemolysin A mAbs exert their function by blocking the interaction of the toxin with its specific receptor, ADAM10, host cell-associated metalloprotease activity was measured using a fluorogenic peptide substrate assay using A549 cells incubated with Hemolysin A. Titrations of Hemolysin A mAbs (H1H15377P, H1H15381P and H1H15399P) were pre-incubated with 3 nM purified Hemolysin A for 15 min at 37° C. prior to addition to 96 well plates containing $2.5 \times 10^4$ A549 cells in Ham's F-12K (supplemented with 10% heat-inactivated FBS and L-glutamine). After incubation for 60 min at 37° C., 5 μM fluorogenic peptide substrate (Mca-PLAVQ-Dpa-RSSSR-NH2, R&D Systems, Minneapolis, Minn.) was added, incubated for 15 min at 37° C. and fluorescence intensity was read using a plate reader (excitation filter of 320 nm and an emission filter of 405 nm, SpectraMax i3x, Molecular Devices) and expressed as relative fluorescence units. Antibodies of the invention blocked the toxin-induced increase in ADAM10 activity, while isotype-matched antibody did not display any effect on the toxin-induced increased ADAM10 activity (FIG. 4a). This suggested that antibodies of the invention blocked interaction of Hemolysin A to its receptor.

Figure 4B:
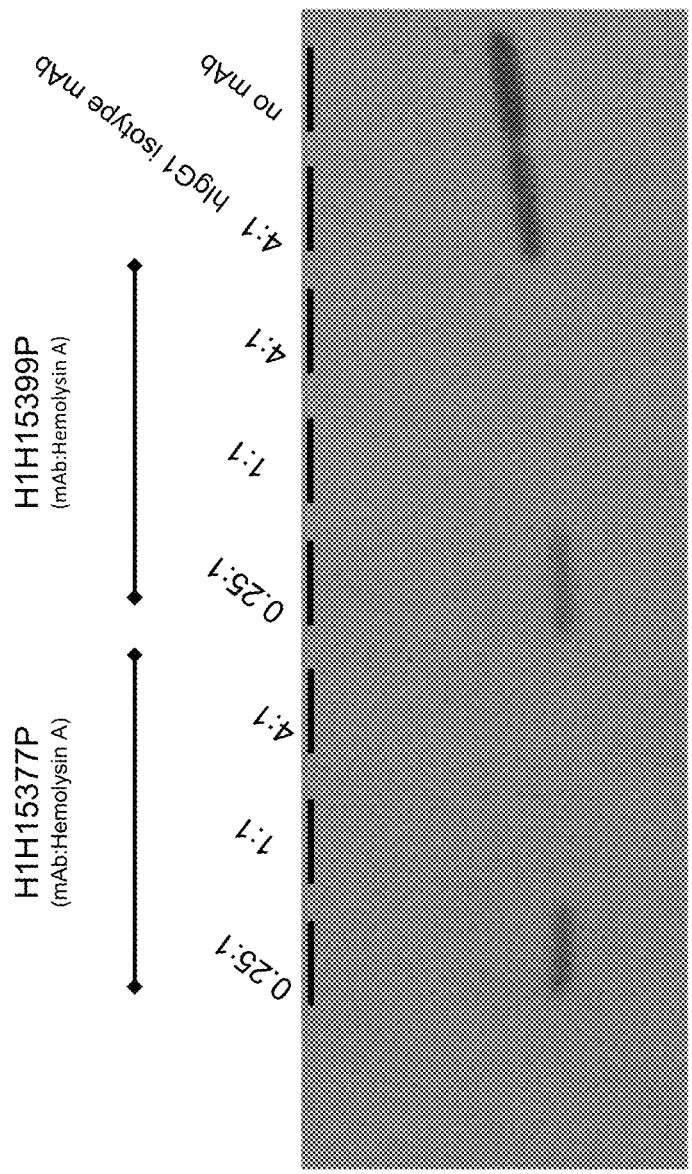

To further demonstrate that the Hemolysin A mAbs prevented binding of the toxin to the host cell membrane, membrane binding experiments were performed in the presence of the Hemolysin A mAbs using rabbit RBCs (rRBCs), and the association of the toxin with the rRBC membrane was detected by Western blot analysis. To avoid lysis of the rRBCs, binding experiments were performed at 4° C. Titrations of Hemolysin A mAbs (H1H15377P and H1H15399P) were pre-incubated with 10 nM Hemolysin A for 15 min at 37° C. prior to addition to washed rRBCs (10% in 250 μl PBS) and incubated for 60 min at 4° C. rRBCs were pelleted, supernatant removed and cells were lysed by three cycles of resuspension in 1 ml of ddH$_2$O, incubation for 10 min at 25° C. and centrifugation at 16,100×g Membranes were solubilized in 10 mM Tris-HCl, pH 7.4, 150 mM NaCl, 1% Triton X-100 and 1% sodium deoxycholate. Solubilized samples were reduced, boiled, and separated on a 4-12% SDS-PAGE gel (Invitrogen, Carlsbad, Calif.) transferred to PVDF membrane (Invitrogen, Carlsbad, Calif.) and Hemolysin A monomer was detected with a pAb (IBT BioServices, Rockville, Md.). Antibodies of the invention prevented binding of Hemolysin A to rRBC membrane while isotype-matched antibody did not display any effect (FIG. 4b).

Example 9. In Vivo Efficacy of Human Anti-Hemolysin A mAbs Administered Prophylactically in a Dermonecrosis Mouse Model In order to determine if anti-Hemolysin A mAbs of the invention were able to decrease or prevent *S. aureus*-induced skin lesions, purified antibodies were tested prophylactically in an in vivo dermonecrosis model using female BALB/c mice (n=3-5) (Bubeck Wardenburg et al., (2008) J. Infect. Dis. 198:1166-1170). Two days prior to infection, fur was removed from the abdominal area by shaving and applying hair removal lotion. One day prior to infection, mice were injected i.p. on the left side of the abdomen with a single dose of either 5 mg/kg or 0.5 mg/kg of each individual antibody: H1H15375P, H1H15376P, H1H15377P, H1H15378P, H1H15379P, H1H15380P, H1H15381P, H1H15399P, H1H15404P, H1H15405P, H1H15408P, H1H15410P, H1H15414P, H1H15418P2, H1H15420P2, or an isotype-matched control antibody. On the day of infection, mice were challenged subcutaneously, on the right side of the abdomen, with 50 μls of S, aureus CA-127 ($\sim$1-2$\times 10^8$ CFU/mouse) that had been grown to log phase (OD$_{600}$≤1) in TSB at 37° C., washed and suspended in PBS. Mouse lesions were measured with a digital caliper on day 2 post-infection.

All antibodies of the invention were efficacious at both tested doses. When administered at 5 mg/kg, all antibodies, showed similar efficacy, reducing dermonecrotic lesions 80-90% when compared to isotype-matched control antibody (Table 10). Similarly, when administered to animals at 0.5 mg/kg, all antibodies of the invention (with the exception of H1H15410P), showed reductions in lesion size when compared to those treated with the isotype-matched antibody (Table 10). Reduction in lesion size, however, ranged from 40-80%, with H1H15410P showing no effect at this dose. Antibodies H1H15380P, H1H15381P, H1H15405P and H1H15414P were the most efficacious when administered at 0.5 mg/kg, with >80% reduction in lesion sizes. Comparison of the 5 mg/kg and 0.5 mg/kg groups showed a dose-dependent effect: mice receiving antibodies at the 5 mg/kg dose had smaller lesions compared to mice receiving the same antibody at the 0.5 mg/kg dose.

TABLE 10

Lesion size comparison for anti-Hemolysin A monoclonal antibodies
in a prophylaxis murine dermonecrosis model, Day 2 post-infection

| | Mice receiving 5 mg/kg mAb and infected with $1.3 \times 10^8$ CFU S. aureus CA-127 | | | | Mice receiving 0.5 mg/kg mAb and infected with $1.5 \times 10^8$ CFU S. aureus CA-127 | | | |
|---|---|---|---|---|---|---|---|---|
| AbPID | Mice (n) | Decrease Relative to Isotype (%) | Mean Lesion Size (mm) | SD | Mice (n) | Decrease Relative to Isotype (%) | Mean Lesion Size (mm) | SD |
| H1H15375P | 5 | 90.7 | 31.6 | 6.3 | 5 | 68.0 | 63.2 | 29.2 |
| H1H15376P | 5 | 89.2 | 37.0 | 7.2 | 5 | 79.9 | 39.8 | 9.4 |
| H1H15377P | 5 | 85.7 | 48.8 | 7.0 | 5 | 57.5 | 84.1 | 70.1 |
| H1H15378P | 5 | 88.4 | 39.5 | 9.9 | 5 | 67.1 | 65.0 | 30.4 |
| H1H15379P | 5 | 88.5 | 39.1 | 13.3 | 5 | 76.9 | 45.6 | 39.9 |
| H1H15380P | 5 | 87.1 | 44.2 | 8.0 | 5 | 82.1 | 35.4 | 23.5 |
| H1H15381P | 5 | 83.9 | 55.1 | 22.2 | 5 | 85.1 | 29.5 | 26.0 |
| H1H15399P | 5 | 89.0 | 37.7 | 13.4 | 5 | 69.9 | 59.6 | 18.3 |
| H1H15404P | 5 | 86.7 | 45.5 | 12.5 | 5 | 46.6 | 105.7 | 40.5 |
| H1H15405P | 5 | 92.1 | 27.0 | 7.1 | 5 | 86.4 | 26.9 | 11.1 |
| H1H15408P | 5 | 90.1 | 33.9 | 10.4 | 5 | 73.1 | 53.3 | 17.2 |
| H1H15410P | 5 | 86.5 | 46.2 | 9.8 | 4 | 0.0 | 216.8 | 98.1 |
| H1H15414P | 5 | 90.2 | 33.5 | 17.5 | 5 | 82.1 | 35.5 | 12.5 |
| H1H15418P2 | 5 | 86.6 | 45.8 | 6.7 | 5 | 48.9 | 101.1 | 63.1 |
| H1H15420P2 | 5 | 85.8 | 48.5 | 7.9 | 5 | 62.2 | 74.7 | 37.5 |
| Isotype control | 3 | 0.0 | 341.6 | 38.6 | 5 | 0.0 | 197.8 | 56.8 |

To further interrogate the ability of the anti-Hemolysin A mAbs to decrease lesion size, the mAbs were administered prophylactically at three different doses and compared to two other anti-Hemolysin A mAbs, LTM14 (See e.g., U.S. Pat. No. 8,715,673—SEQ ID NOs: 1 and 2; or Foletti et al., Mechanism of Action and In Vivo Efficacy of a Human-Derived Antibody against Staphylococcus α-Hemolysin, J. Mol. Biol. 425: 1641-1654 (2013)) and LC10 (see e.g., WO2012/109285-SEQ ID NOs: 57 and 58). Fur was removed from female BALB/c mice as described above two days prior to infection. One day prior to infection, mice (n=5 per group) were injected i.p. on the left side of the abdomen with a single dose of 5 mg/kg, 0.5 mg/kg or 0.125 mg/kg of each individual antibody: H1H15377P, H1H15381P, H1H15399P, LTM14, LC10 or an isotype-matched control antibody. On the day of infection, mice were challenged subcutaneously, on the right side of the abdomen, with 50 μls of S. aureus CA-127 (MRSA strain; $2.5 \times 10^8$ CFU/mouse) or S. aureus Newman (MSSA strain; $2.5 \times 10^8$ CFU/mouse) that had been grown to log phase ($OD_{600} \leq 1$) in TSB at 37° C., washed and suspended in PBS. Mouse lesions were measured with a digital caliper on day 2 post-infection.

Figure 5A:
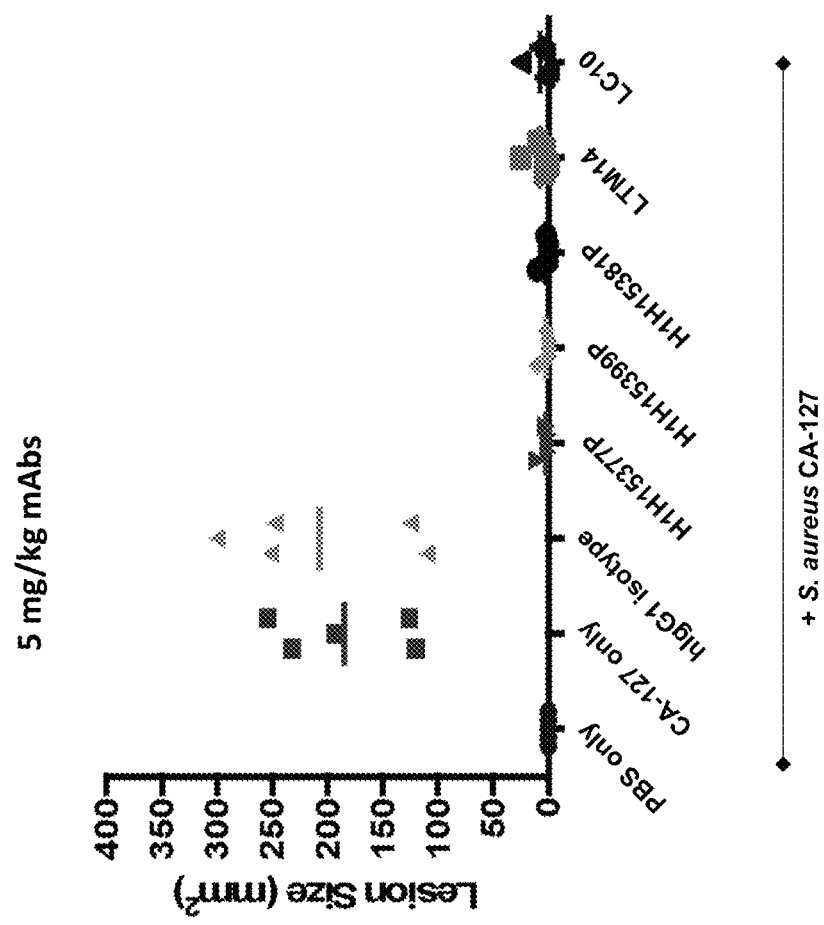
Figure 5B:
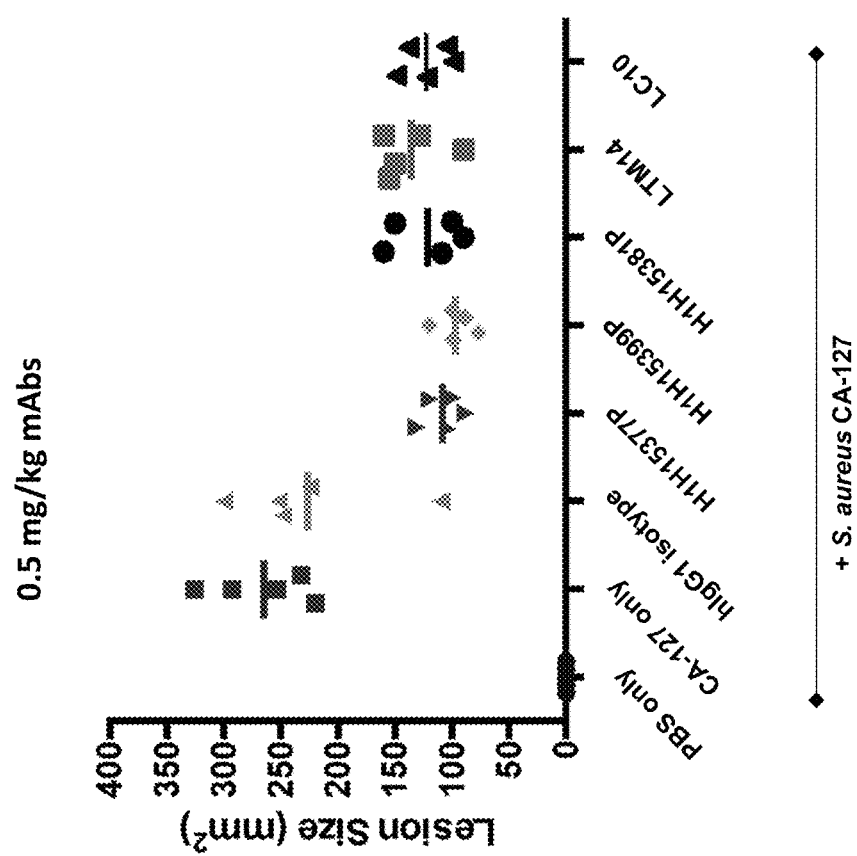

All antibodies of the invention were efficacious at all three tested doses using both MRSA and MSSA S. aureus strains. When administered at 5 mg/kg, all antibodies, including LC10 and LTM14, showed similar efficacy against both S. aureus CA-127 (FIG. 5a) and Newman (FIG. 6a), reducing lesions ≥85% when compared to isotype-matched control antibody. Similarly, when administered to mice at 0.5 mg/kg, all antibodies showed similar reductions of 50-60% in lesion size when compared to those treated with the isotype-matched antibody (FIGS. 5b and 6b). Reductions in lesion size, however, were greater with H1H15377P and H1H15399P compared to H1H15381P, LC10 and LTM14 when administered at 0.125 mg/kg using both S. aureus CA-127 (FIG. 5c) and Newman (FIG. 6c) ranging from 30-40%, compared to those treated with the isotype-matched antibody. For all antibodies, comparison of the 5 mg/kg, 0.5 mg/kg and 0.125 mg/kg groups showed a dose-dependent effect: mice receiving antibodies at the higher concentrations had the smaller lesions (5 mg/kg dose lesions <0.5 mg/kg dose lesions <0.125 mg/kg dose lesions).

Example 10. Bacteria Counts in Skin of Mice Administered Anti-Hemolysin A mAbs Prophylactically Three purified antibodies of the invention, H1H15377P, H1H15381P and H1H15399P, were tested in a dermonecrosis model to determine if there were any observed changes in the bacterial burden in the skin of mice prophylactically treated with the antibodies. The antibodies of the invention were also compared to two other anti-Hemolysin A mAbs, LC10 and LTM14. Two days prior to infection, fur was removed from the abdominal area of female BALB/c mice by shaving and applying hair removal lotion. One day prior to infection, mice were injected i.p. on the left side of the abdomen with a single dose of 5 mg/kg of each individual antibody: H1H15377P, H1H15381P and H1H15399P, LTM14, LC10 or an isotype-matched control antibody. On the day of infection, mice (n=5 per group) were challenged, subcutaneously, on the right side of the abdomen, with 50 μls of S. aureus CA-127 (MRSA strain; $2.5 \times 10^8$ CFU/mouse) or Newman (MSSA strain; $2.9 \times 10^8$ CFU/mouse) that had been grown to log phase ($OD_{600} \leq 1$) in TSB at 37° C., washed and suspended in PBS. The mice were euthanized by anesthesia 2 days post-infection, the lesion area (and surrounding skin) was excised using an 8-mm dermal biopsy punch and homogenized. Serial dilutions of the skin lysates were plated on TSA plates. Plates were incubated overnight (16-18 hours) at 37° C. and bacterial colonies were counted the next day for determination of bacterial burden.

Figure 7A:
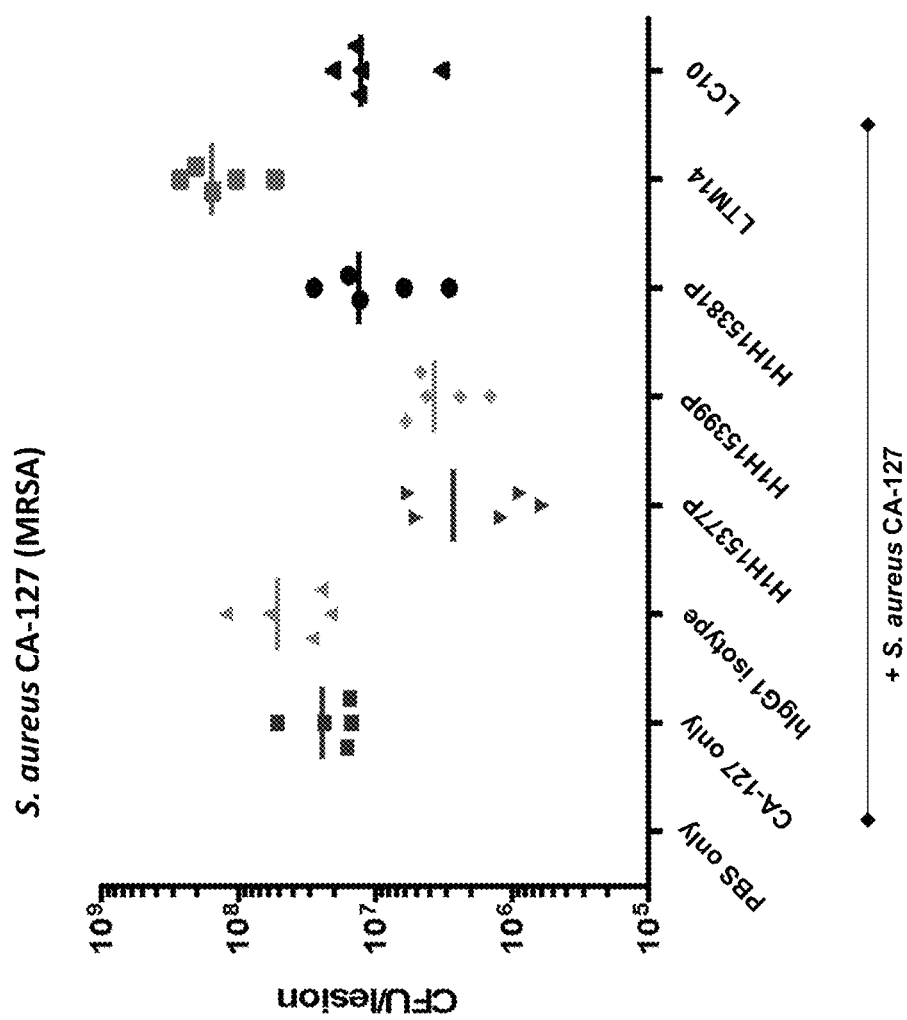
FIGS. 7a and 7b show *S.aureus* CA-127 (MRSA) or *S.aureus* Newman (MSSA) bacteria counts in skin of mice administered various anti-Hemolysin A mAbs (H1H15377P, H1H15381P, H1H15399P, LTM14, LC10 or control antibody).
Figure 7B:
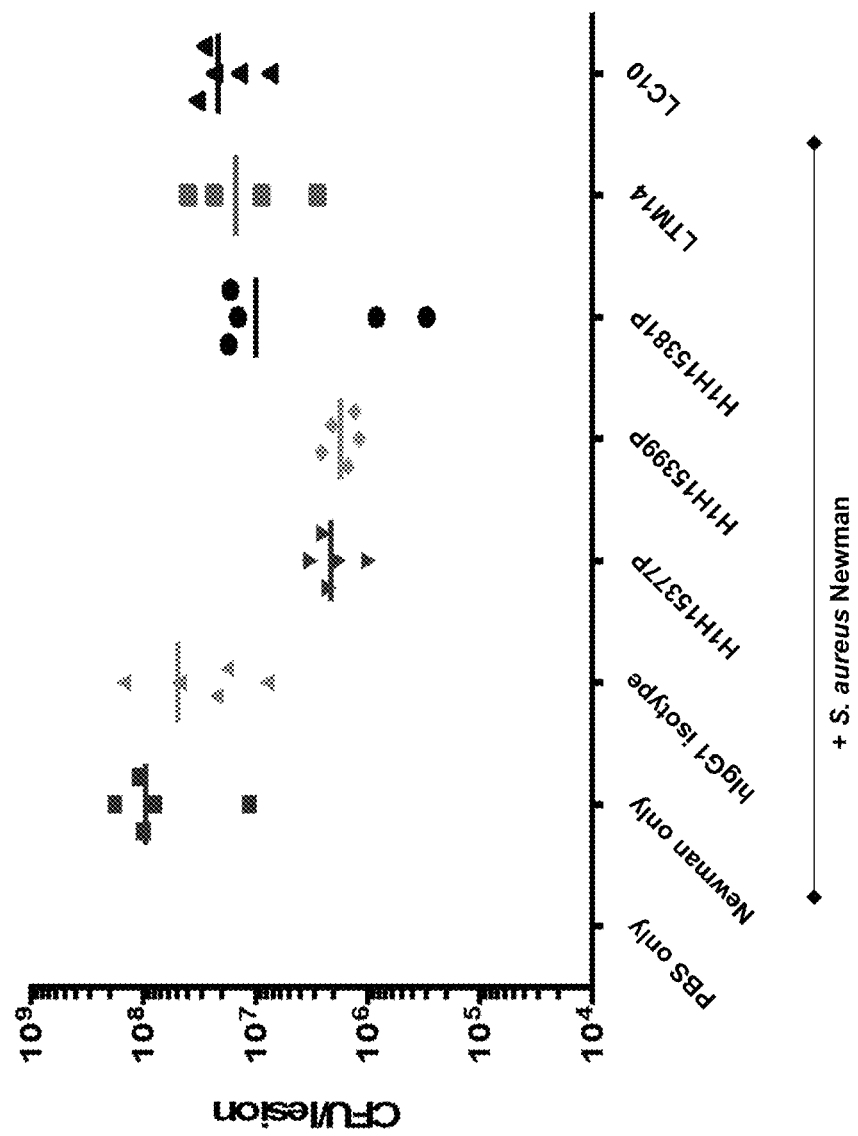

Antibodies H1H15377P and H1H15399P reduced the bacterial burden in the skin of mice infected with both S. aureus CA-127 (FIG. 7a) and Newman (FIG. 7b); specifically, 5 mg/kg of either antibody resulted in a 1-1.5 log reduction in skin bacterial burden, compared to the levels of bacterial burden determined for the animals treated with the isotype-matched control antibody. The same dose of H1H15381P, LTM14 or LC10 resulted in 0-0.5 log reduction in skin bacterial burden. The results indicate that H1H15377P and H1H15399P were most effective in reducing bacterial burden in the skin of infected mice.

Example 11. In Vivo Efficacy of Anti-Hemolysin A mAbs Administered Therapeutically In order to determine if mAbs in the invention can also decrease lesion size if administered after infection, purified antibodies were tested therapeutically in an in vivo dermonecrosis model using female BALB/c mice (n=5). Two days prior to infection, fur was removed from the abdominal area by shaving and applying hair removal lotion. On the day of infection, mice were challenged subcutaneously, on the right side of the abdomen, with 50 μls of S. aureus CA-127 (~1-2×10$^8$ CFU/mouse) that had been grown to log phase (OD$_{600}$≤1) in TSB at 37° C., washed and resuspended in PBS. Two hours after infection, mice were injected i.p. on the left side of the abdomen with a single dose of 0.5 mg/kg of each individual antibody: H1H15375P, H1H15376P, H1H15377P, H1H15378P, H1H15379P, H1H15380P, H1H15381P, H1H15399P, H1H15404P, H1H15405P, H1H15408P, H1H15410P, H1H15414P, H1H15418P2, H1H15420P2 or an isotype-matched control antibody. Mouse lesions were measured with a digital caliper on day 2 post-infection.

All antibodies of the invention were efficacious in reducing lesion size when administered to animals at 0.5 mg/kg two hours after infection (Table 11). Reductions in dermonecrotic lesion sizes ranged from 50-83%. Eight of the antibodies (H1H15376P, H1H15377P, H1H15378P, H1H15379P, H1H15380P, H1H15399P, H1H15418P2 and H1H15420P2) showed >70% reduction in lesions sizes.

TABLE 11

Lesion size comparison for anti-Hemolysin A monoclonal antibodies in a therapeutic murine dermonecrosis model, Day 2 post-infection

| | Mice receiving 0.5 mg/kg mAb and infected with 1.1 × 10$^8$ CFU S. aureus CA-127 | | | |
|---|---|---|---|---|
| AbPID | Mice (n) | Decrease Relative to Isotype (%) | Mean Lesion Size (mm) | SD |
| H1H15375P | 5 | 69.2 | 52.8 | 44.9 |
| H1H15376P | 5 | 79.4 | 35.4 | 11.4 |
| H1H15377P | 5 | 73.1 | 46.2 | 35.0 |
| H1H15378P | 5 | 82.8 | 29.6 | 8.3 |
| H1H15379P | 5 | 74.5 | 43.8 | 19.4 |
| H1H15380P | 5 | 79.5 | 35.2 | 15.8 |
| H1H15381P | 5 | 59.0 | 70.5 | 53.2 |
| H1H15399P | 4 | 73.2 | 46.1 | 15.4 |
| H1H15404P | 5 | 56.2 | 75.3 | 24.4 |
| H1H15405P | 5 | 69.8 | 51.9 | 19.1 |
| H1H15408P | 5 | 63.9 | 62.1 | 21.3 |
| H1H15410P | 5 | 50.2 | 85.5 | 38.1 |
| H1H15414P | 5 | 80.9 | 32.8 | 12.9 |
| H1H15418P2 | 5 | 70.6 | 50.4 | 11.2 |
| H1H15420P2 | 5 | 73.7 | 45.2 | 30.1 |
| Isotype control | 5 | 0.0 | 171.8 | 97.9 |

Example 12. In Vivo Efficacy of Anti-Hemolysin A mAbs in an Acute Pneumonia Model Using a Methicillin-Sensitive Staphylococcus aureus (MSSA) Strain Survival of mice administered antibodies at 5 mg/kg prophylactically. In order to determine the efficacy of the mAbs against a MSSA strain when administered prophylactically, the following antibodies H1H15375P, H1H15376P, H1H15377P, H1H15378P, H1H15379P, H1H15380P, H1H15381P, H1H15399P and H1H15414P were selected for study in an acute pneumonia model using S. aureus Newman (modified from Bubeck Wardenburg et al., (2007) Infect. Immun. 75:1040-1044). Female C57BL/6 mice (n=5) were injected i.p. with a single dose of 5 mg/kg of H1H15375P, H1H15376P, H1H15377P, H1H15378P, H1H15379P, H1H15380P, H1H15381P, H1H15399P, H1H15414P or an isotype-matched control antibody. One day post-injection of the mAbs, mice were challenged intra-tracheally with 50 μls of S. aureus Newman (1.7×10$^8$ CFU/mouse) that had been grown to log phase (OD$_{600}$≤1) in TSB at 37° C., washed and resuspended in PBS. The mice were monitored for survival for a total of six days post-infection.

As seen in Table 12, administration of antibody H1H15375P, H1H15376P, H1H15378P, H1H15379P, H1H15380P, H1H15381P, H1H15399P or H1H15414P resulted in 100% survival. Administration of H1H15377P resulted in 80% survival to day 6. All antibodies of the invention increased survival of mice infected with a S. aureus MSSA strain when given prophylactically at 5 mg/kg in an acute pneumonia model of infection.

TABLE 12

Survival of mice administered 5 mg/kg anti-Hemolysin A monoclonal antibodies prophylactically in an acute pneumonia model using an MSSA strain

| | S. aureus Newman (MSSA) mAb dose: 5 mg/kg | |
|---|---|---|
| AbPID | Mice (n) | Survival at D6 post-infection (%) |
| H1H15375P | 5 | 100 |
| H1H15376P | 5 | 100 |
| H1H15377P | 5 | 80 |
| H1H15378P | 5 | 100 |
| H1H15379P | 5 | 100 |
| H1H15380P | 5 | 100 |
| H1H15381P | 5 | 100 |
| H1H15399P | 5 | 100 |
| H1H15414P | 5 | 100 |
| Isotype control | 5 | 20 |

Survival of mice administered antibodies at 2.5 mg/kg prophylactically. To determine if the antibodies would also be effective at a lower dose in the acute pneumonia model against a MSSA strain, C57BL/6 female mice (n=5), were injected i.p. with a single dose of 2.5 mg/kg of H1H15375P, H1H15377P, H1H15378P, H1H15379P, H1H15380P, H1H15381P, H1H15399P, H1H15414P, or an isotype-matched antibody. One day post-injection of the mAbs, mice were challenged intra-tracheally with 50 μls of S. aureus Newman (7.5×10$^7$ CFU/mouse) that had been grown to log phase (OD$_{600}$≤1) in TSB at 37° C., washed and resuspended in PBS. The mice were monitored for survival for a total of six days post-infection.

As seen in Table 12, administration of antibody H1H15376P, H1H15377P, H1H15379P, H1H15381P, H1H15399P or H1H15414P resulted in 100% survival to day 6, whereas, administration of antibody H1H15378P or H1H15380P resulted in 80% survival. Antibody H1H15375P was less efficacious when compared to the other antibodies, providing only 60% protection (Table 13).

The results indicate that antibodies H1H15375P, H1H15376P, H1H15378P, H1H15379P, H1H15380P, H1H15381P, H1H15399P, H1H15414P and H1H15377P are efficacious in reducing cytotoxic effects of Hemolysin A and increasing survival in a murine acute pneumonia model using S. aureus MSSA strain even when the mAbs are administered at a lower dose.

TABLE 13

Survival of mice administered 2.5 mg/kg anti-Hemolysin A monoclonal antibodies prophylactically in an acute pneumonia model using an MSSA strain

| AbPID | S. aureus Newman (MSSA) mAb dose: 2.5 mg/kg | |
|---|---|---|
| | Mice (n) | Survival at D6 post-infection (%) |
| H1H15375P | 5 | 60 |
| H1H15376P | 5 | 100 |
| H1H15377P | 5 | 100 |
| H1H15378P | 5 | 80 |
| H1H15379P | 5 | 100 |
| H1H15380P | 5 | 80 |
| H1H15381P | 5 | 100 |
| H1H15399P | 5 | 100 |
| H1H15414P | 5 | 100 |
| Isotype control | 5 | 0 |

Example 13. In Vivo Efficacy of Anti-Hemolysin A mAbs in an Acute Pneumonia Model Using a Methicillin-Resistant *Staphylococcus aureus* (MRSA) Strain Survival of mice administered antibodies at 5 mg/kg prophylactically. In order to test the efficacy of the mAbs against a MRSA strain, the following antibodies H1H15375P, H1H15376P, H1H15377P, H1H15378P, H1H15379P, H1H15380P, H1H15381P, H1H15399P and H1H15414P were selected for study in a prophylactic acute pneumonia model using *S. aureus* CA-127. Female C57BL/6 mice (n=5) were injected i.p. with a single dose of 5 mg/kg of H1H15375P, H1H15376P, H1H15377P, H1H15378P, H1H15379P, H1H15380P, H1H15381P, H1H15399P, H1H15414P, or an isotype-matched control antibody. One day post-injection of the mAbs, mice were challenged intra-tracheally with 50 μls containing either $2.2 \times 10^8$ CFU (low inoculum) or $4.8 \times 10^8$ CFU (high inoculum) of *S. aureus* CA-127 that had been grown to log phase ($OD_{600} \leq 1$) in TSB at 37° C., washed and resuspended in PBS. The mice were monitored for survival for a total of six days post-infection.

Eight of the nine invention antibodies showed efficacy when mice were challenged with the low inoculum. Specifically, antibodies H1H15375P, H1H15377P, H1H15378P, H1H15379P, H1H15380P, H1H15381P and H1H15399P were equally efficacious, resulting in 100% survival to day 6 (Table 14). Administration of antibody H1H15414P resulted in 80% survival. H1H15376P demonstrated no protection, as mice receiving this antibody did not survive to day 6. None of the animals treated with the isotype-matched antibody survived to day 6 (Table 13)

At a higher inoculum, greater differentiation in efficacy between the invention antibodies was observed. As seen in Table 13, antibodies H1H15377P and H1H15399P were the most efficacious of the antibodies tested, resulting in 100% survival to day 6. Administration of antibodies H1H15414P, H1H15378P, H1H15379P and H1H15381P resulted in 60% survival to day 6, whereas none of the animals in the group treated with the isotype-matched control antibody survived to day 6. Antibodies H1H15375P, H1H15376P and H1H15380P had lower efficacy than the other invention antibodies tested, resulting in 20%, 0% or 40% survival to day 6, respectively (Table 13).

The results indicate that H1H15375P, H1H15377P, H1H15378P, H1H15379P, H1H15380P, H1H15381P, H1H15399P and H1H15414P are efficacious at reducing the cytotoxic effects of Hemolysin A and increasing survival when given prophylactically at 5 mg/kg in an acute pneumonia model of infection with a lower inoculum of a *S. aureus* MRSA strain. Two antibodies, H1H15377P and H1H15399P were also 100% efficacious when a higher inoculum of a *S. aureus* MRSA strain was used in this model.

TABLE 14

Survival of mice administered 5 mg/kg anti-Hemolysin A monoclonal antibodies prophylactically in an acute pneumonia model using a MRSA strain

| AbPID | S. aureus CA-127 (MRSA) mAb dose: 5 mg/kg Mice (n) | Low Inoculum ($2.2 \times 10^8$ CFU) Survival (%) | High Inoculum ($4.8 \times 10^8$ CFU) Survival (%) |
|---|---|---|---|
| H1H15375P | 5 | 100 | 20 |
| H1H15376P | 5 | 0 | 0 |
| H1H15377P | 5 | 100 | 100 |
| H1H15378P | 5 | 100 | 60 |
| H1H15379P | 5 | 100 | 60 |
| H1H15380P | 5 | 100 | 40 |
| H1H15381P | 5 | 100 | 60 |
| H1H15399P | 5 | 100 | 100 |
| H1H15414P | 5 | 80 | 60 |
| Isotype control | 5 | 0 | 0 |

Survival of mice administered antibodies at 2.5 mg/kg prophylactically. To determine if the antibodies would also be effective at a lower dose in the acute pneumonia model against a MRSA strain, female C57BL/6 mice (n=5) were injected i.p. with a single dose of 2.5 mg/kg of H1H15375P, H1H15376P, H1H15377P, H1H15378P, H1H15379P, H1H15380P, H1H15381P, H1H15399P, H1H15414P, or an isotype-matched control antibody. One day post-injection of the mAbs, mice were challenged intra-tracheally with 50 μls of *S. aureus* CA-127 ($3.0 \times 10^8$ CFU/mouse) that had been grown to log phase ($OD_{600} \leq 1$) in TSB at 37° C., washed and resuspended in PBS. The mice were monitored for survival for a total of six days post-infection.

All invention antibodies tested (H1H15375P, H1H15377P, H1H15378P, H1H15379P, H1H15380P, H1H15381P, H1H15399P or H1H15414P) were equally efficacious, resulting in 100% survival to day 6, whereas none of the animals in the group treated with the isotype-matched control antibody survived until day 6 (Table 15). The results indicate that H1H15375P, H1H15377P, H1H15378P, H1H15379P, H1H15380P, H1H15381P, H1H15399P and H1H15414P are efficacious at reducing the cytotoxic effects of Hemolysin A and increasing survival when given prophylactically at 2.5 mg/kg in an acute pneumonia model of infection with a *S. aureus* MRSA strain.

TABLE 15

Survival of mice administered 2.5 mg/kg anti-Hemolysin A monoclonal antibodies prophylactically in an acute pneumonia model using MRSA strain

| | S. aureus CA-127 (MRSA) mAb dose: 2.5 mg/kg | |
|---|---|---|
| AbPID | Mice (n) | Survival at D6 post-infection (%) |
| H1H15375P | 5 | 100 |
| H1H15377P | 5 | 100 |
| H1H15378P | 5 | 100 |
| H1H15379P | 5 | 100 |
| H1H15380P | 5 | 100 |
| H1H15381P | 5 | 100 |
| H1H15399P | 5 | 100 |
| H1H15414P | 5 | 100 |
| Isotype control | 5 | 0 |

Bacteria counts in lungs of mice administered H1H15399P and H1H15376P prophylactically. Two purified antibodies of the invention, H1H15399P and H1H15376P, were tested in an acute pneumonia study to determine if there were any observed changes in the bacterial burden in the lungs of mice prophylactically treated with the antibodies. Groups of female C57BL/6 mice (n=5) were injected i.p. with one of three doses of H1H15399P, a single dose of H1H15376P, or an isotype-matched control antibody (5 mg/kg). One day post-injection, mice were challenged intra-tracheally with 50 µls of S. aureus CA-127 ($1.6 \times 10^8$ CFU/mouse) that had been grown to log phase ($OD_{600} \leq 1$) in TSB at 37° C., washed and resuspended in PBS. The mice were euthanized by anesthesia 18 hours post-infection and lungs were extracted and homogenized. Serial dilutions of the lung lysates were plated on TSA plates. Plates were incubated overnight (16-18 hours) at 37° C. and bacterial colonies were counted the next day for determination of bacterial burden.

Antibody H1H15399P reduced the bacterial burden in lungs of infected mice (Table 16); specifically, all three doses of H1H15399P tested resulted in a 1 to 1.5 log reduction in lung bacterial burden, compared to the levels of bacterial burden determined for the animals treated with the isotype-matched control antibody. In addition, this decrease in lung bacterial burden was dose-dependent. Antibody H1H15376P did not display any efficacy in this model, showing lung bacterial lung burden similar to the isotype-matched antibody. The results indicate that H1H15399P was able to reduce bacterial burden in the lungs of infected mice.

TABLE 16

Bacterial counts in lungs of mice administered anti-Hemolysin A monoclonal antibodies H1H15399P and H1H15376P prophylactically in an acute pneumonia model using a MRSA strain

| | | | Organ Burden | |
|---|---|---|---|---|
| AbPID | Mice (n) | Dose (mg/kg) | mean CFU/lung | SD |
| H1H15399P | 5 | 5 | 5.50E+06 | 2.30E+06 |
| | 5 | 2.5 | 1.11E+07 | 1.10E+07 |
| | 5 | 1.25 | 1.04E+07 | 7.06E+06 |
| H1H15376P | 5 | 5 | 1.47E+08 | 2.33E+08 |
| Isotype control | 4 | 5 | 2.45E+08 | 1.72E+08 |

To further interrogate the ability of the anti-Hemolysin A mAbs to reduce bacterial burden in the lungs, three mAbs (H1H15377P, H1H15381P, H1H15399P) that had demonstrated increased survival were administered prophylactically at two different doses and compared to two other anti-Hemolysin A mAbs, LC10 and LTM14. Groups of female C57BL/6 mice (n=5) were injected i.p. with a single dose of 1.25 mg/kg or 0.325 mg/kg of each individual antibody: H1H15377P, H1H15381P, H1H15399P, LTM14, LC10 or an isotype-matched control antibody. One day post-injection, mice were challenged intra-tracheally with 50 µls of S. aureus CA-127 ($1.3 \times 10^8$ CFU/mouse) that had been grown to log phase ($OD_{600} \leq 1$) in TSB at 37° C., washed and resuspended in PBS. The mice were euthanized by anesthesia 18 hours post-infection and lungs were extracted and homogenized. Serial dilutions of the lung lysates were plated on TSA plates. Plates were incubated overnight (16-18 hours) at 37° C. and bacterial colonies were counted the next day for determination of bacterial burden.

Figure 8A:
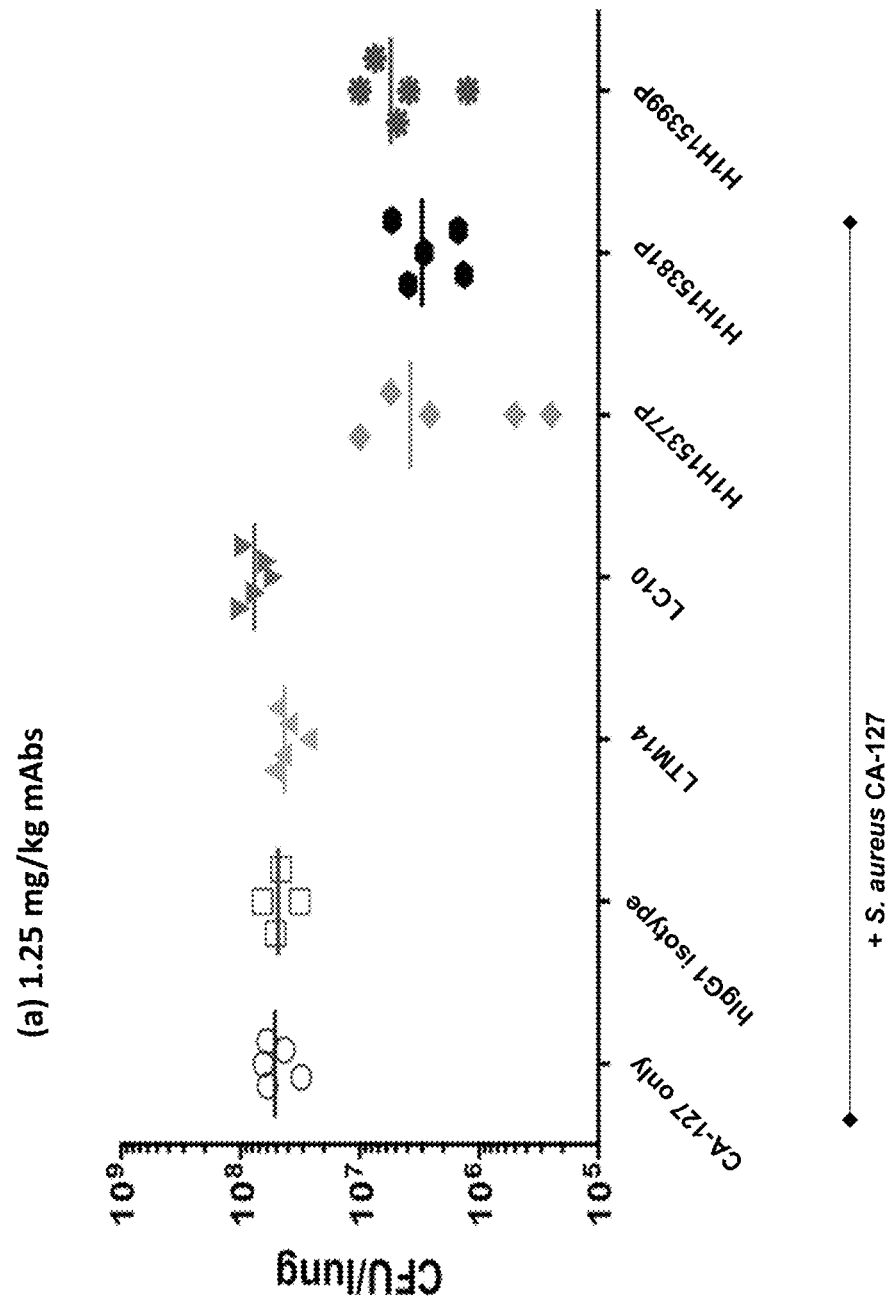
FIGS. 8a and 8b show bacterial burden in lungs of mice infected with *S.aureus* CA-127 treated with various antibodies (H1H15377P, H1H15381P, H1H15399P, LTM14, LC10 or control antibody) at 1.25 or 0.325 mg/kg.
Figure 8B:
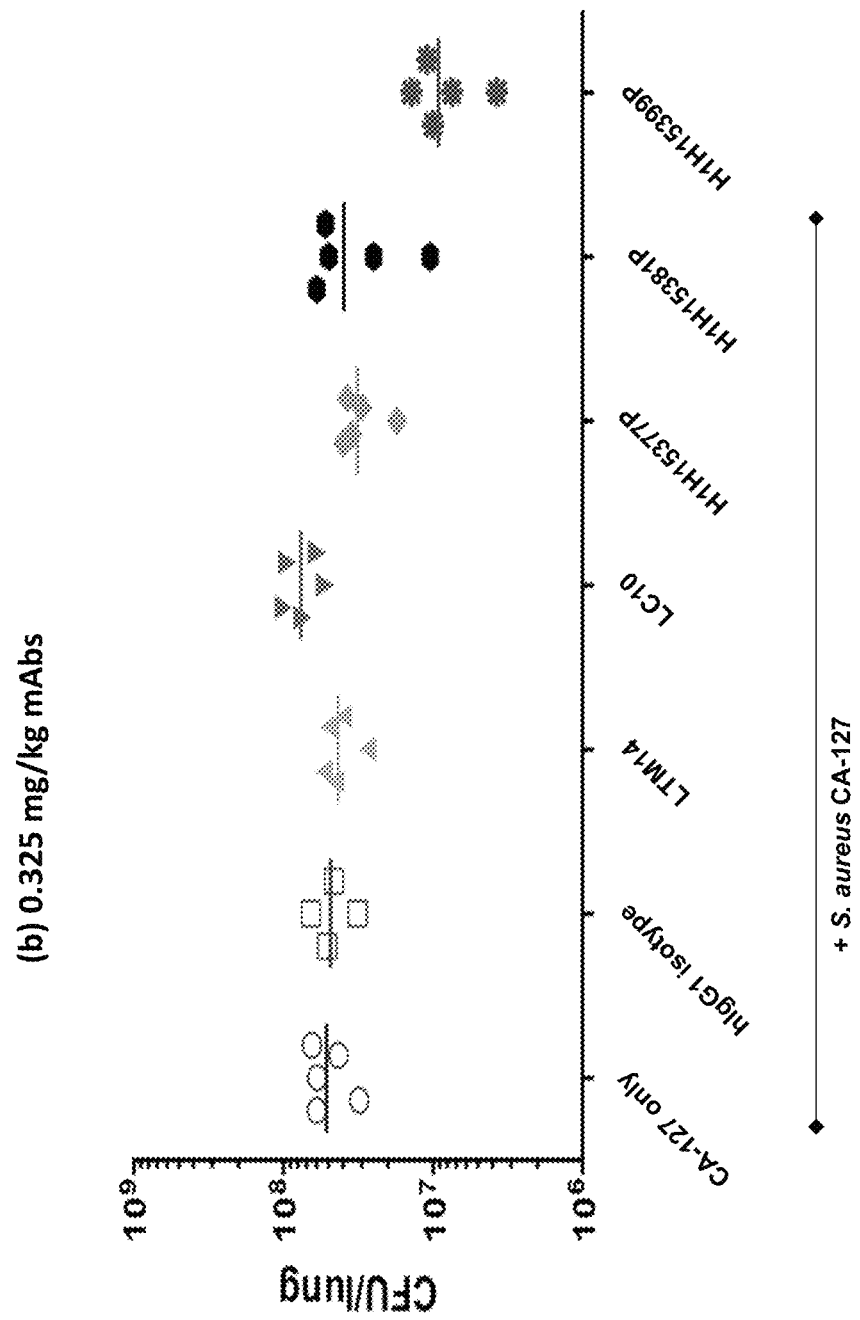

All three antibodies of the invention tested were efficacious when administered at 1.25 mg/kg compared to LTM14, LC10 and isotype-matched control antibody, decreasing bacterial burden in the lungs by 1 log (FIG. 8a). H1H15399P was also effective at decreasing bacterial burden when administered at 0.325 mg/kg (FIG. 8b). All other Hemolysin A mAbs tested did not significantly reduce bacteria in the lungs of the mice at this lower dose (FIG. 8b).

Example 14. Octet Cross-Competition Between Different Anti-Hemolysin A Monoclonal Antibodies Using Pre-Complex Method To assess whether two antibodies compete with one another for binding epitopes on Hemolysin A (purified from Staphylococcus aureus), binding competition between anti-Hemolysin A monoclonal antibodies was determined using a real time, label-free bio-layer interferometry assay on an Octet RED384 biosensor (Pall ForteBio Corp.). The entire experiment was performed at 25° C. in 0.01M HEPES pH7.4, 0.15M NaCl, 3 mM EDTA, 0.05% v/v Tween-20, 1.0 mg/mL BSA (Octet HBS-ET buffer) with the plate shaking at the speed of 1000 rpm. About 1.5-2.5 nm of anti-Hemolysin A monoclonal antibody was first captured onto anti-hFc antibody coated Octet biosensor tips (Pall ForteBio Corp., #18-5060) by submerging the tips for two minutes into wells containing a 50 µg/mL solution of anti-Hemolysin monoclonal antibody (mAb-1). The antibody captured biosensor tips were then saturated with a blocking H4H isotype control monoclonal antibody (blocking mAb) by dipping into wells containing 100 µg/mL solution of blocking mAb for three minutes. The biosensor tips were then subsequently dipped for four minutes into wells, containing 100 nM Hemolysin A previously incubated for 2 hours with 1 µM of a second anti-Hemolysin A monoclonal antibody (mAb-2). The biosensor tips were washed in Octet HBS-ET buffer in between every step of the experiment. The real-time binding response was monitored during the course of the experiment and the binding response at the end of every step was recorded. The response of Hemolysin A pre-complexed mAb-2 binding to mAb-1 was corrected for background binding, compared and competitive/non-competitive behavior of different anti-Hemolysin A monoclonal antibodies was determined. Table 17 explicitly defines the relationships of antibodies competing in both directions, independent of the order of binding.

TABLE 17

Cross-competition of anti-Hemolysin A antibodies for binding to Hemolysin A

| First mAb (mAb-1) Captured using AHC Octet Biosensors | mAb-2 Antibodies Shown to Compete with mAb-1 |
|---|---|
| H1H15404P | H1H15410P, H1H15376P, H1H15418P2 |
| H1H15410P | H1H15404P, H1H15376P, H1H15418P2 |
| H1H15376P | H1H15404P, H1H15410P, H1H15418P2, H1H15375P, H1H15377P, H1H15405P |
| H1H15418P2 | H1H15404P, H1H15410P, H1H15376P, H1H15375P, H1H15377P, H1H15405P |
| H1H15375P | H1H15376P, H1H15418P2, H1H15377P, H1H15405P, H1H15379P, H1H15408P, H1H15381P, H1H15378P, H1H15399P |
| H1H15377P | H1H15376P, H1H15418P2, H1H15375P, H1H15405P, H1H15379P, H1H15408P, H1H15381P, H1H15378P, H1H15399P |
| H1H15405P | H1H15376P, H1H15418P2, H1H15375P, H1H15377P, H1H15379P, H1H15408P, H1H15381P, H1H15378P, H1H15399P |
| H1H15379P | H1H15375P, H1H15377P, H1H15405P, H1H15408P, H1H15381P, H1H15378P, H1H15399P, H1H15420P2, H1H15380P, H1H15414P |
| H1H15408P | H1H15375P, H1H15377P, H1H15405P, H1H15379P, H1H15381P, H1H15378P, H1H15399P, H1H15420P2, H1H15380P, H1H15414P |
| H1H15381P | H1H15375P, H1H15377P, H1H15405P, H1H15379P, H1H15408P, H1H15378P, H1H15399P, H1H15420P2, H1H15380P, H1H15414P |
| H1H15378P | H1H15375P, H1H15377P, H1H15405P, H1H15379P, H1H15408P, H1H15381P, H1H15399P, H1H15420P2, H1H15380P, H1H15414P |
| H1H15399P | H1H15375P, H1H15377P, H1H15405P, H1H15379P, H1H15408P, H1H15381P, H1H15378P, H1H15420P2, H1H15380P, H1H15414P |
| H1H15420P2 | H1H15379P, H1H15408P, H1H15381P, H1H15378P, H1H15399P, H1H15380P, H1H15414P |
| H1H15380P | H1H15379P, H1H15408P, H1H15381P, H1H15378P, H1H15399P, H1H15420P2 |
| H1H15414P | H1H15379P, H1H15408P, H1H15381P, H1H15378P, H1H15399P, H1H15420P2 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A polynucleotide encoding a heavy chain variable region (HCVR) of an antibody or antigen-binding fragment thereof that binds to Hemolysin A, wherein the HCVR comprises three heavy chain complementarity determining regions (CDRs) (HCDR1, HCDR2, and HCDR3), wherein the HCDR1 comprises the amino acid sequence set forth in SEQ ID NO: 144, the HCDR2 comprises the amino acid sequence set forth in SEQ ID NO: 146, and the HCDR3 comprises the amino acid sequence set forth in SEQ ID NO: 148.

2. The polynucleotide of claim 1, wherein the HCVR comprises the amino acid sequence set forth in SEQ ID NO: 142.

3. The polynucleotide of claim 1, wherein the polynucleotide comprises the HCDR1 nucleic acid sequence set forth in SEQ ID NO: 143; the HCDR2 nucleic acid sequence set forth in SEQ ID NO: 145; and the HCDR3 nucleic acid sequence set forth in SEQ ID NO: 147.

4. The polynucleotide of claim 1, wherein the polynucleotide comprises the HCVR nucleic acid sequence set forth in SEQ ID NO: 141.

5. The polynucleotide of claim 1, wherein the antibody further comprises an immunoglobulin constant region.

6. The polynucleotide of claim 5, wherein the immunoglobulin constant region is an IgG1 constant region.

7. The polynucleotide of claim 1, wherein the antibody comprises the heavy chain amino acid sequence set forth in SEQ ID NO: 158.

8. The polynucleotide of claim 1, wherein the polynucleotide comprises the heavy chain nucleic acid sequence set forth in SEQ ID NO: 157.

9. A vector comprising the polynucleotide of claim 1.

10. A polynucleotide encoding a light chain variable region (LCVR) of an antibody or antigen-binding fragment thereof that binds to Hemolysin A, wherein the LCVR comprises three light chain complementarity determining regions (CDRs) (LCDR1, LCDR2, and LCDR3), wherein the LCDR1 comprises the amino acid sequence set forth in SEQ ID NO: 152, the LCDR2 comprises the amino acid sequence set forth in SEQ ID NO: 154, and the LCDR3 comprises the amino acid sequence set forth in SEQ ID NO: 156.

11. The polynucleotide of claim 10, wherein the LCVR comprises the amino acid sequence of SEQ ID NO: 150.

12. The polynucleotide of claim 10, wherein the polynucleotide comprises the LCDR1 nucleic acid sequence set forth in SEQ ID NO: 151; the LCDR2 nucleic acid sequence set forth in SEQ ID NO: 153; and the LCDR3 nucleic acid sequence set forth in SEQ ID NO: 155.

13. The polynucleotide of claim 10, wherein the polynucleotide comprises the LCVR nucleic acid sequence set forth in SEQ ID NO: 149.

14. The polynucleotide of claim 10, wherein the antibody comprises the light chain amino acid sequence set forth in SEQ ID NO: 160.

15. The polynucleotide of claim 10, wherein the polynucleotide comprises the light chain nucleic acid sequence set forth in SEQ ID NO: 159.

16. A vector comprising the polynucleotide of claim 10.

* * * * *